US011908560B2

(12) United States Patent
Jacob et al.

(10) Patent No.: US 11,908,560 B2
(45) Date of Patent: Feb. 20, 2024

(54) CANCER PROCESS EVALUATION

(71) Applicant: ONCOHOST LTD., Binyamina (IL)

(72) Inventors: Eyal Jacob, Haifa (IL); Michal Harel, Kfar Saba (IL); Ben Yellin, Ganei Am (IL); Coren Lahav, Tel Aviv (IL); Itamar Sela, Ramat-Gan (IL); Yehonatan Elon, Jerusalem (IL)

(73) Assignee: ONCOHOST LTD., Binyamina (IL)

( * ) Notice: Subject to any disclaimer, the term of this patent is extended or adjusted under 35 U.S.C. 154(b) by 0 days.

(21) Appl. No.: 17/886,095

(22) Filed: Aug. 11, 2022

(65) Prior Publication Data

US 2023/0084735 A1 Mar. 16, 2023

Related U.S. Application Data

(60) Provisional application No. 63/324,116, filed on Mar. 27, 2022, provisional application No. 63/231,770, filed on Aug. 11, 2021.

(51) Int. Cl.
*G16H 20/10* (2018.01)
*G16B 20/00* (2019.01)
*G16B 40/20* (2019.01)

(52) U.S. Cl.
CPC .............. *G16H 20/10* (2018.01); *G16B 20/00* (2019.02); *G16B 40/20* (2019.02)

(58) Field of Classification Search
CPC ......... G16H 20/10; G16B 20/00; G16B 40/20
See application file for complete search history.

(56) References Cited

U.S. PATENT DOCUMENTS

| 5,595,756 | A | 1/1997 | Bally et al. |
| 9,984,201 | B2 | 5/2018 | Zhang et al. |
| 11,155,614 | B2 | 10/2021 | Shaked et al. |
| 2016/0024585 | A1 | 1/2016 | Nixon et al. |
| 2017/0114125 | A1 | 4/2017 | Sabbadini et al. |

FOREIGN PATENT DOCUMENTS

| JP | 2008502326 | A | | 1/2008 | |
| JP | 2011526674 | A | | 10/2011 | |
| JP | 2015512612 | A | | 4/2015 | |
| JP | 2015516806 | A | | 6/2015 | |
| JP | 2016-520800 | A | | 7/2016 | |
| JP | 2016535275 | A | | 11/2016 | |
| WO | 2005119260 | A2 | | 12/2005 | |
| WO | 2009032084 | A1 | | 3/2009 | |
| WO | WO-2012037378 | A2 | * | 3/2012 | ............. A61K 33/24 |
| WO | 2012151574 | A1 | | 11/2012 | |
| WO | 2013106765 | A1 | | 7/2013 | |
| WO | 2013148288 | A1 | | 10/2013 | |
| WO | 2016156501 | A1 | | 10/2016 | |
| WO | 2016156601 | A1 | | 10/2016 | |
| WO | 2017011907 | A1 | | 1/2017 | |
| WO | 2017024207 | A1 | | 2/2017 | |
| WO | 2017036020 | A1 | | 3/2017 | |
| WO | 2017040960 | A1 | | 3/2017 | |
| WO | 2017132536 | A1 | | 8/2017 | |
| WO | 2017140826 | A1 | | 8/2017 | |
| WO | 2018071824 | A1 | | 4/2018 | |
| WO | 2018225062 | A1 | | 12/2018 | |
| WO | 2018225063 | A1 | | 12/2018 | |
| WO | 2019165021 | A1 | | 8/2019 | |

OTHER PUBLICATIONS

Wilson JJ, Burgess R, Mao YQ, Luo S, Tang H, Jones VS, Weisheng B, Huang RY, Chen X, Huang RP. Antibody arrays in biomarker discovery. Adv Clin Chem. 2015;69:255-324. doi: 10.1016/bs.acc. 2015.01.002. Epub Feb. 26, 2015. PMID: 25934364.

Shaked Y. Balancing efficacy of and host immune responses to cancer therapy: the yin and yang effects. Nat Rev Clin Oncol. Oct. 2016;13(10):611-26. doi: 10.1038/nrclinonc.2016.57. Epub Apr. 26, 2016. PMID: 27118493.

Katz OB, Shaked Y. Host effects contributing to cancer therapy resistance. Drug Resist Updat. Mar. 2015;19:33-42. doi: 10.1016/j.drup.2014.12.002. Epub Dec. 26, 2014. PMID: 25575621.

Shaked Y. The pro-tumorigenic host response to cancer therapies. Nat Rev Cancer. Dec. 2019;19(12):667-685. doi: 10.1038/s41568-019-0209-6. Epub Oct. 23, 2019. PMID: 31645711.

Josephs SF, Ichim TE, Prince SM, Kesari S, Marincola FM, Escobedo AR, Jafri A. Unleashing endogenous TNF-alpha as a cancer immunotherapeutic. J Transl Med. Aug. 31, 2018;16(1):242. doi: 10.1186/s12967-018-1611-7. PMID: 30170620; PMCID: PMC6119315.

Hanahan D, Weinberg RA. The hallmarks of cancer. Cell. Jan. 7, 2000;100(1):57-70. doi: 10.1016/s0092-8674(00)81683-9. PMID: 10647931.

Hanahan D, Weinberg RA. Hallmarks of cancer: the next generation. Cell. Mar. 4, 2011;144(5):646-74. doi: 10.1016/j.cell.2011.02. 013. PMID: 21376230.

Figueroa RL, Zeng-Treitler Q, Kandula S, Ngo LH. Predicting sample size required for classification performance. BMC Med Inform Decis Mak. Feb. 15, 2012;12:8. doi: 10.1186/1472-6947-12-8. PMID: 22336388; PMCID: PMC3307431.

Chindelevitch L, Ziemek D, Enayetallah A, Randhawa R, Sidders B, Brockel C, Huang ES. Causal reasoning on biological networks: interpreting transcriptional changes. Bioinformatics. Apr. 15, 2012;28(8):1114-21. doi: 10.1093/bioinformatics/bts090. Epub Feb. 21, 2012. PMID: 22355083.

Dubovenko A, Nikolsky Y, Rakhmatulin E, Nikolskaya T. Functional Analysis of OMICs Data and Small Molecule Compounds in an Integrated "Knowledge-Based" Platform. Methods Mol Biol. 2017;1613:101-124. doi: 10.1007/978-1-4939-7027-8_6. PMID: 28849560.

(Continued)

*Primary Examiner* — Jerry Lin
(74) *Attorney, Agent, or Firm* — The Roy Gross Law Firm, LLC; Roy Gross

(57) ABSTRACT

Methods of selecting a therapeutic agent to treat a cancer in a subject comprising receiving a plurality of protein data element values representing levels of the proteins in a biological sample from the subject, classifying each protein as a member of a process class, for each process class calculating a process score that represents the prominence of the process class to cancer treatment resistance and selecting at least one therapeutic agent that targets a selected process based on the process score. Systems for selecting a therapeutic agent are also provided.

19 Claims, 19 Drawing Sheets
(14 of 19 Drawing Sheet(s) Filed in Color)

(56) References Cited

OTHER PUBLICATIONS

Liebermeister W, Noor E, Flamholz A, Davidi D, Bernhardt J, Milo R. Visual account of protein investment in cellular functions. Proc Natl Acad Sci U S A. Jun. 10, 2014;111(23):8488-93. doi: 10.1073/pnas.1314810111. Epub Jun. 2, 2014. PMID: 24889604; PMCID: PMC4060655.

ClinicalTrials.gov [Internet]. Bethesda (MD): National Library of Medicine (US)., "Identifier:NCT04056247, Predicting Responsiveness in Oncology Patients Based on Host ResponseEvaluation During Anti Cancer Treatments (Prophetic)," Aug. 14, 2019. [Online]. Available: https://www.clinicaltrials.gov/ct2/show/NCT04056247.

Arjaans S, Wagner BD, Mourani PM, Mandell EW, Poindexter BB, Berger RMF, Abman SH. Early angiogenic proteins associated with high risk for bronchopulmonary dysplasia and pulmonary hypertension in preterm infants. Am J Physiol Lung Cell Mol Physiol. Apr. 1, 2020;318(4):L644-L654. doi: 10.1152/ajplung.00131.2019. Epub Jan. 22, 2020. PMID: 31967847; PMCID: PMC7191476.

Assarsson E, Lundberg M, Holmquist G, Bjorkesten J, Thorsen SB, Ekman D, Eriksson A, Rennel Dickens E, Ohlsson S, Edfeldt G, Andersson AC, Lindstedt P, Stenvang J, Gullberg M, Fredriksson S. Homogenous 96-plex PEA immunoassay exhibiting high sensitivity, specificity, and excellent scalability. PLoS One. Apr. 22, 2014;9(4):e95192. doi: 10.1371/journal.pone.0095192. PMID: 24755770; PMCID: PMC3995906.

Lundberg M, Eriksson A, Tran B, Assarsson E, Fredriksson S. Homogeneous antibody-based proximity extension assays provide sensitive and specific detection of low-abundant proteins in human blood. Nucleic Acids Res. Aug. 2011;39(15):e102. doi: 10.1093/nar/gkr424. Epub Jun. 6, 2011. PMID: 21646338; PMCID: PMC3159481.

Khononov I, Jacob E, Fremder E, Dahan N, Harel M, Raviv Z, Krastev B, Shaked Y. Host response to immune checkpoint inhibitors contributes to tumor aggressiveness. J Immunother Cancer. Mar. 2021;9(3):e001996. doi: 10.1136/jitc-2020-001996. PMID: 33707313; PMCID: PMC7957134.

Sheng et al. "The Relationship Between Serum Interleukin-6 and the Recurrence of Hepatitis B Virus Related Hepatocellular Carcinoma after Curative Resection". Medicine (Baltimore). Jun. 2015;94(24):e941. doi: 10.1097/MD.0000000000000941. PMID: 26091457; PMCID: PMC4616529.

Skolnick et al. "From genes to pro in structure and function: novel applications of computational approaches in the genomic era". Trends Biotechnol, Jan. 2000; 18 (1):34-9, doi: 10.1016/s0167-7799(99)01398-0. PMID: 10631780.

Burgess et al. (J. Cell Biol. 111: 2129-2138, 1990). "Possible Dissociation of the Herapin-binding and Mitogenic Activities of Heparin-binding (Acidic Fibroblast) Growth Factor-1 from Its Receptor-binding Activities be Site-directed Mutagenesis of a Single Lysine Residue". J Cell Biol. Nov. 1990;111(5 Pt 1):2129-38. doi: 10.1083/jcb.111.5.2129. PMID: 1699952; PMCID: PMC2116333.

Miosge et al. "Comparison of predicted and actual consequences of missense mutations" Proc Natl Acad Sci U S A. 2015; 112(37): E5189-98. doi: 10.1073/pnas.1511585112. Epub Aug. 12, 2015. PMID: 26269570; PMCID: PMC4577149.

Bork, Peer. "Powers and pitfalls in sequence analysis: The 70% Hurdle", Genome Research, 2000, 10:398-400. doi: 10.1101/gr.10.4.398. PMID: 10779480.

Warzocha et al., "Antisense Strategy: Biological Utility and Prospects in the Treatment of Hematological Malignancies", Leukemia and Lymphoma (1997) vol. 24. pp. 267-281, doi: 10.3109/10428199709039014. PMID: 9156656.

McKeague et al., "Challenges and Opportunities for Small Molecule Aptamer Development" J Nucleic Acids. 2012;2012:748913, Epub Oct. 24, 2012. doi: 10.1155/2012/748913. Epub Oct. 24, 2012. PMID: 23150810; PMCID: PMC3488411.

Vajdos et al., "Comprehensive Functional Maps of the Antigen-binding Site of an Anti-ErbB2 Antibody Obtained with Shotgun Scanning Mutogenesis", J Mol Biol. Jul. 5, 2022;320(2):415-28. doi: 10.1016/S0022-2836(02)00264-4. PMID: 12079396.

Brown et al., "Tolerance of single, but not multiple, amino acid replacements in antibody VH CDR 2: a means of minimizing B cell wastage from somatic hypermutation?", J Immunol. May 1996; 156(9):3285-91, PMID: 8617951.

Guido et al., "Virtual screening and its integration with modern drug design technologies". Curr Med Chem. 2008;15(1):37-46. doi: 10.2174/092986708783330683. PMID: 18220761.

Clark et al., "Discovery and development of Janus kinase (JAK) inhibitors for inflammatory diseases". J Med Chem. Jun. 26, 2014;57(12):5023-38. doi: 10.1021/jm401490p. Epub Jan. 23, 2014. PMID: 24417533.

Waiker et al., "Imperfect gold standards for kidney injury biomarker evaluation". J Am Soc Nephrol. Jan. 2012;23(1):13-21. doi: 10.1681/ASN.2010111124. Epub Oct. 21, 2011. PMID: 22021710; PMCID: PMC3695762.

Brooks, J.D., "Translational genomics: the challenge of developing cancer biomarkers". Genome Res. Feb. 2012;22(2):183-7. doi: 10.1101/gr.124347.111. PMID: 22301132; PMCID: PMC3266026.

McKean et al., "Biomarkers in Precision Cancer Immunotherapy: Promise and Challenges". Am Soc Clin Oncol Educ Book. May 2020;40:e275-e291. doi: 10.1200/EDBK_280571. PMID: 32453632.

Aberuyi et al., "Drug Resistance Biomarkers and Their Clinical Applications in Childhood Acute Lymphoblastic Leukemia". Front Oncol. Jan. 17, 2020;9:1496. doi: 10.3389/fonc.2019.01496. PMID: 32010613; PMCID: PMC6978753.

Sporn et al., "Chemoprevention of Cancer," Carcinogenesis, vol. 21 (2000) 525-530. doi: 10.1093/carcin/21.3.525. PMID: 10688873.

Auerbach et al., "Angiogenesis assays: problems and pitfalls". Cancer Metastasis Rev. 2000;19(1-2):167-72. doi: 10.1023/a:1026574416001. PMID: 11191056.

Gura, T. "Systems for Identifying New Drugs are Often Faulty", Science, 1997, 278(5340): 1041-1042, DOI: 10.1126/science.278.5340.1041.

HogenEsch et al., "Challenges in pre-clinical testing of anti-cancer drugs in cell culture and in animal models". J Control Release. Dec. 10, 2012;164(2):183-6. doi: 10.1016/j.jconrel.2012.02.031. Epub Mar. 14, 2012. PMID: 22446384; PMCID: PMC3387503.

Winter, Stuart S., (2013) ATP Binding Cassette C1 (ABCC1/MRP1)-mediated drug efflux contributes to disease progression in T-lineage acute lymphoblastic leukemia, Health (Irvine Calf) 5(5A): 41-50.

Wei, Jin, et al. (2017) "MUC1 induces acquired chemoresistance by upregulating ABCB1 in EGFR-dependent manner", Cell Death and Disease 8, e2980, 13 pages.

Pierard, Laure et al. (2017) "Involvement of Angiogenin in Sunitinib Resistance in Human Renal Cell Carcinoma", The Journal of Urology vol. 197, No. 4S, Supplement.

Goncalves, Kevin A., et al. (2016). "Angiogenin Promotes Hematopoietic Regeneration by Dichotomously Regulating Quiescence of Stem and Progenitor Cells", Cell Press 166, 894-906.

Efferth, Thomas, et al. (2006). "Expression profiling of ATP-binding cassette transporters in childhood T-cell acute ymphoblastic leukemia", Molecular Cancer Therapeutics 2006;5(8).

Yamazaki et al.; "Cytokine biomarkers to predict antitumor responses to nivolumab suggested in a phase 2 study for advanced melanoma". Cancer science, 108.5: pp. 1022-1031.(2017).

Dronca et al., "Bim and soluble PD-L1 (sPD-L1) as predictive biomarkers of response to anti-PD-1 therapy in patients with melanoma and lung carcinoma" Journal of Clinical Oncology, 2017, 35 No. 15 suppl, Abstract 11534.

Sanmamed et al., "Serum Interleukin-8 Reflects Tumor Burden and Treatment Response across Malignancies of Multiple Tissue Origins" Clinical Cancer Research, 2014, 20(22): 5697-5707.

Sznol et al., "Survival and long-term follow-up of safety and response in patients (pts) with advanced melanoma (MEL) in a phase I trial of nivolumab (anti-PD-1; BMS-936558; ONO-4538)" Journal of Clinical Oncology, 2013, 31 No. 18 suppl, Abstract CRA9006/\.

Tockman et al., "Considerations in Bringing a Cancer Biomarker to Clinical Application" Cancer Research, 1992, 52:2711s-2718s.

(56) References Cited

OTHER PUBLICATIONS

Choudhary et al. "Interleukin-6 role in head and neck squamous cell carcinoma progression" World Journal of Otorhinolaryngology—Head and Neck Surgery, 2016, 2, pp. 90-97.

Krishnamurthy et al. "Endothelial Interleukin-6 defines the tumorigenic potential of primary human cancer stem cells" Stem Cells, 2014, 32(11): 2845-2857.

Merhi et al. "Squamous Cell Carcinomas of the Head and Neck Cancer Response to Programmed Cell Death Protein-1 Targeting and Differential Expression of Immunological Markers: A Case Report", Frontiers in Immunology, 2018, vol. 9, Article 1769, pp. 1-10.

Lee et al. "Current concepts in the diagnosis and management of cytokine release syndrome," 2014, Blood, vol. 124, No. 2, pp. 188-195.

Rotz et al. "Severe cytokine release syndrome in a patient receiving PD-1-directed therapy" Pediatric Blood & Cancer, 2017, 64: e26642, 5 pages.

Anonymous: "FAM83 Proteins Promote Tumorigenesis and Drug Resistance", Cancer Discovery, 2012, vol. 2, No. 10, 1 page.

Chen et al., Analysis of Immune Signatures in Longitudinal Tumor Samples Yields Insight into Biomarkers of Response and Mechanisms of Resistance to Immune Checkpoint Blockade. Cancer Discovery, 6(8), 827-837, 2016.

Hamid et al., A prospective phase II trial exploring the association between tumor microenvironment biomarkers and clinical activity of ipilimumab in advanced melanoma. Journal of translational medicine, 9.1:204 (2011).

Juric et al., "MMP-9 inhibition promotes anti-tumor immunity through disruption of biochemical and physical barriers to T-cell trafficking to tumors", PLOS ONE 13(11), 2018.

Munoz et al., Highly Efficacious Nontoxic Preclinical Treatment for Advanced Metastatic Breast Cancer Using Combination Oral UFTCyclophosphamide Metronomic Chemotherapy, Cancer Res 2006; 66: (7), 3386-3391, 2006.

Bonfil et al., "Inhibition of human prostate cancer growth, osteolysis and angiogenesis in a bone metastasis model by a novel mechanism-based selective gelatinase inhibitor", Int. J. Cancer: 118, 2721-2726 (2006).

Kruger et al., Antimetastatic Activity of a Novel Mechanism-Based Gelatinase Inhibitor; Cancer Res 2005; 65: (9), 3523-3526, 2005.

Fujiu et al., "A heart-brain-kidney network controls adaptation to cardiac stress through tissue macrophage activation" Nature Medicine, vol. 23, No. 5, 611-622, 2017.

Wang et al. IL-6 mediates platinum-induced enrichment of ovarian cancer stem cells. JCI Insight. Dec. 6, 2018;3(23):e122360. doi: 10.1172/jci.insight.122360. PMID: 30518684; PMCID: PMC6328027.

Cohen et al. Platinum-resistance in ovarian cancer cells is mediated by IL-6 secretion via the increased expression of its target cIAP-2. J Mol Med (Berl). Mar. 2013;91(3):357-68. doi: 10.1007/s00109-012-0946-4. Epub Sep. 28, 2012. PMID: 2305248.

Turano et al. A Potential Role of IL-6/IL-6R in the Development and Management of Colon Cancer. Membranes (Basel). Apr. 24, 2021;11(5):312. doi: 10.3390/membranes11050312. PMID: 33923292; PMCID: PMC8145725.

Chen et al. Siltuximab (CNTO 328): a promising option for human malignancies. Drug Des Devel Ther. Jul. 2, 2015;9:3455-8. doi: 10.2147/DDDT.S86438. PMID: 26170629; PMCID: PMC4494175.

Lin et al. The role of IL-7 in Immunity and Cancer. Anticancer Res. Mar. 2017;37(3):963-967. doi: 10.21873/anticanres.11405. PMID: 28314253.

Kruisbeek, A. M. (1992). In Vivo Depletion of CD4- and CD8- Specific T Cells. Current Protocols in Immunology, 1(1), 4.1.1-4.1.5, 2001.

Tian et al., "A novel cancer vaccine with the ability to simultaneously produce anti-PD-1 antibody and GM-CSF in cancer cells and enhance Th1-biased antitumor immunity" Signal Transduction and Targeted Therapy (2016) 1, 16025.

Lavi et al., "Sustained delivery of IL-1Ra from biodegradable microspheres reduces the number of murine B16 melanoma lung metastases" Journal of Controlled Release, 123, 2007; 123-130.

McMichael et al., "IL-21 Enhances Natural Killer Cell Response to Cetuximab-Coated Pancreatic Tumor Cells" Clinical Cancer Research, 2017, 23(2); 489-502.

Peng et al., "PD-1 Blockade Enhances T-cell Migration to Tumors by Elevating IFN-y Inducible Chemokines" Cancer Research, 2012, 72(20); 5209-5218.

Ragnhammar et al., "Neutralising antibodies to granulocyte-macrophage colony stimulating factor (GM-CSF) in carcinoma patients following GM-CSF combination therapy" 1996, 13; 161-166.

Chen et al. Role of interleukin-6 in the radiation response of liver tumors. Int J Radiat Oncol Biol Phys. Dec. 1, 2012;84(5):e621-30. doi: 10.1016/j.ijrobp.2012.07.2360. Epub Sep. 11, 2012. PMID: 22975618.

Alishekevitz et al., Macrophage-Induced Lymphangiogenesis and Metastasis following Paclitaxel Chemotherapy Is Regulated by VEGFR3. Cell Reports, 17(5), 1344-1356, 2016.

Beyar-Katz et al., Bortezomib-induced pro-inflammatory macrophages as a potential factor limiting anti-tumour efficacy. The Journal of Pathology, 239(3), 262-273, 2016.

Chen et al., Intermittent Metronomic Drug Schedule Is Essential for Activating Antitumor Innate Immunity and Tumor Xenograft Regression. Neoplasia, 16(1), 84-W27, 2014.

De Henau et al., Overcoming resistance to checkpoint blockade therapy by targeting PI3Kγ in myeloid cells. Nature, 539(7629), 443-447, 2016.

De Palma et al., Macrophage Regulation of Tumor Responses to Anticancer Therapies. Cancer Cell, 23(3), 277-286, 2013.

Doloff et al. VEGF Receptor Inhibitors Block the Ability of Metronomically Dosed Cyclophosphamide to Activate Innate Immunity-Induced Tumor Regression. Cancer Research, 72(5), 1103-1115, 2012.

Duraiswamy et al., Dual Blockade of PD-1 and CTLA-4 Combined with Tumor Vaccine Effectively Restores T-Cell Rejection Function in Tumors. Cancer Research, 73(12), 3591-3603, 2013.

Gajewski et al., Innate and adaptive immune cells in the tumor microenvironment. Nature Immunology, 14(10), 1014-1022, 2013.

Giesen et al., Highly multiplexed imaging of tumor tissues with subcellular resolution by mass cytometry. Nature Methods, 11(4), 417-422, 2014.

Gingis-Velitski et al., Host Response to Short-term, Single-Agent Chemotherapy Induces Matrix Metalloproteinase-9 Expression and Accelerates Metastasis in Mice. Cancer Research, 71(22), 6986-6996, 2011.

Hughes et al., Matrigel: A complex protein mixture required for optimal growth of cell culture. Proteomics, 10(9), 1886-1890, 2010.

Kim et al., Assaying Cell Cycle Status Using Flow Cytometry. Current Protocols in Molecular Biology, 111: 28 6 pp. 1-11. (2016).

Kim et al., "Macrophages and mesenchymal stromal cells support survival and proliferation of multiple myeloma cells", British Journal of Haematology; 158(3): pp. 336-346. (2012).

Kodumudi et al., "Immune Checkpoint Blockade to Improve Tumor Infiltrating Lymphocytes for Adoptive Cell Therapy" PloS one 11(4):e0153053. (2016).

Topalian et al., "Immune checkpoint blockade: a common denominator approach to cancer therapy", Cancer Cell. Apr. 13, 2015;27(4):450-61. doi: 10.1016/j.ccell.2015.03.001. Epub Apr. 6, 2015. PMID: 25858804; PMCID: PMC4400238.

Ma et al., "Anticancer Chemotherapy-Induced Intratumoral Recruitment and Differentiation of Antigen-Presenting Cells", Immunity. 38(4): pp. 729-741 (2013).

Makkouk et al., "Cancer Immunotherapy and Breaking Immune Tolerance—New Approaches to an Old Challenge", Cancer Res. 75(1): pp. 5-10 (2015).

Ostrand-Rosenberg et al., "Myeloid-Derived Suppressor Cells: Linking Inflammation and Cancer", J. Immunol. 182(8):4499-4506, 2009.

Pardoll, "The blockade of immune checkpoints in cancer immunotherapy", Nat Rev Cancer. 12(4): 252-264, (2012).

(56) References Cited

OTHER PUBLICATIONS

Postow et al., "Immune Checkpoint Blockade in Cancer Therapy", Journal of Clinical Oncology vol. 33, No. 17, pp. 974-982 (2015).
Qiu et al., "Extracting a Cellular Hierarchy from High-dimensional Cytometry Data with SPADE", Nat Biotechnol. ; 29(10): 886-891, 2011.
Rachman-Tzemah et al., Blocking Surgically Induced Lysyl Oxidase Activity Reduces the Risk of Lung Metastases, Cell Reports; 19(4): pp. 774-784, (2017).
Ran et al., "Double nicking by RNA-guided CRISPR Cas9 for enhanced genome editing specificity", Cell. 12; 154(6):1380-1389, 2013.
Ran et al., "Genome engineering using the CRISPR-Cas9 system", Nat Protoc. 8(11): 2281-2308, 2013.
Romano et al., The therapeutic promise of disrupting the PD-1/PD-L1 immune checkpoint in cancer: unleashing the CD8 T cell mediated anti-tumor activity results in significant, unprecedented clinical efficacy in various solid tumors, Journal for ImmunoTherapy of Cancer 3:15, 2015.
Sato et al., "Interleukin 10 in the tumor microenvironment: a target for anticancer immunotherapy", Immunol Res. 51:170-182, 2011.
Shaked et al., "Antiangiogenic Strategies on Defense: On the Possibility of Blocking Rebounds by the Tumor Vasculature after Chemotherapy", Cancer Res. 67(15): pp. 7055-7058 (2007).
Shaked et al., "Therapy-Induced Acute Recruitment of Circulating Endothelial Progenitor Cells to Tumors", Science. 313(5794):1 pp. 785-787. (2006).
Shaked et al., "Rapid Chemotherapy-Induced Acute Endothelial Progenitor Cell Mobilization: Implications for Antiangiogenic Drugs as Chemosensitizing Agents", Cancer Cell. 14(3): pp. 263-273 (2008).
Sharma, P., Hu-Lieskovan, S., Wargo, J. A., & Ribas, A. (2017). Primary, Adaptive, and Acquired Resistance to Cancer Immunotherapy. Cell, 168(4), 707-723, 2017.
Swart et al., "Combination Approaches with immune-Checkpoint Blockade in Cancer Therapy" Frontiers in Oncology. 6:233 (2016).
Sun et al., "IL-10 and PD-1 cooperate to limit the activity of tumor-specific CD8 + T cells" Cancer Res. 75(8): 1635-1644, 2015.
Timaner et al., "Analysis of the Stromal Cellular Components of the Solid Tumor Microenvironment Using Flow Cytometry" Curr Protoc Cell Biol. 70:19 pp. 81-82 (2016).

* cited by examiner

| Number of processes | Number of patients | 3mo responders | 6mo responders | 1y responders |
|---|---|---|---|---|
| 0 | 62 (33.5%) | 44 (71.0%) | 25 (42.4%) | 14 (25.5%) |
| 1 | 48 (25.9%) | 38 (80.9%) | 32 (68.1%) | 12 (32.4%) |
| 2 | 30 (16.2%) | 19 (63.3%) | 16 (55.2%) | 8 (30.8%) |
| 3 | 21 (11.4%) | 16 (76.2%) | 11 (55.0%) | 3 (20.0%) |
| 4 | 17 (9.2%) | 12 (70.6%) | 8 (50.0%) | 1 (10.0%) |
| 5 | 7 (3.8%) | 7 (100.0%) | 5 (83.3%) | 2 (66.7%) |

CANCER PROCESS EVALUATION

CROSS REFERENCE TO RELATED APPLICATIONS

This application claims the benefit of priority of U.S. Provisional Patent Application No. 63/231,770, filed Aug. 11, 2021, and U.S. Provisional Patent Application No. 63/324,116, filed Mar. 27, 2022, the contents of which are all incorporated herein by reference in their entirety.

FIELD OF INVENTION

The present invention is in the field of computerized cancer process analysis.

BACKGROUND OF THE INVENTION

One of the major complications in oncology is resistance to therapy. Many studies have focused on the involvement of mutations and epigenetic changes in tumor cells in conferring drug resistance. However, in recent years, studies have indicated that in response to almost any type of anti-cancer therapy, the patient (i.e., the host) may generate pro-tumorigenic and pro-metastatic effects. This phenomenon, called host-response, is the physiological reaction of the patient to the cancer therapy that potentially counteracts the anti-tumor activity of the treatment.

Lung cancer displays the highest death rate among the different cancer types, with approximately 2.1 million lung cancer cases and 1.8 million deaths in 2018 worldwide. More than 85% of the lung cancer cases are classified as non-small lung cancer (NSCLC) of which the two most common histological subtypes are lung adenocarcinoma and lung squamous cell carcinoma. The treatment of NSCLC has shifted from the use of mainly chemotherapy to more personalized approaches. Currently, patient-specific genetic alterations in tumor cells determine eligibility for receiving targeted agents. In particular, the status of programmed death ligand-1 (PD-L1) expression levels in the tumor determines eligibility for receiving this immunotherapy.

Immunotherapy is a type of treatment based on immune response modulation. Currently, one of the most common immunotherapy approaches is the use of immune checkpoint inhibitors (ICI), which target regulators of the immune system in order to stimulate it. At present, there are several approved ICIs in the form of monoclonal antibodies targeting the immune checkpoint proteins, CTLA4, PD-1, and PD-L1. ICI treatments are approved for treatment in multiple cancer types, including melanoma and NSCLC.

Several limitations exist for these therapeutic agents when used as monotherapy, with objective responses observed in only 20-30% of patients. Combination therapies have the potential to overcome treatment resistance. However, methods of tailoring the particular second therapy that is best suited for each patient are currently very limited. A new accurate in vitro test for determining the pro-cancer process active in each subject after initiation of therapy, which can then be targeted with specific secondary therapies, is therefore greatly needed.

SUMMARY OF THE INVENTION

The present invention provides methods of selecting a therapeutic agent to treat a cancer in a subject comprising receiving a plurality of protein data element values representing levels of the proteins in a biological sample from the subject, classifying each protein as a member of a process class, for each process class calculating a process score that represents the prominence of the process class to promote cancer treatment resistance in said subject and selecting at least one therapeutic agent that targets a selected process based on the process score. Systems for selecting a therapeutic agent are also provided.

According to a first aspect, there is provided a method of selecting a therapeutic agent to treat a cancer in a subject by at least one processor, the method comprising:

receiving a plurality of protein data element values, each representing the level of a specific protein in a biological sample of the subject;

classifying each protein data element as a member of one or more process classes, wherein each process class represents a specific mechanism of cancer treatment resistance;

for each process class, calculating a first process score based on the member protein data element values, wherein the first process score represents prominence of the respective process class to cancer treatment resistance; and selecting at least one therapeutic agent that targets a selected process class, based on at least one first process score.

According to some embodiments, a process score beyond a predetermined threshold indicates the process is active in the cancer in the subject, and wherein the selected process class is a process class active in the cancer in the subject.

According to some embodiments, the method further comprises producing at least one recommendation data element, representing recommendation for administering the selected at least one therapeutic agent to the subject.

According to some embodiments, the method further comprises administering the selected at least one therapeutic agent to the subject.

According to some embodiments, the cancer is lung cancer, optionally wherein the cancer is non-small cell lung cancer.

According to some embodiments, the biological sample is selected from blood plasma, whole blood, blood serum or peripheral blood mononuclear cells.

According to some embodiments, the biological sample is blood plasma.

According to some embodiments, the plurality of protein data element values comprises element values from at least 80 different proteins.

According to some embodiments, the plurality of protein data element values comprises element values from at least 5000 different proteins.

According to some embodiments, the biological sample is obtained from a subject naïve to treatment and the therapeutic agent is a first line treatment.

According to some embodiments, the biological sample is obtained from the subject after treatment with an immunotherapy and wherein the therapeutic agent is a combination treatment with the immunotherapy.

According to some embodiments, the immunotherapy comprises an immune checkpoint inhibitor (ICI).

According to some embodiments, the immunotherapy comprises administration of an immune checkpoint inhibitory antibody that binds to an immune checkpoint selected from PD-1, PD-L1 and CTLA-4.

According to some embodiments, the method further comprises administering the ICI to the subject and extracting the sample from the subject after the administering.

According to some embodiments, after is at least 24 hours after.

According to some embodiments, the biological sample is obtained from the cancer patient before the administration.

According to some embodiments, the biological sample is obtained from the cancer patient at a time point of about 72 hours or less before the administration with ICI.

According to some embodiments, calculating a first process score of a process class having N member protein data elements comprises:
- normalizing the values of the N member protein data elements according to a common mean value, to produce N corresponding z-score values, each representing a standard deviation distance of a protein data element value from the common mean value;
- calculating an interim score value as a Euclidean distance of an N dimensional vector, whose components are the N z-score values; and
- normalizing the interim score value according to the number N of member protein data elements, to produce the first process score.

According to some embodiments, the method further comprises producing a plurality of pseudo process classes, each comprising a plurality of randomly selected protein data element of the patient;
- for each pseudo process class, calculating a respective process score, to obtain a plurality of second process scores;
- accumulating the plurality of second process scores, to obtain an expected distribution of second process scores in the subject;
- generating a third process score for each process representative of the probability that the first process score would be received based on the expected distribution of the plurality of second process scores in the subject and wherein the selected process is a process with a third process score that is below a predetermined threshold.

According to some embodiments, the predetermined threshold is 5% probability.

According to some embodiments, the method further comprises normalizing the protein data element values of the subject such that the sum of all protein data element values equals a predefined sum value, and wherein calculating the first process score is based on the member protein data elements' normalized values.

According to some embodiments, the process classes comprise inflammation, proliferation, immune modulation, angiogenesis and metabolism.

According to some embodiments, the process class is inflammation and the therapeutic agent is selected from: BMS-986253 (anti-IL-8), BNT411 (TLR7 antagonist), BDC-1001 (anti-HER2 and TLR7/8 agonis conjugate), Tocilizumab (anti-IL-6R), TransCon TLR7/8 Agonist (TLR7/8 agonist), Canakinumab (anti-IL-1 beta), and Pixatimod (TLR9 agonist).

According to some embodiments, the process class is proliferation and the therapeutic agent is selected from: Carboplatin, Pemetrexed, Paclitaxel, Nab-paclitaxel, Cisplatin, Carboplatin, Etoposide, FOLFOX, Datopotamab Deruxtecan (anti-TACSTD2 antibody-drug conjugate), radiotherapy, chemoradiotherapy, Tisotumab vedotin (anti-CD142 antibody-drug conjugate), Vistusertib (mTOR inhibitor), AZD9150 (STAT3 oligonucleotide inhibitor), Tomivosertib (MNK1/2 inhibitor), Sacituzumab Govitecanhziy (SG, anti-TACSTD2 antibody-drug conjugate), Azacitidine+Entinostat (chemotherapy+HDAC inhibitor), brentuximab vedotin (anti-CD30 antibody-drug conjugate), ATE: Trans-arterial Tirapazamine (embolization and chemosensitizing agent), LMB-100 (antibody-Drug Conjugate targeting mesothelin), SAR408701 (Tusamitamab ravtansine, anti-CEACAM5-maytansinoid Antibody-drug Conjugate), Cryosurgical freezing, Non-ablative Cryosurgical freezing, Ipatasertib (AKT inhibitor), RO6958688 (bispecific antibody targeting CEA and CD3), Cobimetinib (MEK inhibitor), Sacituzumab Govitecan (anti-TACSTD2 antibody-drug conjugate), and 6-Thio-2'-Deoxyguanosine (telomere-disrupting compound).

According to some embodiments, the process class is immune modulation and the therapeutic agent is selected from: AZD6738 (ATR kinase inhibitor), Oleclumab (anti-NT5E), Olaparib (PARP inhibitor), CPI-444 (ADORA2A/B antagonist), Lifileucel, LN-145, GSK4428859A (Anti-TIGIT), GSK3359609/Feladilimab (agonstic anti-ICOS), MK-5890 (Anti-CD27 agonist), MK-0482 (LILRB4 signaling inhibitor), MK-4830 (Anti-LILRB2), Domvanalimab or AB154 (Anti-TIGIT), Etrumadenant (ADORA2A/B antagonist), Tiragolumab (anti-TIGIT), Olaparib (PARP inhibitor), Niraparib (PARP inhibitor), Relatlimab (anti-LAG3), Cobolimab (Anti-HAVCR2), Pembrolizumab/Vibostolimab (MK-7684A, Anti-TIGIT), Ociperlimab (Anti-TIGIT), Etrumadenant+Domvanalimab (ADORA2A/B antagonist+anti-TIGIT (alteranative ICI)), SEA-CD40 (Agonistic anti-CD40), Oleclumab (Anti-NT5E), Monalizumab (Anti-KLRC1) and Sitravatinib (Anti-RTKs (receptor tyrosine kinases) including TYRO3, VEGFR2 AXL, MET, FLT3, KIT, FLT1, DDR2, NTRK1, FLT4, EPHA3, PDGFRA, METRK, EPHB6, RET, KDR)).

According to some embodiments, the process class is angiogenesis and the therapeutic agent is selected from: AL3818 (Tyrosine kinase inhibitor), Bevacizumab (anti-VEGFA), Ramucirumab (anti-KDR), Sitravatinib (Tyrosine kinase inhibitor), ATE: Trans-arterial Tirapazamine Embolization, Cabozantinib S-malate (Tyrosine kinase inhibitor), cediranib (Tyrosine kinase inhibitor), Vorolanib (Anti-PDGFRA, PDGFRB, CSF1R, KDR, FLT1, FLT4), Defactinib (Anti-PTK2, PTK2B), Nintedanib (Tyrosine kinase inhibitor), Regorafenib (Tyrosine kinase inhibitor), cabozantinib (Tyrosine kinase inhibitor), Axitinib (Tyrosine kinase inhibitor), and AL3818 or anlotinib (Tyrosine kinase inhibitor).

According to some embodiments, the process class is metabolism and the therapeutic agent is selected from: Linagliptin (DPP4 inhibitor), Metformin (antihyperglycemic agent), Rosiglitazone (PPARs activator), Talabostat (DPP4 inhibitor) and telaglenastat (glutaminase inhibitor).

According to some embodiments, the method further comprises predicting the response of the subject to an immunotherapy.

According to some embodiments, at least one of:
a. if the subject is responsive to the immunotherapy administering to the subject a combined treatment of the immunotherapy and the at least one therapeutic agent;
b. if the subject is non-responsive to the immunotherapy administering to the subject the at least one therapeutic agent instead of the immunotherapy; and
c. if the subject is non-responsive to the immunotherapy administering to the subject a combined treatment of the immunotherapy and the at least one therapeutic agent and determining if the at least one therapeutic agent converts the non-responsive subject to a responsive subject.

According to some embodiments, the predicting the response to the immunotherapy comprises:
a. receiving a plurality of protein data element values
   i. in a population of subjects suffering from cancer and known to respond to the immunotherapy (responders); and
   ii. in a population of subjects suffering from cancer and known to not respond to the therapy (non-responders);
b. calculating for proteins of the plurality of protein data element values a resistance score, where the resistance score is based on the similarity of the protein data element value in the subject to the protein data element value in the responders and the similarity of the protein data element value in the subject to the non-responders; and
c. classifying a protein of the plurality of protein data element values with a resistance score beyond a predetermined threshold as a resistance-associated protein; wherein a subject with a number of resistance-associated proteins above a predetermined number is predicted to be resistant to the therapy and a subject with a number of resistance-associated factors at or below a predetermined number is predicted to respond to the therapy.

According to some embodiments, the predicting the response to the immunotherapy comprises:
a. receiving a plurality of protein data element values
   i. in a population of subjects suffering from cancer and known to respond to the immunotherapy (responders); and
   ii. in a population of subjects suffering from cancer and known to not respond to the therapy (non-responders);
b. calculating for each protein of the plurality of protein data element values a resistance score, where the resistance score is based on the similarity of the protein data element value in the subject to the protein data element value in the responders and the similarity of the protein data element value in the subject to the non-responders;
c. classifying a protein of the plurality of protein data element values with a resistance score beyond a predetermined threshold as a resistance-associated protein;
d. summing the number of resistance-associated proteins present for the subject; and
e. applying a trained machine learning algorithm to the number of resistance-associated proteins and at least one clinical parameter of the subject, wherein the trained machine learning algorithm outputs a final resistance score and a final resistance score beyond a predetermined threshold indicates the subject is resistant to the therapy.

According to some embodiments, the predicting the response to the immunotherapy comprises:
a. receiving a plurality of protein data element values
   i. in a population of subjects suffering from cancer and known to respond to the immunotherapy (responders); and
   ii. in a population of subjects suffering from cancer and known to not respond to the therapy (non-responders);
b. calculating for factors of the plurality of factors a resistance score, where the resistance score is based on the similarity of the factor expression level in the subject to the factor expression level in the responders and the similarity of the factor expression level in the subject to the non-responders and wherein the calculating comprises applying a machine learning algorithm trained on a training set comprising the received factor expression levels in responders and non-responders and the sex of each of the responders and non-responders to individual received factor expression levels from the subject and the subject's sex and wherein the machine learning algorithm outputs the resistance score; and
c. sum the calculated resistance scores to produce a total resistance score; wherein a subject with a number of resistance-associated factors beyond a predetermined threshold is predicted to be resistant to the therapy.

According to some embodiments, the plurality of protein data element values from the subject, the responder and the non-responders are from a sample obtained before administration of the immunotherapy.

According to some embodiments, the method comprises before (b) selecting a subset of the plurality of factors, wherein the subset comprises factors that best differentiate between the responders and non-responders, and wherein the calculating is for each factor of the subset.

According to some embodiments, the selecting comprises applying a Kolmogorov-Smirnov test to the received factor expression levels.

According to some embodiments, the calculating comprises applying a machine learning algorithm trained on a training set comprising the received factor expression levels in responders and non-responders to individual received factor expression levels from the subject and wherein the machine learning algorithm outputs the resistance score.

According to some embodiments, the training set further comprises the sex of each responder and non-responder and the machine learning algorithm is applied to individual received factor expression levels from the subject and the subject's sex.

According to another aspect, there is provided a system for selecting a therapeutic agent to treat a cancer in a subject, the system comprising a non-transitory memory device, wherein modules of instruction code are stored, and at least one processor associated with the memory device, and configured to execute the modules of instruction code, whereupon execution of the modules of instruction code, the at least one processor is configured to:
receive a plurality of protein data element values, each representing levels of a specific protein in a biological sample of the subject;
classify each protein data element as a member of one or more process classes, wherein each process class represents a specific mechanism of cancer treatment resistance;
calculate, for each process class, a first process score based on the member protein data element values, wherein the first process score represents prominence of the respective process class to cancer treatment resistance; and
select at least one therapeutic agent that targets a selected process class, based on at least one first process score.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1A:
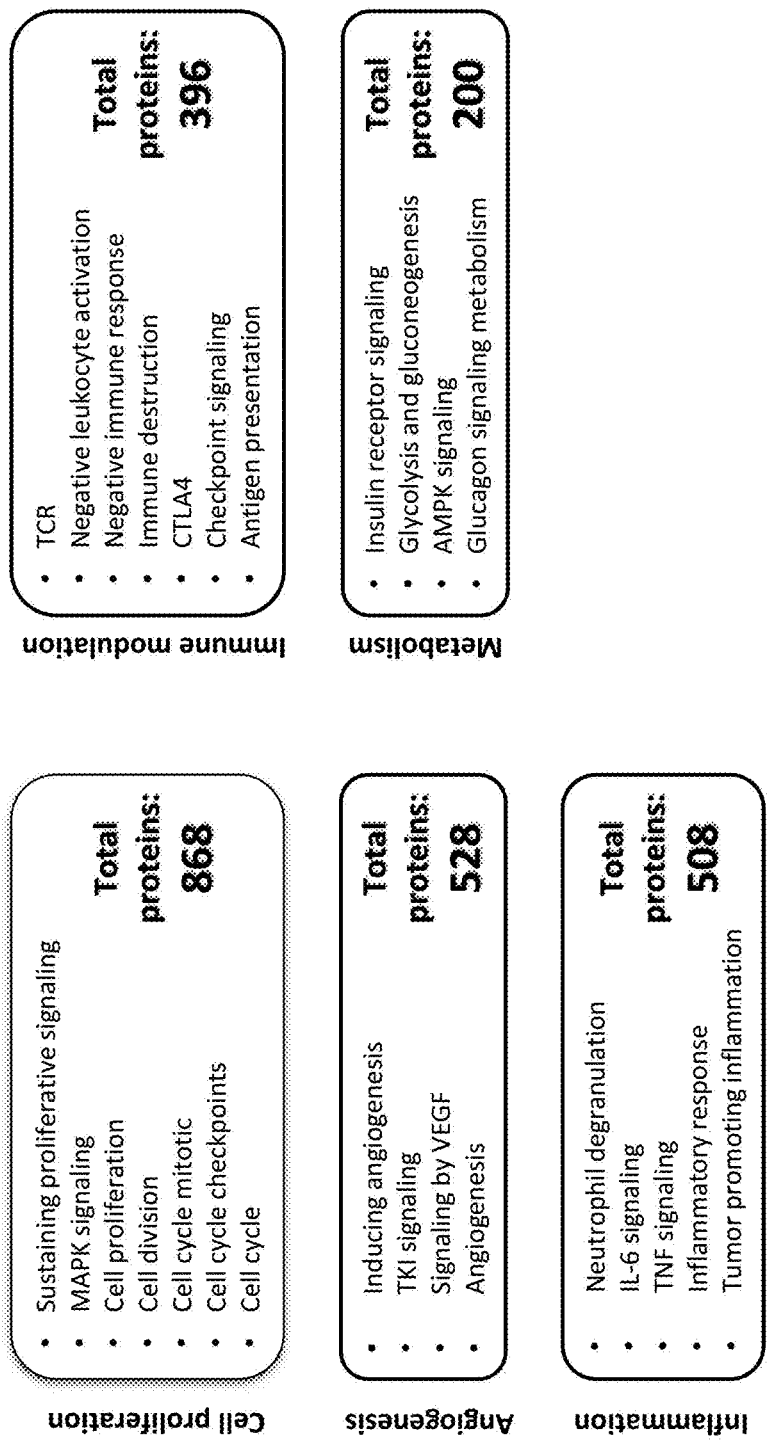
FIGS. 1A-1C: Process construction method. (1A) Five biological processes including cell proliferation, inflammation, immune modulation, angiogenesis and metabolism, that may be associated with resistance to therapy and can be targeted with ICI in combination with another therapy were identified. Each biological process was associated with a protein list obtained from known databases by selecting pathways that were identified by a skilled artisan as falling within the process. These lists underwent manual curation, and the final list of proteins in each biological process was used as an input for the process activation algorithm. The identified pathways are listed along with the total number of proteins in each process. (1B) Ven diagram describing the process protein list intersection. (1C) Heatmap of the Jaccard index of similarity between the processes.

The present invention, in some embodiments, provides computerized methods of determining a process active in a subject suffering from cancer and/or selecting a therapeutic agent to treat cancer in a subject. System for performing the methods of the invention are also provided.

By a first aspect, there is provided a method of identifying a biological process active in a cancer in a subject by at least one processor, the method comprising:
  receiving a plurality of protein data element values;
  classifying each protein data element as a member of one or more process classes 110;
  for each process class 110, calculating a first process score based on the member protein data element values, wherein the first process score represents prominence of the respective process class 110 to the cancer; and
  selecting a process class 110 prominent in the subject based on at least one first process score as a biological process active in the subject;
  thereby identifying a biological process active in a subject.

By another aspect, there is provided a method of selecting a therapeutic agent to treat a cancer in a subject by at least one processor, the method comprising performing a method of the invention to identify a biological process active in the cancer in a subject and selecting at least one therapeutic agent that targets the identified process, thereby selecting a therapeutic agent to treat a cancer.

By another aspect, there is provided a method of selecting a therapeutic agent to treat a cancer in a subject by at least one processor, the method comprising:
  receiving a plurality of protein data element values;
  classifying each protein data element as a member of one or more process classes 110;
  for each process class 110, calculating a first process score based on the member protein data element values, wherein the first process score represents prominence of the respective process class 110 to the cancer in the subject; and
  selecting at least one therapeutic agent that targets a selected process class 110, based on at least one first process score;
thereby selecting a therapeutic agent to treat a cancer.

A method of selecting a therapeutic agent to treat a cancer in a subject by at least one processor, the method comprising:
  receiving a plurality of protein data element values, each representing the level of a specific protein in a biological sample of said subject;
  classifying each protein data element as a member of one or more process classes, wherein each process class represents a specific mechanism of cancer treatment resistance;
  for each process class, calculating a first process score based on the member protein data element values, wherein the first process score represents prominence of the respective process class to cancer treatment resistance; and
  selecting at least one therapeutic agent that targets a selected process class, based on at least one first process score.

In some embodiments, the method is a diagnostic method. In some embodiments, the method is an in vitro method. In some embodiments, the method is an ex vivo method. In some embodiments, the method is a computer implemented method. In some embodiments, the method is a statistical method. In some embodiments, the method is a method that cannot be performed in a human mind. In some embodiments, the method is a computerized method. In some embodiments, the processor is a computer processor. In some embodiments, the processor is a computer.

In some embodiments, the method is a method of predicting a biological process active in a cancer. In some embodiments, the method is a method of predicting the prominence of biological process in a cancer. In some embodiments, the process is a biological process. In some embodiments, a process is a cancer resistance process. In some embodiments, the process represents a specific mechanism of cancer treatment resistance. In some embodiments, a process is a pathway. In some embodiments, prominence is activity. In some embodiments, activity and prominence are proportional. In some embodiments, prominence is relative activity. In some embodiments, the method is a method of predicting the most active biological process in a subject. In some embodiments, in a subject is in a cancer of the subject. In some embodiments, the method is a method of predicting the most active biological process in a cancer. It will be understood by a skilled artisan that the biological process is active generally in the subject and not just in the cancer, however, this general process has a profound effect on the cancer cells. Indeed, processes active in the subject can promote resistance of the cancer to therapeutic treatment. Thus, by establishing the biological processes/pathways active in the subject, a skilled artisan is determining the resistance processes active in or acting on the cancer. In some embodiments, activity is activity in producing cancer survival. In some embodiments, activity is activity in producing cancer resistance. In some embodiments, resistance is resistance to treatment. In some embodiments, resistance is resistance to therapy. In some embodiments, the method is a method of predicting response of a subject to a therapeutic agent that targets a biological process. In some embodiments, the method is a method of selecting a therapeutic agent. In some embodiments, the therapeutic agent is an agent predicted to be effective in a subject. In some embodiments, the therapeutic agent is an agent predicted to be effective in combination with an anticancer therapy in the subject. In some embodiments, the method is a method for determining active process probability. In some embodiments, process probability is a process score. In some embodiments, the score is proportional to the prominence of the process. In some embodiments, the score is proportional to the likelihood the process is active.

In some embodiments, the subject is a mammal. In some embodiments, the subject is a human. In some embodiments, the subject suffers from a disease. In some embodiments, the disease is treatable by the therapy. In some embodiments, the disease is cancer. In some embodiments, the disease is treatable by an immune checkpoint inhibitor (ICI). In some embodiments, the cancer is a PD-L1 positive cancer. In some embodiments, the cancer is a PD-L1 negative cancer. In some embodiments, the cancer is solid cancer. In some embodiments, the cancer is a tumor. In some embodiments, the cancer is selected from hepato-biliary cancer, cervical cancer, urogenital cancer (e.g., urothelial cancer), testicular cancer, prostate cancer, thyroid cancer, ovarian cancer, nervous system cancer, ocular cancer, lung cancer, soft tissue cancer, bone cancer, pancreatic cancer, bladder cancer, skin cancer, intestinal cancer, hepatic cancer, rectal cancer, colorectal cancer, esophageal cancer, gastric cancer, gastroesophageal cancer, breast cancer (e.g., triple negative breast cancer), renal cancer (e.g., renal carcinoma), skin cancer, head and neck cancer, leukemia and lymphoma. In some embodiments, the cancer is selected from skin cancer, and lung cancer. In some embodiments, the cancer is skin cancer. In some embodiments, the cancer is lung cancer. In some embodiments, the skin cancer is melanoma. In some embodiments, the lung cancer is small cell lung cancer. In some embodiments, the lung cancer is non-small cell lung cancer. In some embodiments, the subject is naïve to therapy before the first determining. In some embodiments, the subject has not received the therapy before the first determining. In some embodiments, the subject has received the therapy previously. In some embodiments, the subject has previously been treated by a therapy other than the therapy. In some embodiments, the subject is naïve to any therapy. In some embodiments, the subject is naïve to immunotherapy. In some embodiments, the therapy is the first line of treatment. In some embodiments, the therapy is an advanced line of treatment.

In some embodiments, the protein data element values represent expression of proteins in a sample. In some embodiments, each protein data element value represents the expression of a specific protein in a sample. In some embodiments, the protein data element values represent the levels of the proteins in the sample. In some embodiments, levels are concentrations. In some embodiments, levels are the relative expression of the proteins. In some embodiments, levels are the amounts of the proteins. In some embodiments, the protein data element values represent concentrations of proteins in a sample. In some embodiments, each protein data element value represents the levels of a specific protein in a sample. In some embodiments, each protein data element value represents the concentration of a specific protein in a sample. In some embodiments, the data element values represent amounts of proteins in a sample. In some embodiments, each protein data element value represents the amount of a specific protein in a sample.

In some embodiments, the expression is protein expression. In some embodiments, the expression is secreted protein expression. In some embodiments, protein expression is soluble protein expression. In some embodiment, the expression is cellular protein expression. In some embodiments, the expression is membranal protein expression. In some embodiments, expression is expression level. In some embodiments, expression level is concentration. In some embodiments, concentration is concentration level. It will be understood by a skilled artisan that when the presence of a protein is measured in a liquid sample the expression can be provided as a concentration such as mg/ml or in arbitrary units according to the method of determining the protein's expression. Arbitrary units can be selected from relative fluorescence unit (RFU) and Normalized Protein expression (NPX), or any other arbitrary units used as measurement of expression. It will be understood that the data element values can be any measure that represents the amount/level/concentration of the proteins. The terms "expression" and "expression levels" are used herein interchangeably and refer to the amount of a gene product present in the sample. In some embodiments, the gene product is protein. In some embodiments, gene product includes polynucleotide, e.g., mRNA encoding the protein. In some embodiments, determining comprises quantification of expression levels. In some embodiments, determining comprises normalization of expression levels. Determining of the expression level of the factor can be performed by any method known in the art. Methods of determining protein expression include, for example, antibody arrays, immunoblotting, immunohistochemistry, flow cytometry (FACS), ELISA, proximity extension assay (PEA), aptamer-based assays, proteomics arrays, proteome sequencing, flow cytometry (CyTOF), multiplex assays, mass spectrometry and chromatography. In some embodiments, determining protein expression levels comprises ELISA. In some embodiments, determining protein expression levels comprises protein array hybridization. In some embodiments, determining protein expression levels comprises mass-spectrometry quantification. In some embodiments, determining protein expression levels comprises PEA. In some embodiments, determining protein expression levels comprises aptamers. Methods of determining mRNA expression include, for example, RT-PCR, quantitative PCR, real-time PCR, microarrays, northern blotting, in situ hybridization, next generation sequencing, and massively parallel sequencing.

In some embodiments, a plurality is at least 2, 3, 4, 5, 6, 7, 8, 9, 10, 11, 12, 13, 14, 15, 16, 17, 18, 19, 20, 21, 22, 23, 24, 25, 30, 35, 40, 45, 50, 100, 150, 200, 250, 300, 400, 500, 600, 700, 800, 900, 1000, 1100, 1200, 1300, 1400, 1500, 1600, 1700, 1800, 1900, 2000, 3000, 4000, 5000, 6000, 7000, 8000, 9000, 10000, 12000, 15000, 20000, 25000, 30000, 35000, or 40000. Each possibility represents a separate embodiment of the invention. In some embodiments, protein data element values for at least 60 proteins are received. In some embodiments, protein data element values for at least 80 proteins are received. In some embodiments, protein data element values for at least 100 proteins are received. In some embodiments, protein data element values for at least 200 proteins are received. In some embodiments, protein data element values for at least 400 proteins are received. In some embodiments, protein data element values for at least 1000 proteins are received. In some embodiments, protein data element values for at least 5000 proteins are received. In some embodiments, protein data element values for at least 7000 proteins are received. In some embodiments, protein data element values for at least 8000 proteins are received.

In some embodiments, the sample is from the subject. In some embodiments, the sample is from the subject before receiving a therapy. In some embodiments, the plurality of protein data element values is determined for the subject before receiving a therapy. In some embodiments, the protein data element values are from time T0. In some embodiments, T0 is a time before administration of the therapy. In some embodiments, the sample is provided by the subject before receiving the therapy. In some embodiments, the expression levels are from the subject before receiving a first treatment of the therapy. In some embodiments, a treatment is a dose. In some embodiments, the therapy is an anticancer therapy. In some embodiments, the therapy is an immunotherapy. In some embodiments, the sample is from a subject naïve to treatment and the therapeutic agent is a first-line treatment. In some embodiments, the sample is from a subject after treatment with a therapy and wherein said therapeutic agent is a combination treatment with the therapy.

In some embodiments, the therapy is an anticancer therapy. In some embodiments, the therapy is an immunotherapy. In some embodiments, the immunotherapy is a blocking antibody. In some embodiments, the immunotherapy is administration of a blocking antibody to the subject. In some embodiments, the immunotherapy is an immune checkpoint inhibitor (ICI). In some embodiments, the immunotherapy is immune checkpoint blockade (ICB). In some embodiments, the immunotherapy is immune checkpoint modulator. In some embodiments, the immunotherapy comprises immune checkpoint blockade.

In some embodiments, the immunotherapy is a plurality of immunotherapies. In some embodiments, the immunotherapy is immune checkpoint protein blockade. In some embodiments, the immunotherapy is immune checkpoint protein inhibition. In some embodiments, the immunotherapy is immune checkpoint protein modulation. In some embodiments, the immunotherapy comprises immune checkpoint inhibition. In some embodiments, the immunotherapy comprises immune checkpoint modulation. In some embodiments, the immunotherapy comprises immune checkpoint blockade. In some embodiments, immune checkpoint blockade and/or immune checkpoint inhibition comprises administering to the subject an immune checkpoint inhibitor. In some embodiments, inhibition comprises administering an immune checkpoint inhibitor. In some embodiments, the inhibitor is a blocking antibody. In some embodiments, the immunotherapy comprises immune checkpoint blockade. In some embodiments, modulation comprises administering an immune checkpoint modulator. In some embodiments, immune checkpoint modulation comprises administering to the subject an immune checkpoint modulator.

As used herein, the term "an immune checkpoint inhibitor (ICI)" refers to a single ICI, a combination of ICIs and a combination of an ICI with another cancer therapy. In some embodiments, an ICI is immune checkpoint blockade (ICB). The ICI may be a monoclonal antibody, a humanized antibody, a fully human antibody, a fusion protein or a combination thereof directed to blocking, inhibition or modulation of immune checkpoint proteins. In some embodiments, an immune checkpoint inhibitor is an immune checkpoint modulator. In some embodiments, the immune checkpoint protein is selected from PD-1 (Programmed Death-1); PD-L1; PD-L2; CTLA-4 (Cytotoxic T-Lymphocyte-Associated protein 4); A2AR (Adenosine A2A receptor), also known as ADORA2A; B7-H3, also called CD276; B7-H4, also called VTCN1; B7-H5; BTLA (B and T Lymphocyte Attenuator), also called CD272; IDO (Indoleamine 2,3-dioxygenase); KIR (Killer-cell Immunoglobulin-like Receptor); LAG-3 (Lymphocyte Activation Gene-3); TDO (Tryptophan 2,3-dioxygenase); TIM-3 (T-cell Immunoglobulin domain and Mucin domain 3); VISTA (V-domain Ig suppressor of T cell activation); NOX2 (nicotinamide adenine dinucleotide phosphate NADPH oxidase isoform 2); SIGLEC7 (Sialic acid-binding immunoglobulin-type lectin 7), also called CD328; SIGLEC9 (Sialic acid-binding immunoglobulin-type lectin 9), also called CD329; OX40 (Tumor necrosis factor receptor superfamily, member 4) also called CD134; and TIGIT. In some embodiments, the immune checkpoint protein is selected from PD-1, PD-L1 and PD-L2. In some embodiments, the immune checkpoint protein is selected from PD-1 and PD-L1. In some embodiments, the immune checkpoint protein is selected from PD-1, PD-L1 and CTLA-4. In some embodiments, the immune checkpoint protein is CTLA-4. In some embodiments, the immune checkpoint protein is PD-1. In some embodiments, the immune checkpoint protein is PD-L1. In some embodiments, immune checkpoint blockade comprises an anti-PD-1/PD-L1/PD-L2 immunotherapy. In some embodiments, immune checkpoint blockade comprises an anti-PD-1 immunotherapy. In some embodiments, immune checkpoint blockade comprises an anti-PD-1 and/or anti-PD-L1 immunotherapy. In some embodiments, immune checkpoint blockade comprises an anti CTLA-4 immunotherapy. In some embodiments, immune checkpoint blockade comprises an anti-PD-1 and/or anti-PD-L1 immunotherapy and an anti CTLA-4 immunotherapy.

In some embodiments, the ICI is a monoclonal antibody (mAb) against PD-1 or PD-L1. In some embodiments, the ICI is a mAb that neutralizes/blocks/inhibits/modulates the PD-1 pathway process. In some embodiments, the ICI is a mAb against PD-1. In some embodiments, the anti-PD-1 mAb is Pembrolizumab (Keytruda; formerly called lambrolizumab). In some embodiments, the anti-PD-1 mAb is Nivolumab (Opdivo). In some embodiments, the anti-PD-1 mAb is Pidilizumab (CT0011). In some embodiments, the anti-PD-1 mAb is Cemiplimab (Libtayo, REGN2810). In some embodiments the anti-PD-1 is Dostarlimab. In some embodiments the anti-PD-1 is Camrelizumab. In some embodiments the anti-PD-1 is Zimberelimab. In some embodiments, the anti-PD-1 mAb is any one of AMP-224, MEDI0680, or PDR001. In some embodiments, the ICI is a mAb against PD-L1. In some embodiments, the anti-PD-L1 mAb is selected from Atezolizumab (Tecentriq), Avelumab (Bavencio), and Durvalumab (Imfinzi). In some embodiments, the anti-PD-L1 mAb is Atezolizumab. In some embodiments, the anti-PD-L1 mAb is Durvalumab. In some embodiments, the ICI is a mAb against CTLA-4. In some embodiments, the anti-CTLA-4 mAb is ipilimumab.

In some embodiments, the sample is from the subject before receiving a therapy. In some embodiments, before is at least 1 hour, 2 hours, 3 hours, 6 hours, 8 hours, 12 hours, 1 day, 2 days, 3 days, 5 days, 1 week, 2 weeks, 3 weeks, 4 weeks or 1 month before the therapy or before administration of the therapy. Each possibility represents a separate embodiment of the invention. In some embodiments, before is 5 weeks, 6 weeks, 7 weeks, 8 weeks, 9 weeks or 10 weeks before administration of the therapy. Each possibility represents a separate embodiment of the invention. In some embodiments, before is at least 1 hour before. In some embodiments, before is just before the therapy or before administration of the therapy. In some embodiments, before is at most 1 hour, 2 hours, 3 hours, 4 hours, 6 hours, 9 hours, 12 hours, 18 hours, 24 hours, 2 days, 3 days, 5 days, 1 week, 2 weeks, 3 weeks, 4 weeks or 1 month before the therapy or before administration of the therapy. Each possibility represents a separate embodiment of the invention. In some embodiments, before is at most 5 weeks, 6 weeks, 7 weeks, 8 weeks, 9 weeks or 10 weeks before the therapy or before administration of the therapy. Each possibility represents a separate embodiment of the invention. In some embodiments, before is at most 24 hours before the therapy or before administration of the therapy. In some embodiments, administration of the therapy is the first administration of the therapy.

In some embodiments, the sample is from the subject after receiving a therapy. In some embodiments, the protein data element values are from time T1. In some embodiments, T1 is a time after administration of the therapy. In some embodiments, the sample is provided by the subject after receiving the therapy. In some embodiments, the sample is from the subject after receiving a first treatment of the therapy. In some embodiments, the sample is from a subject naïve to the therapy, after receiving a first treatment of the therapy. In some embodiments, sample is from the subject after receiving any treatment with the therapy.

In some embodiments, after is at a time after initiation of the therapy, or after administration of the therapy, sufficient for altered expression of the at least one factor. In some embodiments, after is at a time after initiation of the therapy, or after administration of the first treatment of the therapy. In some embodiments, after is at least 1 day, 2 days, 3 days, 4 days, 5 days, 6 days, 1 week, 2 weeks, 3 weeks, 4 weeks, 6 weeks, 1 month, 2 months, 3 months, 4 months, 5 months, 6 months, or a year after. Each possibility represents a separate embodiment of the invention. In some embodiments, after is at least 24 hours after. In some embodiments, after is at least 2 weeks after. In some embodiments, after is at least 3 weeks after. In some embodiments, after is at least 4 weeks after. In some embodiments, after is at least 6 weeks after. In some embodiments, after is at least 8 weeks after. In some embodiments, after is at most 1 week, 2 weeks, 3 weeks, 4 weeks, 6 weeks, 1 month, 2 months, 3 months, 4 months, 5 months, 6 months or a year after initiation of the therapy, or after administration of the therapy. Each possibility represents a separate embodiment of the invention.

In some embodiments, the method further comprises administering the anticancer therapy to the subject before the receiving. In some embodiments, the method further comprises administering the anticancer therapy to the subject and obtaining the sample. In some embodiments, obtaining is extracting. In some embodiments, the obtaining is after the administering. In some embodiments, the method further comprises administering the anticancer therapy to the subject after the receiving protein data element values. In some embodiments, the method comprises obtaining the sample and then administering the anticancer therapy to the subject. In some embodiments, the obtaining is before the administering.

In some embodiments, the receiving protein data element values is determining protein data element values. In some embodiments, determining is measuring. In some embodiments, the measuring is in a sample. In some embodiments, the protein data element values were detected in a sample.

In some embodiments, the determining is directly in the sample. In some embodiments, the determining is in the unprocessed sample. In some embodiments, the determining is in a processed sample. In some embodiments, the method further comprises processing the sample. In some embodiments, processing comprises isolating proteins from the sample. In some embodiments, processing comprises isolating nucleic acids from the sample. In some embodiments, the nucleic acid is RNA. In some embodiments, the RNA is mRNA. In some embodiments, the processing comprises lysing cells in the sample.

As used herein, the terms "peptide", "polypeptide" and "protein" are used interchangeably to refer to a polymer of amino acid residues. In another embodiment, the terms "peptide", "polypeptide" and "protein" as used herein encompass native peptides, peptidomimetics (typically including non-peptide bonds or other synthetic modifications) and the peptide analogues peptoids and semipeptoids or any combination thereof. In another embodiment, the peptides polypeptides and proteins described have modifications rendering them more stable while in the body or more capable of penetrating into cells. In one embodiment, the terms "peptide", "polypeptide" and "protein" apply to naturally occurring amino acid polymers. In another embodiment, the terms "peptide", "polypeptide" and "protein" apply to amino acid polymers in which one or more amino acid residue is an artificial chemical analogue of a corresponding naturally occurring amino acid.

In some embodiments, the sample is a biological sample. In some embodiments, the sample is tissue. In some embodiments, the tissue is cancer tissue. In some embodiments, the tissue is tumor. In some embodiments, the sample is a fluid. In some embodiments, the fluid is a biological fluid. In some embodiments, the sample is from the subject. In some embodiments, the sample is not a tumor sample. In some embodiments, the sample is a tumor sample. In some embodiments, the cancer is not a hematopoietic cancer and the sample is a blood sample. In some embodiments, the sample is a sample that does not comprise cancer cells. In some embodiments, a blood sample comprises a peripheral blood sample and a plasma sample. In some embodiments, the sample is a plasma sample. In some embodiments, the sample is serum. In some embodiments, processing comprises isolating plasma. In some embodiments, processing comprises isolating serum. In some embodiments, the biological fluid is selected from, blood, plasma, serum, lymph, cerebral spinal fluid, urine, feces, semen, tumor fluid and gastric fluid. In some embodiments, the sample obtained from the subject and the responders are the same type of sample. In some embodiments, the sample is selected from peripheral blood, plasma, serum and peripheral blood mononuclear cells (PBMCs). In some embodiments, the sample is selected from whole blood, blood plasma, blood serum and PBMCs. In some embodiments, the sample is not PBMCs. In some embodiments, the sample does not comprise PBMCs.

In some embodiments, a process is a biological process. In some embodiments, the process is a process class. In some embodiments, a process is a cancer survival process. In some embodiments, a process is a resistance-associated process. In some embodiments, resistance is cancer resistance. In some embodiments, resistance is resistance to therapy. In some embodiments, a process is a mechanism. In some embodiments, a process is a pathway. In some embodiments, a process is made up of the proteins involved in the process, pathway, mechanism or resistance. In some embodiments, a process is made up of the pathways. In some embodiments, the process is selected from proliferation, inflammation, immune modulation, angiogenesis and metabolism. In some embodiments, the process is selected from proliferation, inflammation, immune modulation, and angiogenesis. In some embodiments, the process is proliferation. In some embodiments, the process is inflammation. In some embodiments, the process is immune modulation. In some embodiments, the process is angiogenesis. In some embodiments, the process is metabolism. In some embodiments, the classifying is into at least 2 processes. In some embodiments, the classifying is into at least 2 process classes. In some embodiments, the classifying is into at least 3 processes or process classes. In some embodiments, the classifying is into at least 4 processes or process classes. In some embodiments, the classifying is into at least 5 processes or process classes. In some embodiments, the classifying is into the following processes/process classes: proliferation, inflammation, immune modulation, angiogenesis and metabolism.

In some embodiments, the proteins contained in a process are determined from those known in the art. In some embodiments, the proteins contained in a process are determined from at least one database. In some embodiments, at least one database is at least 2, 3, 4, 5, 6, 7, 8, 9 or 10 databases. Each possibility represents a separate embodiment of the invention. Examples of process databases include, but are not limited to Gene Ontology Resource, Wiki processes, Reactome, CellChat, Ingenuity process Analysis, and Biocarta, although any database in the art may be used. In some embodiments, a protein is included in more than one process.

In some embodiments, prominence to the cancer is prominence to promote treatment resistance. In some embodiments, treatment resistance is cancer treatment resistance. In some embodiments, treatment resistance is immunotherapy resistance. In some embodiments, to the cancer is to the cancer's survival. In some embodiments, to the cancer is to the cancer's resistance. In some embodiments, resistance is treatment resistance. In some embodiments, prominence is importance. In some embodiments, prominence is contribution to the cancer. In some embodiments, prominence is activity in the cancer. In some embodiments, prominence is activity in the subject. In some embodiments, prominence is contribution to cancer treatment resistance. In some embodiments, prominence beyond a predetermined threshold indicates the process is active. In some embodiments, a process score beyond a predetermined threshold indicates the process is active. In some embodiments, the score is a probability. In some embodiments, the score is between zero and 1. In some embodiments, active is active in the cancer. In some embodiments, active is active in the subject. In some embodiments, beyond a threshold is below a threshold. In some embodiments, beyond a threshold is above a threshold. In some embodiments, the predetermined threshold is 0.5, 0.4, 0.3, 0.25, 0.2, 0.15, 0.1, 0.05, 0.01, 0.005, 0.001, 0.0005 or 0.0001. Each possibility represents a separate embodiment of the invention. In some embodiments, the threshold is 0.05. In some embodiments, the threshold is 5%.

In some embodiments, the therapeutic agent targets a selected process class 110. In some embodiments, the therapeutic agent targets the most prominent process class 110. In some embodiments, the selected process class 110 is the most prominent process class 110. In some embodiments, a selected process class 110 is a process class 110 with a score beyond the predetermined threshold. In some embodiments, a selected process class 110 is a process class 110 active in the cancer. In some embodiments, a selected process class 110 is a process class 110 active in the subject. In some embodiments, no process class 110 is active in the cancer. In some embodiments, no process class 110 is active in the subject. In some embodiments, all process classes are active in the cancer. In some embodiments, all process classes are active in the subject. In some embodiments, 1-4 process classes 110 are active in the cancer. In some embodiments, 1-4 process classes 110 are active in the subject. In some embodiments, 0-4 processes classes are active in the cancer. In some embodiments, 0-4 processes classes are active in the subject.

In some embodiments, the method further comprises producing at least one recommendation data element. In some embodiments, the method further comprises producing at least one recommendation. In some embodiments, the data element represents a recommendation for administering the selected at least one therapeutic agent to the subject. In some embodiments, the data element represents a recommendation for administering selected at least one therapeutic agent to the subject to inhibit the active process classes. In some embodiments, the data element represents a recommendation for a clinical trial. In some embodiments, the clinical trial comprises testing the administration of the at least one therapeutic agent. In some embodiments, the clinical trial comprises testing the combined administration of the at least one therapeutic agent and the anticancer therapy. In some embodiments, the method further comprises administering the at least one therapeutic agent to the subject. In some embodiments, the method further comprises administering the at least one therapeutic agent in combination with the anticancer therapy. In some embodiments, in combination is before, after or concomitantly with. In some embodiments, combination is in a single dose composition or in two different compositions.

As used herein, the terms "administering," "administration," and like terms refer to any method which, in sound medical practice, delivers a composition containing an active agent to a subject in such a manner as to provide a therapeutic effect. One aspect of the present subject matter provides for intravenous administration of a therapeutically effective amount of a composition of the present subject matter to a patient in need thereof. Other suitable routes of administration can include parenteral, subcutaneous, oral, intramuscular, intrathecal, intracranial, intratumoral or intraperitoneal. In some embodiments, the administration is systemic administration.

The dosage administered will be dependent upon the age, health, and weight of the recipient, kind of concurrent treatment, if any, frequency of treatment, and the nature of the effect desired.

In some embodiments, the process class 110 has N member protein data elements. In some embodiments, the process class 110 has N member proteins. In some embodiments, calculating a first process score comprises normalizing the values of the N member protein data elements according to a common mean value. In some embodiments, the normalizing produces N corresponding z-score 122A values. In some embodiments, a z-score 122A value represents a standard deviation distance from a mean value. In some embodiments, the mean value is common to all members. In some embodiments, a z-score 122A value represents a standard deviation distance of a protein data element value from the common mean value. In some embodiments, calculating a first process score comprises calculating an interim score value as a Euclidean distance 124A of an N dimensional vector. In some embodiments, the N dimensional vector comprises components that are the N z-score 122A values. In some embodiments, the N dimensional vector consists of components that are the N z-score 122A values. In some embodiments, the N dimensional vector consists of the N z-score 122A values. In some embodiments, calculating a first process score comprises normalizing the interim score value according to the number N of member protein data elements to produce a first process score.

In some embodiments, the method further comprises producing a plurality of pseudo process classes 111. In some embodiments, each pseudo process class 111 comprises a plurality of randomly selected protein data elements. In some embodiments, each pseudo process class 111 comprises a number of randomly selected protein data elements having the same number of protein data elements in the process. In some embodiments, the method further comprises randomly selected is randomly selected from the subject's protein data elements. In some embodiments, the pseudo process classes 111 represent the null hypothesis. In some embodiments, for each pseudo process class 111, calculating a respective process score. In some embodiments, the process score is calculated in the same manner as the first process score. In some embodiments, the respective process score is a pseudo process score. In some embodiments, the pseudo process score is a first pseudo process score. In some embodiments, the respective process score is a first process score. In some embodiments, a plurality of pseudo process scores is obtained. In some embodiments, a pseudo process score is a second process score. In some embodiments, the method further comprises accumulating the plurality of pseudo process scores to obtain an expected distribution of pseudo process scores in the subject. In some embodiments, the expected distribution is the null hypothesis. In some embodiments, the method further comprises generating a third process score for each process. In some embodiments, the third process score is representative of the probability that the first process score would be received based on the expected distribution of the plurality of pseudo process scores in the subject. In some embodiments, the third process score is representative of the probability that the first process score would be received based on the null hypothesis. In some embodiments, the selected process is a process with a third process score that is beyond a predetermined threshold. In some embodiments, the selected process is a process with a third process score that is below a predetermined threshold. In some embodiments, the method further comprises selecting a process with a third process score below a predetermined threshold. In some embodiments, a selected process is a process active in the patient and contribute to treatment resistance. In some embodiments, a selected process is a process active in the cancer. In some embodiments, the threshold is 5% probability. In some embodiments, the threshold is 0.05.

In some embodiments, the method further comprises normalizing the protein data element values of the subject. In some embodiments, the normalizing is such that the sum of all protein data element values equals a predefined sum value. In some embodiments, the predefined sum value is 1. In some embodiments, the calculating the first process score is based on the member protein data elements' normalized values.

In some embodiments, the therapeutic agent targets a selected process. In some embodiments, the therapeutic agent targets a protein from a selected process. In some embodiments, the therapeutic agent targets a pathway from a selected process. In some embodiments, the protein from the selected process is a protein that contributes to the activity of the process in the subject. In some embodiments, the protein from the selected process is the protein that most contributes to the activity of the process in the subject. In some embodiments, the protein from the selected process is the protein that most contributes to the resistance to therapy in the cancer. In some embodiments, the protein from the selected process is the protein that most contributes to the resistance to therapy in the patient. In some embodiments, targets is binds to. In some embodiments, targets is blocks. In some embodiments, blocks is inhibits.

In some embodiments, the process is inflammation and the therapeutic agent is an anti-inflammatory agent. In some embodiments, the process is inflammation and the therapeutic agent targets a protein selected from IL-8, IL-6R, TLR7, TLR8, TLR9, HER2, IL-1B, and CXCL8. In some embodiments, process class is inflammation, and the therapeutic agent is selected from: BMS-986253 (anti-IL-8), BNT411 (TLR7 antagonist), BDC-1001 (anti-HER2 and TLR7/8 agonist conjugate), Tocilizumab (anti-IL-6R), TransCon TLR7/8 Agonist (TLR7/8 agonist), Canakinumab (anti-IL-1 beta), and Pixatimod (TLR9 agonist).

In some embodiments, the process is proliferation, and the therapeutic agent is an anti-proliferative agent. In some embodiments, the anti-proliferative agent is a chemotherapy. In some embodiments, the anti-proliferative agent is radio-therapy. In some embodiments, the anti-proliferative agent is cryoablation. In some embodiments, the process is proliferation and the therapeutic agent targets a protein selected from HDACs, EGF, EGFR, CDA, DNMTs, Mtor, STAT3, AKT, KRAS, MAPK, TACSTD2, CEACAM5, MSLN, GPER1, ERBBW, EPHA2, RAS, PIK3R, KDM1A and PTPN11. In some embodiments, the process class is proliferation and the therapeutic agent is selected from: Carboplatin, Pemetrexed, Paclitaxel, Nab-paclitaxel, Cisplatin, Carboplatin, Etoposide, FOLFOX, Datopotamab Deruxtecan (anti-TACSTD2 antibody-drug conjugate), radiotherapy, chemoradiotherapy, Stereotactic radiation, Tisotumab vedotin (anti-CD142 antibody-drug conjugate), Vistusertib (mTOR inhibitor), AZD9150 (STAT3 oligonucleotide inhibitor), Tomivosertib (MNK1/2 inhibitor), Sacituzumab Govitecan-hziy (SG, anti-TACSTD2 antibody-drug conjugate), Azacitidine+Entinostat (chemotherapy+HDAC inhibitor), brentuximab vedotin (anti-CD30 antibody-drug conjugate), ATE: Trans-arterial Tirapazamine (embolization and chemosensitizing agent), LMB-100 (antibody-Drug Conjugate targeting mesothelin), SAR408701 (Tusamitamab ravtansine, anti-CEACAM5-maytansinoid Antibody-drug Conjugate), Cryosurgical freezing, Non-ablative Cryosurgical freezing, Ipatasertib (AKT inhibitor), RO6958688 (bispecific antibody targeting CEA and CD3), Cobimetinib (MEK inhibitor), Sacituzumab Govitecan (anti-TACSTD2 antibody-drug conjugate), and 6-Thio-2'-Deoxyguanosine (telomere-disrupting compound).

In some embodiments, the process is immunomodulation and the therapeutic agent is an immune modulator. In some embodiments, the immune modulator is an ICI. In some embodiments, the therapeutic agent and the therapy are not the same treatment. In some embodiments, the process is immunomodulation and the therapeutic agent targets a protein selected from TIGIT, HAVCR2, LAG3, NT5E, ADORA2A, ADORA2B, IDO1, ICOS, CTLA4, KLRC1, TNFRSF9, TNFRSF1B, GITR, CD27, NECTIN4, PCSK9, SIGLEC15, LILRB2, and PARP/ATR. In some embodiments, the process is immunomodulation and the therapeutic agent targets a protein selected from ATR, NT5E, PARP, ADORA2A/B, TIGIT, ICOS, CD27, LILRB4, LILRB2, PARP, LAG3, HAVCR2, CD40, and KLRC1. In some embodiments, the immune modulator is an anticancer vaccine. In some embodiments, the immune modulator is adoptive cell transfer. In some embodiments, the transfer cells are T cells. In some embodiments, the adoptive cells are dendritic cells (DCs). In some embodiments, the adoptive cells are natural killer (NK) cells. In some embodiments, the adoptive cells are CAR cells. In some embodiments, the adoptive cells are autologous to the subject. In some embodiments, the process class is immune modulation and the therapeutic agent is selected from: AZD6738 (ATR kinase inhibitor), Apatinib Mesylate (Anti-KDR), Oleclumab (anti-NT5E), CPI-444 (ADORA2A/B antagonist), Lifileucel, LN-145, GSK4428859A (Anti-TIGIT), GSK3359609/Feladilimab (agonstic anti-ICOS), MK-5890 (Anti-CD27 agonist), MK-0482 (LILRB4 signaling inhibitor), MK-4830 (Anti-LILRB2), Domvanalimab (Anti-TIGIT), Etrumadenant (ADORA2A/B antagonist), Tiragolumab (anti-TIGIT), Olaparib (PARP inhibitor), Niraparib (PARP inhibitor), Tiragolumab (Anti-TIGIT), Relatlimab (anti-LAG3), Cobolimab (Anti-HAVCR2), Pembrolizumab/Vibostolimab (MK-7684A, Anti-TIGIT), Ociperlimab (Anti-TIGIT), Etrumadenant+Domvanalimab (ADORA2A/B antagonist+anti-TIGIT (alteranative ICI)), SEA-CD40 (Agonistic anti-CD40), Oleclumab (Anti-NT5E), Monalizumab (Anti-KLRC1), and Sitravatinib (Anti-RTKs (receptor tyrosine kinase, including TYRO3, VEGFR2 AXL, MET, FLT3, KIT, FLT1, DDR2, NTRK1, FLT4, EPHA3, PDGFRA, METRK, EPHB6, RET, KDR).

In some embodiments, the process is angiogenesis and the therapeutic agent is an anti-angiogenic agent. In some embodiments, the process is angiogenesis and the therapeutic agent is a tyrosine kinase inhibitor. In some embodiments, the process is angiogenesis and the therapeutic agent targets a protein selected from VEGF, AXL, MET, FLT3, KIT, FLT1, DDR2, NTRK1, FLT4, EPHA3, PDGFRA, METRK, EPHB6, RET, FGFR1, FGFR2, FGFR3, KDR, bFGF, FGF-2 and VEGFR (VEGFR1, VEGFR3). In some embodiments, VEGF is VEGFA. In some embodiments, the process is angiogenesis and the therapeutic agent targets a protein selected from VEGFA and KDR. In some embodiments, the process class is angiogenesis and the therapeutic agent is selected from: IL3818 (Tyrosine kinase inhibitor), Bevacizumab (anti-VEGFA), Ramucirumab (anti-KDR), Sitravatinib (Tyrosine kinase inhibitor), ATE: Trans-arterial Tirapazamine Embolization, Cabozantinib S-malate (Tyrosine kinase inhibitor), cediranib (Tyrosine kinase inhibitor), Anlotinib hydrochloride (Anti-VEGFR1, VEGFR3, VEGFR2/KDR, PDGFR-α, c-Kit, FGFR1, FGFR2, FGFR3), Endostar (Anti-bFGF,FGF-2,VEGF), Famitinib (RTK), Lenvatinib (Tyrosine kinase inhibitor), Vorolanib (Anti-PDGFRA, PDGFRB, CSF1R, KDR, FLT1, FLT4), Defactinib (Anti-PTK2, PTK2B), Nintedanib (Tyrosine kinase inhibitor), Regorafenib (Tyrosine kinase inhibitor), cabozantinib (Tyrosine kinase inhibitor), Axitinib (Tyrosine kinase inhibitor), and AL3818 or anlotinib (Tyrosine kinase inhibitor).

In some embodiments, the process is metabolism and the therapeutic agent is a metabolism modulator. In some embodiments, the metabolism modulator is a antihyperglycemic agent. In some embodiments, the process is angiogenesis and the therapeutic agent targets a protein selected from DPP4, and PPAR. In some embodiments, the process class is metabolism and the therapeutic agent is selected from: Linagliptin (DPP4 inhibitor), Metformin (antihyperglycemic agent), Rosiglitazone (PPARs activator), Talabostat (DPP4 inhibitor), and telaglenastat (glutaminase inhibitor).

In some embodiments, the method further comprises predicting the response of the subject to a therapy. In some embodiments, the therapy is an immunotherapy. In some embodiments, the predicting is before the process selection. In some embodiments, the predicting is before the therapeutic agent selection. In some embodiments, if the subject is responsive to the therapy the method further comprises administering to the subject a combined treatment comprising the therapy and the at least one therapeutic agent. In some embodiments, if the subject is non-responsive to the therapy the method further comprises administering to the subject the at least one therapeutic agent instead of the therapy. In some embodiments, if the subject is non-responsive to the therapy the method further comprises administering to the subject a combined treatment of the therapy and the at least one therapeutic agent. In some embodiments, the at least one therapeutic agent converts a non-responsive subject to a responsive subject. In some embodiments, the method further comprises determining if the at least one therapeutic agent converts the non-responsive subject to a responsive subject.

In some embodiments, predicting response of a subject to a therapy comprises:
a. receiving expression levels for a plurality of proteins
   i. in a population of subjects known to respond to the therapy (responders); and
   ii. in a population of subjects known to not respond to the therapy (non-responders);
b. calculating for at least one protein of the plurality of proteins a resistance score; and
c. classifying a protein with a resistance score beyond a threshold as a resistance-associated protein;
wherein a subject with a number of resistance-associated proteins beyond a predetermined number is predicted to be resistant to the therapy.

In some embodiments, predicting response of a subject to a therapy comprises:
a. receiving expression levels for a plurality of proteins
   i. in a population of subject known to respond to the therapy (responders); and
   ii. in a population of subject known to not respond to the therapy (non-responders);
b. calculating for at least one protein of the plurality of proteins a resistance score;
c. classify a protein with a resistance score beyond a threshold as a resistance-associated protein;
d. sum the number resistance-associated proteins; and
e. apply a trained machine learning algorithm to the number of resistance-associated proteins and at least one clinical parameter, wherein the trained machine learning algorithm outputs a final resistance score and a final resistance score beyond a predetermined threshold indicates the subject is resistant to the therapy.

In some embodiments, predicting response of a subject to a therapy comprises:
a. receiving expression levels for a plurality of proteins
   i. in a population of subject known to respond to the therapy (responders); and
   ii. in a population of subject known to not respond to the therapy (non-responders);
b. calculate for factors of said plurality of factors a resistance score, where said resistance score is based on the similarity of said factor expression level in said subject to the factor expression level in said responders and the similarity of said factor expression level in said subject to said non-responders; and c. sum said calculated resistance scores to produce a total resistance score; wherein a subject with a total resistance score beyond a predetermined threshold is predicted to be resistant to said therapy.

In some embodiments, resistance is determined by a method of the invention. In some embodiments, non-response comprises progressive disease. In some embodiments, non-response comprises cancer progression. In some embodiments, non-response comprises stable disease. In some embodiments, non-response comprises a worsening of symptoms of the disease. In some embodiments, non-response is not the development of side effects. In some embodiments, non-response comprises growth, metastasis and/or continued proliferation of a cancer. In some embodiments, response is stable disease. In some embodiments, response comprises the development of side effects. In some embodiments, response comprises remission. In some embodiments, remission is minimal remission. In some embodiments, remission is partial remission. In some embodiments, remission is complete remission. In some embodiments, response is measured using the overall response rate (ORR). In some embodiments, response is measured using Response Evaluation Criteria in Solid Tumors 1.1 (RECIST 1.1) or any other method known in the art. In some embodiments, response is measured using method of assessment including CT, PET-CT, and MIII scans. A trained physician will be familiar with methods of determining response and specifically the ORR. In some embodiments, response comprises survival. In some embodiments, survival is overall survival. In some embodiments, survival is progression free survival. In some embodiments, response comprises a durable clinical benefit (DCB).

In some embodiments, the population of responders suffers from the disease. In some embodiments, the responders all have the same disease. In some embodiments, the population of non-responders suffers from the disease. In some embodiments, the non-responders all suffer from the same disease. In some embodiments, the population of responders and non-responders all suffer from the same disease. In some embodiments, the population of responders and the subject suffer from the same disease. In some embodiments, the population of non-responders and the subject suffer from the same disease. In some embodiments, the population of non-responders, the population of responders and the subject suffer from the same disease.

As used herein, the term "responder" or a subject "known to respond" are used interchangeably and refer to a subject that when administered a therapy displays an improvement in at least one criteria of the disease being treated by the therapy or does not show an increase in severity of the disease. In some embodiments, a responder is a subject that when administered a therapy displays an improvement in the disease that is being treated by the therapy. In some embodiments, a responder is a subject that when administered a therapy does not show an increase in severity of the disease. In some embodiments, an increase is severity is over time. In some embodiments, does not show an increase in severity is stable disease. In some embodiments, a responder is a subject that when administered a therapy show mixed response. In some embodiments, a responder is a subject that when administered a therapy show mixed response, wherein mixed response is improvement in at least one criteria of the disease but does not show an improvement in other criteria of the disease. In some embodiments, mixed response is shrinkage of some lesions in combination with growth of new or existing lesions. In some embodiments, a responder is a subject for which the therapy produces an anti-disease response. In some embodiments, for a subject with cancer, a responder is a subject in which the therapy produces an anticancer response. In some embodiments, a response is not a reduction in side effects. In some embodiments, a response is a reduction in side effects. In some embodiments, a response is a response against the disease itself. In some embodiments, an anticancer response is an antitumor response. In some embodiments, an antitumor response comprises tumor regression. In some embodiments, an antitumor response comprises tumor shrinkage. In some embodiments, an antitumor response comprises a lack of tumor growth. In some embodiments, an antitumor response comprises a lack of tumor metastasis. In some embodiments, an antitumor response comprises a lack of tumor hyperproliferation. In some embodiments, an improvement is in at least one symptom of the disease. In some embodiments, response is complete response. In some embodiments, response is partial response. In some embodiments, response comprises stable disease. In some embodiments, responder is a subject with a favorable response to the therapy. In some embodiments, non-responder is a subject with a non-favorable response to the therapy. In some embodiments, a non-favorable response is an increase in tumor burden. Increases in tumor burden can encompass any increase in tumor size or total cancer cell number such as increase in tumor size, increase in tumor spread, increase in metastasis, increase in tumor cell proliferation or any other increase.

As used herein, a "favorable response" of the cancer patient indicates "responsiveness" of the cancer patient to the treatment with the therapy, namely, the treatment of the responsive cancer patient with the therapy will lead to the desired clinical outcome such as tumor regression, tumor shrinkage or tumor necrosis; an anti-tumor response by the immune system; preventing or delaying tumor recurrence, tumor growth or tumor metastasis. In some embodiments, the subject is complete responder or treatment with the cancer therapy leads to stable disease. In some embodiments, a complete responder is a subject in which there is an absence of detectable cancer. In this case, it is possible and advised to continue the treatment of the responsive cancer patient with the therapy or if the patient is cancer free to discontinue treatment. In some embodiments, the method further comprises continuing to administer the therapy to a subject that is not a non-responder. In some embodiments, the subject is non-responder, a minimal responder, partial responder or has a stable disease, and the method further comprises continuing to administer the therapy to a subject, as well as treating the subject with an additional therapy (e.g., determined using the analysis provided herein) to increase responsiveness. In some embodiments, a subject that is not a non-responder is a responder.

As used herein, the term "non-responder" and a subject "known to not respond" are used interchangeably and refer to a subject that when administered a therapy displays no improvement or stabilization in disease. In some embodiments, a non-responder displays a worsening of disease when administered a therapy. In some embodiments, non-responder is not a subject that experiences a side effect of the therapy. In some embodiments, a non-responder is a subject in which the disease progresses. In some embodiments, a non-responder is a subject in which the disease does not stabilize after therapy. In some embodiments, a non-responder is a subject in which the disease does not improve after therapy. In some embodiments, a non-responder is a subject that is not a responder as defined hereinabove. In some embodiments, a non-responder is a subject with a non-favorable response to the therapy. In some embodiments, a non-responder is a subject resistant to the therapy. In some embodiments, a non-responder is a subject refractory to the therapy.

As used herein a "non-favorable response" of the cancer patient indicates "non-responsiveness" of the cancer patient to the treatment with the therapy and thus the treatment of the non-responsive cancer patient with the therapy will not lead to the desired clinical outcome, and potentially to a non-desired outcomes such as tumor expansion, recurrence, or metastases. In some embodiments, the method further comprises discontinuing administration of the therapy to a subject that is a non-responder. In some embodiments the method further comprises continuing to administer the therapy to a subject, in combination with an additional therapy. In some embodiments, the additional therapy increases responsiveness of a non-responsive patient.

In some embodiments, the method is for determining whether the response is considered a durable response (e.g., a progression-free survival of more than 6 months).

In some embodiments, a resistance score is a RAP score. In some embodiments, a resistance score is a response score. In some embodiments, a RAP score is a total RAP score. In some embodiments, the resistance score is based on similarity of the factor expression level in the subject to the factor expression level in the non-responders. In some embodiments, the resistance score is based on similarity of the factor expression level in the subject to the factor expression level in the responders. In some embodiments, based on is calculated based on. In some embodiments, similarity is lack of similarity. In some embodiments, similarity to responders is lack of similarity to non-responders. In some embodiments, similarity to non-responders is lack of similarity to responders. In some embodiments, similarity is measured on a scale. In some embodiments, the scale is from 0 to 1, wherein 1 is perfectly similar to non-responders and 0 is perfectly similar to responders. In some embodiments, the resistance score is from 0 to 1, wherein 1 is perfectly similar to non-responders and 0 is perfectly similar to responders. In some embodiments, the resistance score is based on similarity of the factor expression level in the subject to the factor expression level in the non-responders and the factor expression level in the responders.

In some embodiments, the method comprises before step (b) selecting a subset of factor. In some embodiments, before step (b) is before the calculating. In some embodiments, the subset is a subject of the plurality of factors. In some embodiments, the subject comprises the factors that best differentiate between the responders and non-responders. In some embodiments, the factors that best differentiation are the top percentage. In some embodiments, the top percentage is the top 1, 3, 5, 10, 15, 20, 25, 30, 35, 40, 45 or 50% of factors. Each possibility represents a separate embodiment of the invention. In some embodiments, the top percentage is the top 20%. In some embodiments, the top factors are the top 10, 20, 25, 30, 40, 50, 60, 70, 75, 80, 90 or 100 factors. Each possibility represents a separate embodiment of the invention. In some embodiments, the top factors are the top 50 factors. In some embodiments, selection comprises applying a statistical test. In some embodiments, the statistical test is a Kolmogorov-Smirnov test. In some embodiments, selection comprises applying a Kolmogorov-Smirnov test. In some embodiments, the Kolmogorov-Smirnov test is applied to the received factor expression levels. In some embodiments, the Kolmogorov-Smirnov test determines how well a factor differentiates between responders and non-responders. In some embodiments, the Kolmogorov-Smirnov test outputs a measure of how well a factor differentiates and the best factors are the factors with the highest scores. In some embodiments, selection comprises applying an XGBoost algorithm. In some embodiments, the calculating is for the subset. In some embodiments, the calculating is for each factor of the subset.

In some embodiments, calculating comprises applying a machine learning algorithm. In some embodiments, calculating comprises applying a machine learning model. In some embodiments, the machine learning model is a machine learning algorithm. In some embodiments, the machine learning model implements a machine learning algorithm. In some embodiments, the algorithm is a classifier. In some embodiments, the algorithm is a regression model. In some embodiments, the algorithm is supervised. In some embodiments, the algorithm is unsupervised. In some embodiments, the machine learning algorithm is trained on the expression levels in responders. In some embodiments, the machine learning algorithm is trained on the expression levels in non-responders. In some embodiments, the machine learning algorithm is trained on the expression levels in responders and non-responders. In some embodiments, the machine learning algorithm is trained on a training set. In some embodiments, the machine learning algorithm is trained by a method of the invention. In some embodiments, a machine learning algorithm is applied to factors of the plurality of factors. In some embodiments, a machine learning algorithm is applied to each factor of the plurality of factors. In some embodiments, a machine learning algorithm is applied to the subset. In some embodiments, a machine learning algorithm is applied to the subset of factors. In some embodiments, a machine learning algorithm is applied to each factor of the subset of factors. In some embodiments, each factor is analyzed and calculated separately, and the machine learning algorithm does not use expression levels of more than one factor as the training set. In some embodiments, a trained machine learning algorithm is applied to individual protein expression levels from the subject. In some embodiments, a machine learning algorithm trained on expression levels of a specific factor in responders and non-responders is applied to the expression level of that specific factor in the subject. It will be understood by a skilled artisan, that for each of the factors of the plurality of factors, a different algorithm will be trained and then applied to each expression level of the subject. Thus, if three algorithms are separately trained on expression in responders and non-responders for Factor A, Factor B and Factor C, then the algorithm trained on Factor A expression levels will be applied to the subject's expression level of Factor A, the algorithm trained on Factor B expression levels will be applied to the subject's expression level of Factor B, and the algorithm trained on Factor C expression levels will be applied to the subject's expression level of Factor C. In some embodiments, during a training phase, the machine learning model is trained on a training set comprising expression data for a single factor from responders and non-responders, using corresponding annotations of "responder" or "non-responder" to predict or classify factor expression data according to classes "responder" and "non-responder". In some embodiments, during an inference stage, the machine learning model is applied to expression data of the single factor from a subject to predict classification of the factor as similar to a responder or non-responder. In some embodiments, the classification is a resistance score. In some embodiments, the classification is a response score. In some embodiments, the classification is a measure of how similar the factor is to non-responders and dissimilar to responders.

In some embodiments, the trained machine learning algorithm is trained to predict responsiveness of subjects suffering from the disease to the therapy. In some embodiments, the trained machine learning algorithm is trained to output a resistance score. In some embodiments, the trained machine learning algorithm is trained to output a resistance probability. In some embodiments, the trained machine learning algorithm is trained to output an activity score. In some embodiments, the trained machine learning algorithm is trained to predict activity of a resistance-associated factor in a subject. In some embodiments, the trained machine learning algorithm is trained to predict if a factor is a resistance-associated factor in the subject. In some embodiments, the trained machine learning algorithm is trained to predict if a factor of the subject is a resistance-associated factor in the subject.

In some embodiments, the training set comprises received protein expression levels. In some embodiments, the training set comprises received protein expression levels in both responders and non-responders. In some embodiments, the training set comprises received protein expression levels for only one protein. In some embodiments, the training set comprises the number of resistance-associated proteins expressed in samples. In some embodiments, the sample are from subjects suffering from the disease. In some embodiments, the sample are from responders. In some embodiments, the sample are from non-responders. In some embodiments, the training set comprises at least one clinical parameter. In some embodiments, the clinical parameter is from subjects. In some embodiments, subjects are responders and non-responders. In some embodiments, the training set comprises labels. In some embodiments, the labels are associated with the responsiveness of the subjects. In some embodiments, the resistance-associated proteins are labeled with the labels. In some embodiments, the at least one clinical parameter is labeled with the label.

According to some embodiments, the training set further comprises at least one clinical parameter of each responder and non-responder and the machine learning algorithm is applied to individual received factor expression levels from the subject and the subject's at least one clinical parameter. In some embodiments, the at least one clinical parameter is the sex of the subjects. In some embodiments, the training set further comprises the sex of the subjects. In some embodiments, the subjects are each subject. In some embodiments, sex is gender. In some embodiments, the at least one clinical parameter is sex. In some embodiments, sex is a subject's sex. In some embodiments, sex is male or female. In some embodiments, sex is sex at birth. In some embodiments, the clinical parameter is age. In some embodiments, age is a subject's age. In some embodiments, the clinical parameter is the line of treatment. In some embodiments, the line of treatment parameter is whether the therapy was a first line of treatment or an advanced treatment. In some embodiments, a line of treatment is first line treatment. In some embodiments, a line of treatment is a secondary treatment. In some embodiments, secondary treatment is an advanced treatment. It will be understood by a skilled artisan that advanced treatment may be any line of treatment after the first, e.g., second line, third line, fourth line, fifth line, etc. In some embodiments, the clinical parameter is whether the treatment is a first line treatment or an advanced treatment. In some embodiments, the clinical parameter is PD-L1 status. In some embodiments, PD-L1 status is PD-L1 status of the cancer. Methods of measuring PD-L1 levels in cancer cells (e.g., a tumor) are well known in the art and any such method may be employed. In some embodiments, PD-L1 status comprises high PD-L1 or low PD-L1. In some embodiments, PD-L1 status comprises high PD-L1, low PD-L1 or no PD-L1. In some embodiments, PD-L1 status comprises high PD-L1, medium PD-L1 or low PD-L1. In some embodiments, PD-L1 status comprises PD-L1 expression in less than 1% of cancer cells, in 1-49% of cancer cells, or in 50% or more of cancer cells. In some embodiments, PD-L1 expression in less than 1% of cancer cells is no PD-L1 expression. In some embodiments, PD-L1 expression in less than 1% of cancer cells is low PD-L1 expression. In some embodiments, PD-L1 expression in 1-49% of cancer cells is low PD-L1 expression. In some embodiments, PD-L1 expression in 1-49% of cancer cells is medium PD-L1 expression. In some embodiments, PD-L1 expression in 50% or more of cancer cells is high PD-L1 expression.

In some embodiments, the clinical parameter is a known biomarker of the disease or mutations in known biomarkers of the disease. In some embodiments, the biomarker is selected from MYC, NOTCH, EGFR, HER2, BRAF, KRAS, MAP2K1, MET, NRAS, NTRK1, NTRK2, NTRK3, PIK3CA, RET, ROS1, TP53, ALK, CDKN2A, KIT, NF1, BFAST, FGFR, LDH, PTEN, RB1, PD-L1, MSI (Microsatelite Instability), TMB (Tumor Mutational Burden), or a combination thereof. In some embodiments, the clinical parameter is expression of the biomarker. In some embodiments, expression is percent expression. In some embodiments, expression is mutational status.

In some embodiments, the training set further comprises the sex, age and PD-L1 status of each responder and non-responder. In some embodiments, the training set further comprises the sex of each responder and non-responder. In some embodiments, the training set further comprises the age and PD-L1 status of each responder and non-responder. In some embodiments, the machine learning algorithm is applied to individual received factor expression levels from the subject and the subject's sex. In some embodiments, the machine learning algorithm is applied to individual received factor expression levels from the subject and the subject's sex, age and PD-L1 status. In some embodiments, the calculating comprises applying a machine learning algorithm trained on a training set comprising the received factor expression levels in responders and non-responders and at least one clinical parameter, to the expression levels from the subject and the subject's at least one clinical parameter and wherein the machine learning algorithm outputs the resistance score. In some embodiments, the training comprises the received factor expression levels in responders and non-responders and clinical parameters of each responder and non-responder and the machine learning algorithm is applied to individual received factor expression levels from the subject and the subject's clinical parameters and wherein the machine learning algorithm outputs response prediction. In some embodiments, the training comprises the received factor expression levels in responders and non-responders and a clinical parameter selected from sex, age and PD-L1 expression, or any combination thereof, of each responder and non-responder and the machine learning algorithm is applied to individual received factor expression levels from the subject and the subject's clinical parameters and wherein the machine learning algorithm outputs response prediction. In some embodiments, the training set comprises the number of resistance associated factors in each responder and non-responder and at least one clinical parameter and the machine learning algorithm is applied to the number of resistance associated factors from the subject and the subject's at least one clinical parameters and wherein the machine learning algorithm outputs a response prediction. In some embodiments, the training set comprises the number of resistance associated factors in each responder and non-responder and sex of each responder and non-responder and the machine learning algorithm is applied to the number of resistance associated factors from the subject and the subject's sex and wherein the machine learning algorithm outputs a response prediction. In some embodiments, the training set comprises the number of resistance associated factors in each responder and non-responder, age and PD-L1 status of each responder and non-responder and the machine learning algorithm is applied to the number of resistance associated factors from the subject and the subject's age and PD-L1 status and wherein the machine learning algorithm outputs a response prediction.

In some embodiments, the clinical parameter is the type of treatment. In some embodiments, the clinical parameter is expression of a target of the therapy. In some embodiments, the clinical parameter is expression of a protein within a process that is a target of the therapy. In some embodiments, the process is a process comprising the target of the therapy. In some embodiments, expression is expression in the subject. In some embodiments, expression is expression in a diseased tissue. In some embodiments, expression is expression in a diseased tissue sample. In some embodiments, expression is expression in the tumor. In some embodiments, expression is expression in a tumor sample. In some embodiments, a tumor sample is a biopsy. In some embodiments, expression is expression not in the tumor. In some embodiments, expression is expression not in a tumor sample. In some embodiments, expression is expression in a liquid biopsy. In some embodiments, expression is percent expression. In some embodiments, percent is percent of cells. In some embodiments, the therapy is anti-PD-1 therapy and the protein in the process is PD-L1. In some embodiments, the therapy is anti-PD-L1 therapy, and the target protein is PD-L1. In some embodiments, the clinical parameter is PD-L1 expression. In some embodiments the training set comprises at least one clinical parameter selected from line of treatment, PD-L1 expression, sex and age. In some embodiments the training set comprises protein expression levels and sex. In some embodiments the training set comprises number of RAPs, age and PD-L1 status.

Additionally clinical parameters may also be included. A skilled artisan will be able to select relevant clinical parameters for inclusion in the training set. Examples of additional clinical parameters include, but are not limited to, histological type of the sample (e.g., adenocarcinoma, squamous cell carcinoma, etc.), metastatic location, tumor location, cancer staging (such as tumor, nodes and metastases, TNM, staging for example), performance status (such as ECOG performance status), genetic mutations, epigenetic status, general medical history, vital signs, blood measurements, renal and liver function, weight, height, pulse, blood pressure and smoking history.

In some embodiments, at an inference stage the trained machine learning algorithm is applied. In some embodiments, the trained machine learning algorithm is applied to individual received protein expression levels and the at least one clinical parameter. In some embodiments, the trained machine learning algorithm is applied to individual received protein expression levels from the subjects and the subject's sex. In some embodiments, the trained machine learning algorithm is applied to the number of resistance-associated proteins. In some embodiments, the trained machine learning algorithm is applied to the number of resistance-associated proteins and at least one clinical parameter.

In some embodiments, at the inference stage an input is received. In some embodiments, the input comprises the number of resistance-associated proteins expressed in a sample. In some embodiments, the sample is from a subject. In some embodiments, the input comprises at least one clinical parameter. In some embodiments, the subject suffers from the disease. In some embodiments, the subject has unknown responsiveness to the therapy. In some embodiments, the parameter is of the subject with unknown responsiveness. In some embodiments, at the inference stage the trained machine learning algorithm is applied. In some embodiments, applied is applied to the input. In some embodiments, the input is the received input. In some embodiments, the inference stage is to predict responsiveness. In some embodiments, responsiveness is responsiveness to the therapy of the subject with unknown responsiveness.

In some embodiments, the machine learning algorithm outputs the resistance score. In some embodiments, the resistance score is the RAP score. In some embodiments, the outputted resistance score is scaled from 0 to 1. In some embodiments, 1 is perfectly similar to non-responders and 0 is perfectly similar to responders. In some embodiments, the machine learning algorithm calculates similarity to responders. In some embodiments, the machine learning algorithm calculates similarity to non-responders. In some embodiments, the machine learning algorithm outputs a numeric value of similarity to responders and non-responders. In some embodiments, a protein is considered to be a RAP if its resistance score is beyond a certain threshold. In some embodiments, the threshold for the resistance score is calculated on a scale of 0 to 1. In some embodiments, the threshold for the resistance score of a certain protein is between 0.2 and 0.95. In some embodiments, the threshold for the resistance score of a certain protein is about 0.01, 0.05, 0.1, 0.15, 0.2, 0.25, 0.3, 0.35, 0.4, 0.42, 0.45, 0.5, 0.55, 0.6, 0.65, 0.7, 0.75, 0.8, 0.85, 0.9, or 0.95. Each possibility represents a separate embodiment of the invention. In some embodiments, the threshold for the resistance score is 0.25. In some embodiments, the threshold for the resistance score is 0.42. In some embodiments, the threshold for the resistance score is 0.6. In some embodiments, the threshold for the resistance score when calculated by a machine learning algorithm is about 0.2, 0.25, 0.3, 0.35, 0.4, 0.42, 0.45, 0.5, 0.55, 0.6, 0.65, 0.7, 0.75, 0.8, 0.85, 0.9, or 0.95. Each possibility represents a separate embodiment of the invention. In some embodiments, the threshold for the resistance score when calculated with a machine learning algorithm is 0.25. In some embodiments, the threshold for the resistance score when calculated with a machine learning algorithm is 0.42. In some embodiments, the threshold for the resistance score when calculated with a machine learning algorithm is 0.6.

In some embodiments, response probability is determined by the calculation (1-resistance score). In some embodiments, 1-resistance score is 1-final resistance score. In some embodiments, the resistance score is the final resistance score. In some embodiments, response probability is a response score. In some embodiments, the machine learning algorithm outputs the response score. In some embodiments, the outputted response score is scaled from 0 to 1. In some embodiments, 1 is perfectly similar to responders and 0 is perfectly similar to non-responders. In some embodiments, the machine learning algorithm calculates similarity to responders. In some embodiments, the machine learning algorithm calculates similarity to non-responders. In some embodiments, the machine learning algorithm outputs a numeric value of similarity to responders and non-responders. In some embodiments, a protein is considered to be a RAP if its response score is beyond a certain threshold. In some embodiments, beyond is above. In some embodiments, beyond is below. In some embodiments, the threshold for the response score is calculated on a scale of 0 to 1. In some embodiments, the threshold for the response score of a certain protein is between 0.2 and 0.95. In some embodiments, the threshold for the response score of a certain protein is about 0.2, 0.25, 0.3, 0.35, 0.4, 0.42, 0.45, 0.5, 0.55, 0.6, 0.65, 0.7, 0.75, 0.8, 0.85, 0.9, or 0.95. Each possibility represents a separate embodiment of the invention. In some embodiments, the threshold for the response score is 0.25. In some embodiments, the threshold for the response score is 0.42. In some embodiments, the threshold for the response score is 0.6. In some embodiments, the threshold for the response score when calculated by a machine learning algorithm is about 0.2, 0.25, 0.3, 0.35, 0.4, 0.42, 0.45, 0.5, 0.55, 0.6, 0.65, 0.7, 0.75, 0.8, 0.85, 0.9, or 0.95. Each possibility represents a separate embodiment of the invention. In some embodiments, the threshold for the response score when calculated with a machine learning algorithm is 0.25. In some embodiments, the threshold for the response score when calculated with a machine learning algorithm is 0.42. In some embodiments, the threshold for the response score when calculated with a machine learning algorithm is 0.6.

In some embodiments, response probability is determined by the calculation (1—resistance score). In some embodiments, 1—resistance score is 1—final resistance score. In some embodiments, the resistance score is the final resistance score. In some embodiments, response probability is a response score. In some embodiments, the machine learning algorithm outputs the response score. In some embodiments, the outputted response score is scaled from 0 to 1. In some embodiments, 1 is perfectly similar to responders and 0 is perfectly similar to non-responders. In some embodiments, the machine learning algorithm calculates similarity to responders. In some embodiments, the machine learning algorithm calculates similarity to non-responders. In some embodiments, the machine learning algorithm outputs a numeric value of similarity to responders and non-responders. In some embodiments, a protein is considered to be a RAP if its response score is beyond a certain threshold. In some embodiments, the threshold for the response score is calculated on a scale of 0 to 1. In some embodiments, the threshold for the response score of a certain protein is between 0.2 and 0.95. In some embodiments, the threshold for the response score of a certain protein is about 0.2, 0.25, 0.3, 0.35, 0.4, 0.42, 0.45, 0.5, 0.55, 0.6, 0.65, 0.7, 0.75, 0.8, 0.85, 0.9, or 0.95. Each possibility represents a separate embodiment of the invention. In some embodiments, the threshold for the response score is 0.25. In some embodiments, the threshold for the response score is 0.42. In some embodiments, the threshold for the response score is 0.6. In some embodiments, the threshold for the response score when calculated by a machine learning algorithm is about 0.2, 0.25, 0.3, 0.35, 0.4, 0.42, 0.45, 0.5, 0.55, 0.6, 0.65, 0.7, 0.75, 0.8, 0.85, 0.9, or 0.95. Each possibility represents a separate embodiment of the invention. In some embodiments, the threshold for the response score when calculated with a machine learning algorithm is 0.25. In some embodiments, the threshold for the response score when calculated with a machine learning algorithm is 0.42. In some embodiments, the threshold for the response score when calculated with a machine learning algorithm is 0.6. In some embodiments, the algorithm outputs response probability, and the response probability is calculated on a scale of 0 to 1. In some embodiments, the algorithm outputs response probability, and the response probability is calculated on a scale of 0% to 100%, wherein 100% is responder and 0% is non-responder.

In some embodiments, the score is between zero and 1. In some embodiments, active is active in the cancer. In some embodiments, active is active in the subject. In some embodiments, beyond a threshold is below a threshold. In some embodiments, beyond a threshold is above a threshold. In some embodiments, the predetermined threshold is 0.5, 0.4, 0.3, 0.25, 0.2, 0.15, 0.1, 0.05, 0.01, 0.005, 0.001, 0.0005 or 0.0001. Each possibility represents a separate embodiment of the invention. In some embodiments, the threshold is 0.05. In some embodiments, the threshold is 5%.

In some embodiments, the machine learning model is a machine learning algorithm. In some embodiments, the algorithm is a supervised learning algorithm. In some embodiments, the algorithm is an unsupervised learning algorithm. In some embodiments, the algorithm is a reinforcement learning algorithm. In some embodiments, the machine learning model is a Convolutional Neural Network (CNN). In some embodiments, the at least one hardware processor trains a machine learning model. In some embodiments, the model is based, at least in part, on a training set. In some embodiments, the model is based on a training set. In some embodiments, the model is trained on a training set. In some embodiments, the at least one hardware processor applies the machine learning model to a protein expression level from a subject.

In some embodiments, the calculating comprises calculating a mean expression for each protein in responders. In some embodiments, the calculating comprises calculating a mean expression for each protein in non-responders. In some embodiments, the calculating comprises calculating a mean expression for each protein in responders and a mean expression for each protein in non-responders. In some embodiments, the calculating comprises calculating a distribution of the expression for each protein in responders and non-responders. In some embodiments, the calculating comprises calculating a standard deviation of expression for each protein in responders and non-responders. In some embodiments, in responders is in the responders population. In some embodiments, in non-responders is in the non-responders population. In some embodiments, the resistance score is based on the ratio of deviation of the factor expression in the subject from the calculated mean in responders to the deviation of the factor expression in the subject from the calculated mean in non-responders. Calculation of deviation is well known to one skilled in the art. It will be understood that the more dissimilar the expression in the subject is from a mean the larger the deviation will be. Thus, factors that are very dissimilar to the mean in responders will have a large numerator in the calculation of this ratio and factors that are lowly dissimilar to the mean in non-responders will have a small denominator. Thus, the more dissimilar to responder expression and the more similar to non-responder expression is expression of a factor in a subject the higher the resistance score will be. In some embodiments, a resistance score beyond a predetermined threshold indicates a factor is a resistance-associated factor. In some embodiments, a resistance-associated factor is a resistance-associated protein (RAP).

In some embodiments, the calculating further comprises calculating a distribution for each factor in responders. In some embodiments, the calculating further comprises calculating a distribution for each factor in non-responders. In some embodiments, the calculating further comprises calculating a distribution for each factor in responders and a distribution for each factor in non-responders. In some embodiments, the calculating further comprises calculating a standard deviation for each factor in responders. In some embodiments, the calculating further comprises calculating a standard deviation for each factor in non-responders. In some embodiments, the calculating further comprises calculating a standard deviation for each factor in responders and a standard deviation for each protein in non-responders. In some embodiments, the calculating further comprises calculating a standard deviation for each factor in a mix of responders and non-responders. In some embodiments, the deviation is measured as a multiple of the calculated standard deviation. It will be understood by a skilled artisan that by scaling the deviation to the standard deviation for a group of expression values the deviation can be given in more absolute terms allow for the comparison of factors and populations with very small and very large stand deviations (which may also have very low and very high expression levels).

In some embodiments, the resistance score is based on a Z-score for the expression level of each factor in the subject. In some embodiments, the resistance score is based on the Z-score relative to responders. In some embodiments, the resistance score is based on the Z-score relative to non-responders. In some embodiments, the resistance score is based on both the Z-score relative to responders and the Z-score relative to non-responders. In some embodiments, the resistance score is based on the ratio of the Z-score relative to responders to the Z-score relative to non-responders. It will be well known to a skilled artisan that a Z-score counts the distance of the individual level from the population mean in units of the population standard deviation. In some embodiments, the Z-score is calculated by Equation 1.

In some embodiments, the resistance score is calculated by the equation $$\left(\frac{|z_R|}{|z_{NR}| + c}\right).$$

In some embodiments, $Z_R$ is the deviation of the factor expression in the subject from the calculated mean in responders. In some embodiments, $Z_{NR}$ is the deviation of the factor expression in the subject from the calculated mean in non-responders. In some embodiments, ∥ is the Z-score of the deviation. In some embodiments, ∥ is the standardizing of the deviation to a multiple of the standard deviation. In some embodiments, c is a constant. In some embodiments, constant is a regulation constant that prevents the score from divergence for $Z_{NR}=0$. In some embodiments, the resistance score is calculated by Equation 2. In some embodiments, monotonoic is an ad-hoc function that prevents the resistance score from decreasing for extreme values within the non-responder distributions. In some embodiments, function is the function provided in Algorithm 1.

In some embodiments, a resistance score beyond a predetermined threshold indicates a factor is a RAP. In some embodiments, the threshold is a predetermined threshold. In some embodiments, threshold is a threshold value. In some embodiments, the threshold for the resistance score is about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, or 7.0. Each possibility represents a separate embodiment of the invention. In some embodiments, the threshold is about 0.05, 0.1, 0.15, 0.2, 0.25, 0.3, 0.35, 0.4, 0.45, 0.5, 0.55, 0.6, 0.67, 0.7, 0.75, 0.8, 0.85 or 0.9. Each possibility represents a separate embodiment of the invention. In some embodiments, the threshold for the resistance score is about 2.9. In some embodiments, the threshold for the resistance score is 2.9. In some embodiments, the threshold for the resistance score is about 3.0. In some embodiments, the threshold for the resistance score is 3.0. In some embodiments, the threshold for the resistance score is calculated on a scale of arbitrary units. In some embodiments, the threshold for the resistance score when calculated by a mathematical calculation is about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, or 5.0. Each possibility represents a separate embodiment of the invention. In some embodiments, the threshold for the resistance score when calculated with a mathematical calculation is about 2.9. In some embodiments, the threshold for the resistance score when calculated with a mathematical calculation is 2.9. In some embodiments, the threshold for the resistance score when calculated with a mathematical calculation is about 3.0. In some embodiments, the threshold for the resistance score when calculated with a mathematical calculation is 3.0. In some embodiments, a mathematical calculation is a method that comprises calculating a mean expression for each protein.

In some embodiments, a subject with a number of resistance-associated factors (e.g., RAPs) above a predetermined number is predicted to be resistant to the therapy. In some embodiments, a subject with a number of resistance-associated factors above a predetermined number is predicted to not respond to the therapy. In some embodiments, a subject with a number of resistance-associated factors above a predetermined number is predicted to be a non-responder to the therapy. In some embodiments, a subject with a number of resistance-associated factors below a predetermined number is predicted to be suitable to the therapy. In some embodiments, a subject with a number of resistance-associated factors below a predetermined number is predicted to respond to the therapy. In some embodiments, a subject with a number of resistance-associated factors below a predetermined number is predicted to be a responder to the therapy. In some embodiments, a subject with a number of resistance-associated factors at or below a predetermined number is predicted to be suitable to the therapy. In some embodiments, a subject with a number of resistance-associated factors at or below a predetermined number is predicted to respond to the therapy. In some embodiments, a subject with a number of resistance-associated factors at or below a predetermined number is predicted to be a responder to the therapy.

In some embodiments, the predetermined number is a threshold number. In some embodiments, the predetermined number is 2, 3, 4, 5, 6, 7, 8, 9, 10, 11, 12, 13, 14, 15, 16, 17, 18, 19 or 20. Each possibility represents a separate embodiment of the invention. In some embodiments, the predetermined number is 3. In some embodiments, the predetermined number is 4. In some embodiments, the predetermined number is 7. In some embodiments, the predetermined number is 13.

By another aspect there is provided, a computer program product comprising a non-transitory computer-readable storage medium having program code embodied thereon, the program code executable by at least one hardware processor to perform a method of the invention.

The present invention may be a system, a method, and/or a computer program product. The computer program product may include a computer readable storage medium (or media) having computer readable program instructions thereon for causing a processor to carry out aspects of the present invention.

The computer readable program instructions 5 may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

As used herein, the term "about" when combined with a value refers to plus and minus 10% of the reference value. For example, a length of about 1000 nanometers (nm) refers to a length of 1000 nm+−100 nm.

It is noted that as used herein and in the appended claims, the singular forms "a," "an," and "the" include plural referents unless the context clearly dictates otherwise. Thus, for example, reference to "a polynucleotide" includes a plurality of such polynucleotides and reference to "the polypeptide" includes reference to one or more polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Various embodiments and aspects of the present invention as delineated hereinabove and as claimed in the claims section below find experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Strategies for Protein Purification and Characterization—A Laboratory Course Manual" CSHL Press (1996); all of which are incorporated by reference. Other general references are provided throughout this document.

Materials and Methods

Resistance Associated Proteins (RAPs): A resistance associated protein (RAP) refers to a specific protein whose expression in a given patient confers resistance to therapy, i.e., RAPs are patient specific. A protein is considered to be a RAP when its expression level in the respective patient is more similar to its expression distribution in the non-responder population than to the responder population. RAPs can be determined in a variety of ways. Provided herein is a mathematical calculation of RAPs as well as a machine learning algorithm for classifying RAPs. These methods are merely exemplary and any method of calculating RAPs may be employed.

Mathematical calculation: To put the above concept into quantitative terms, a RAP score (i.e., a resistance score) was determined for each protein. A low RAP score value represents an expression level which is typical to the responder population, and a high RAP score indicates an expression level which is typical to the non-responder population. A protein is considered a RAP in cases where its RAP score is beyond a certain threshold. The RAP score threshold optimization process is described hereinbelow.

The RAP score calculation requires knowing the expression level distribution of each protein in both responder and non-responder populations, and data on the protein level expression of the tested patient. To allow comparison between several different proteins at different ranges of expression level, it is important that the RAP score will not be affected by and sensitive to the protein level expression scale. This is especially important in plasma samples, where there is a large dynamic range of 11 orders of magnitude in protein expression levels. To achieve this, the RAP score is based on Z-score, which counts the distance of the individual level from the population mean in units of the population standard deviation. In technical terms, Z-score is defined by Equation 1.

$$Z = \frac{x - \mu}{\sigma} \quad \text{Equation 1}$$

where x is the protein level in the tested patient, μ is the mean protein level in the population, and σ is the population standard deviation. The Z-score of a given patient is calculated separately with respect to the responders and non-responders populations. For the calculation of the Z-score relative to the responder population, noted by $Z_R$, the distribution measures, μ and σ, are calculated by using the responder population. For the calculation of the Z-score relative to the non-responder population, noted by $Z_{NR}$, the distribution measures, μ and σ, are calculated by using the non-responder population. Finally, the RAP score is defined by 2, $$\text{monotonic}\left(\frac{|z_R|}{|z_{NR}| + c}\right) \quad \text{Equation 2}$$

where c is a regularization constant that prevents the score from divergence for $Z_{NR}=0$, and monotonoic is an ad-hoc function that was designed to prevent the RAP-score from decreasing for extreme values within the non-responder distributions. The function implementation is given by pseudo-code in Algorithm 1.

Algorithm 1:
The monotonic function used in Equation 2.

if |mean(R) − mean(NR)| > c · std(NR) then
  if mean(NR) > mean(R) then $$\text{sign}(\text{mean}(NR) - x) \cdot RAP \text{ Score} + \frac{(x > \text{mean}(NR) \cdot 2 \cdot |Zscore_R|)}{c}$$

else $$\text{sign}(x - \text{mean}(NR)) \cdot RAP \text{ Score} + \frac{(x < \text{mean}(NR) \cdot 2 \cdot |Zscore_R|)}{c}.$$

To determine the exact number of RAPs for a given patient, a threshold is determined for all proteins, wherein a protein with a RAP score above the determined threshold is considered as a RAP. The threshold is determined using cross-validation which is applied on the training set. Specifically, a cross-validation data set consisting of one third of the training set and a non-cross validation data set consisting of an additional one-third of the training set are sampled, while keeping the number of responders and non-responders similar between cross-validation and non-cross validation data sets. The calculation is performed on the non-cross-validation set and then for each patient in the cross-validation data set, a RAP score is calculated for every feature (i.e., all measured proteins at T0 and T1) using the responder and non-responder expression level distributions. The number of RAPs is then used to predict the response and receiver operating characteristics (ROC) area under the curve (AUC) quantifying the predication performance is calculated for each threshold value.

An alternative approach makes use of decision tree learning based on a machine learning algorithm to classify proteins as RAPs for a given subject. For each measured protein a prediction model is generated using a machine learning algorithm (e.g., XGBoost algorithm) and based on the data of the training set. Such data from the training set may include not only protein expression levels and responder/non-responder tags, but also other features such as patient age, sex, condition, type of treatment, line of treatment, biomarkers expression such as PD-L1 expression etc. This approach makes no assumptions on the protein distribution and offers a natural framework to utilize clinical parameters. The machine learning approach trained only on protein levels was found to be effective, while a combined approach also incorporating the sex and/or age of the patient was found to be even more accurate.

Example 1: Resistance-Associated Biological Processes

To determine biological processes that may be associated with resistance to therapy and can be specifically targeted in combination with immune checkpoint inhibitor (ICI), to improve treatment efficacy, a review of known ICI combination therapies as well as ICI-based combination clinical trials revealed that the vast majority of all combinations comprises agents that target one of five biological processes: Cell proliferation, Inflammation, Immune modulation, Angiogenesis and Metabolism. These categories were defined as follows:

a. Proliferation—Normal cell proliferation is controlled by external stimuli that signal the cell to proliferate. One of the main features of tumor cells is their ability to maintain prolonged proliferation even in the absence of external stimuli.

b. Inflammation—Tumor cells exploit inflammatory mechanisms that enable tumor migration, survival and immune evasion, ultimately supporting tumor progression. As a result, immune cells may secrete tumor-supporting signals that promote tumor migration, survival, and immune evasion.

c. Immune modulation—Tumor cells develop multiple strategies for escaping immune surveillance and destruction. One of the main strategies involves immune checkpoints and immune suppressive mediators that repress immune cell activation. Such mechanisms are blocked using ICI therapy.

d. Angiogenesis—Angiogenesis is a process by which new blood vessels are formed from existing vasculature. Tumors stimulate angiogenesis by producing angiogenic stimuli. This results in the formation of new blood vessels that supply the tumor with oxygen and nutrients, thereby sustaining tumor survival, growth and spread.

e. Metabolism—Cancer cells often activate metabolic processes to generate energy and building blocks required for cell proliferation and tumor progression. Such metabolic changes may also affect the immune system.

As these major processes covered nearly all known/potential combination therapies, it was examined whether patient data from before initiation of ICI treatment could be used to determine which, if any, processes will be activated in specific patients in response to therapy. If it could be determined that a particular process will be active in a cancer patient after ICI treatment, this could effectively inform the ideal secondary therapy to be combined with the ICI.

Figure 1B:
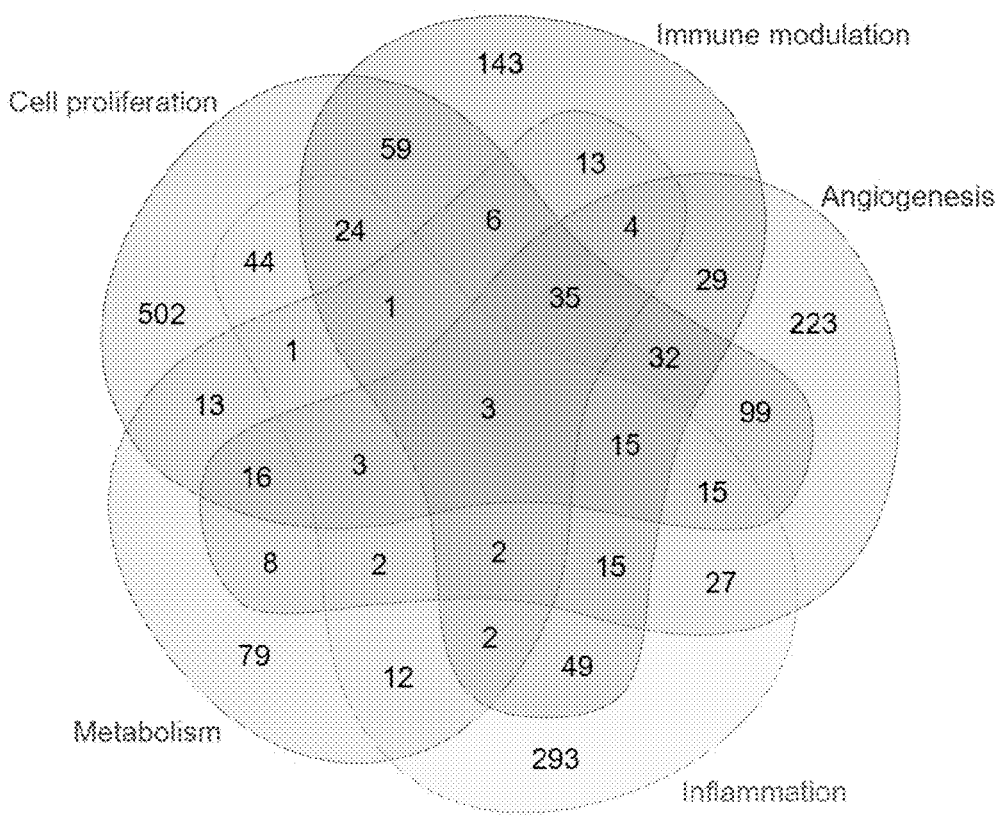
Figure 1C:
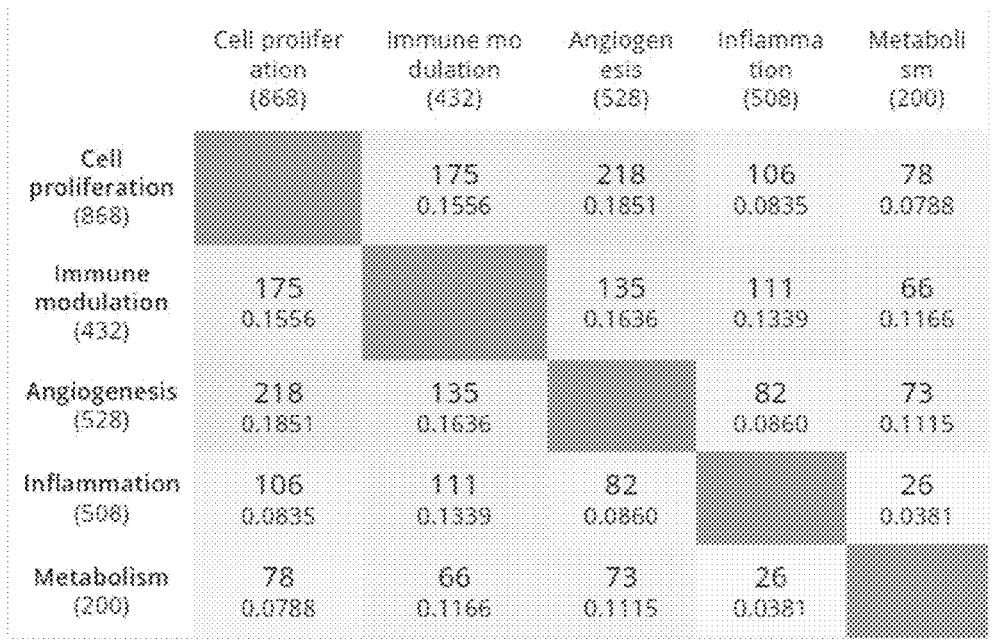
Figure 2A:
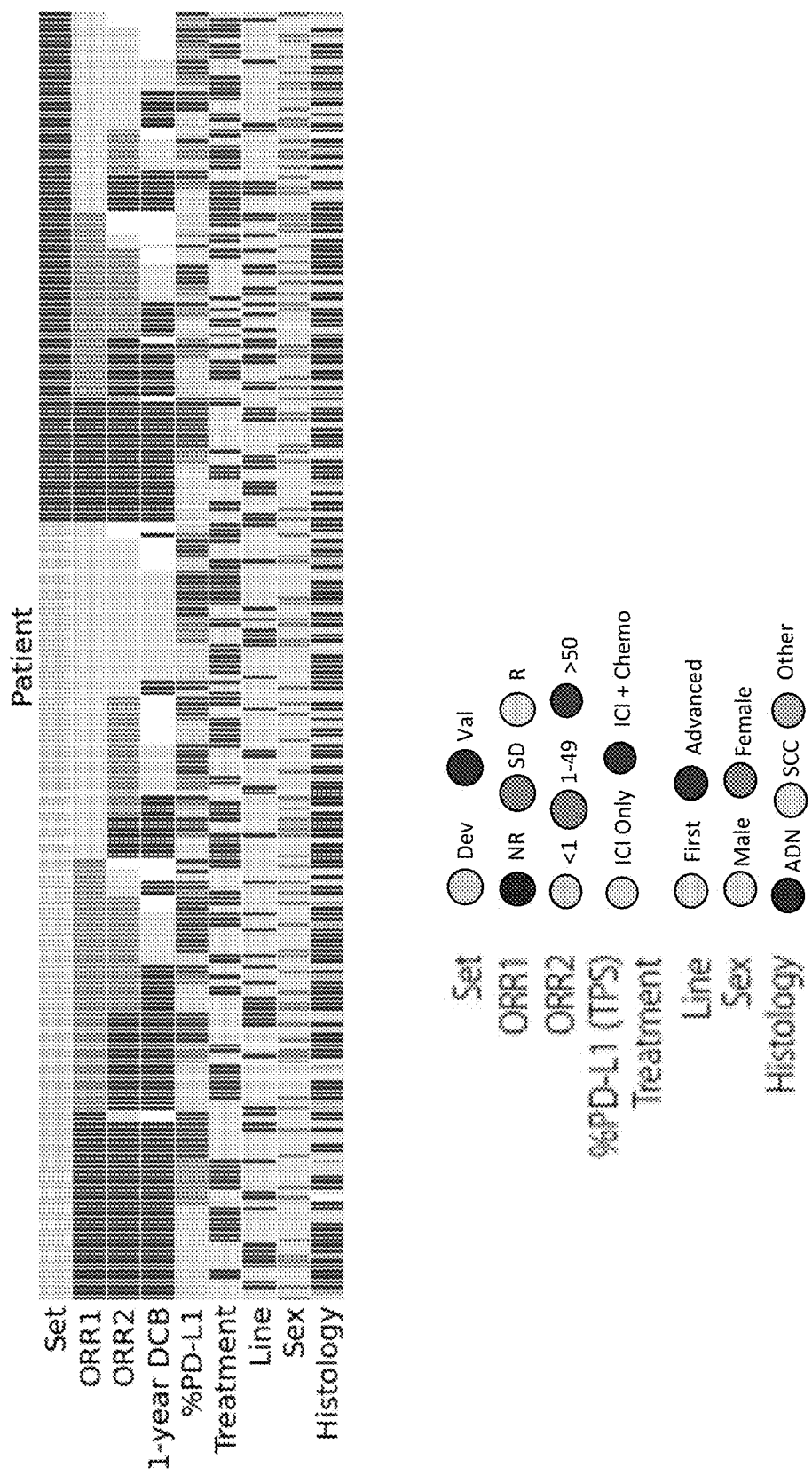
FIGS. 2A-2F: Clinical description of the 184 patients included in the analysis. (2A) Heatmap representing patient clinical characteristics: response to treatment (ORR1, ORR2, 1-year DCB); percent of cells expressing PD-L1 in biopsy immunostaining, a prognostic marker of response to treatment; treatment type: ICI only or combined treatment of ICI and chemotherapy; line of treatment: first line indicates ICI treatment was given as the first systemic treatment for NSCLC, advanced line indicates a previous non-ICI treatment was given before the current ICI treatment was administered. Sex indicates patient sex at birth. Histology indicates the lung cancer histological type (ADC-adenocarcinoma, SCC-squamous cell carcinoma). (2B-2C) Violin plots of the correlation of the patient age with response in each time point: (2B) ORR1 and (2C) ORR2. ORR1 and ORR2 are overall response determined 3 months and 6 months following treatment initiation, respectively. (2D-2E) Graphical display of the response groups in (2D) ORR1 and (2E) ORR2. NR=non-responders. R=responders (partial responders or complete responders). SD=stable disease (in the model they are included in the responder group). (2F) Graphical display of the division of the population into the development and the validation sets.
Figure 2B:
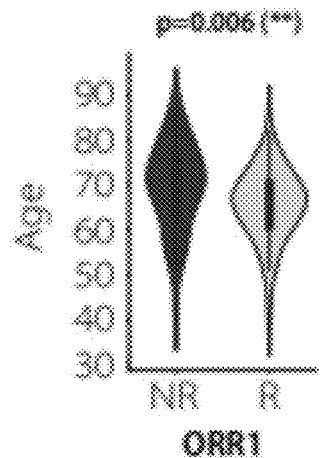
Figure 2C:
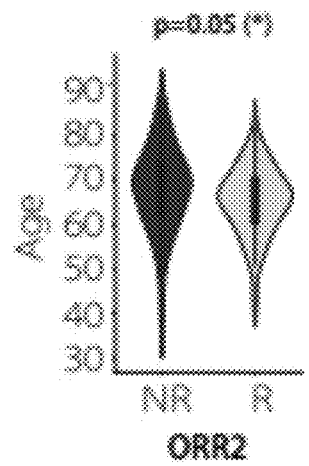
Figure 2D:
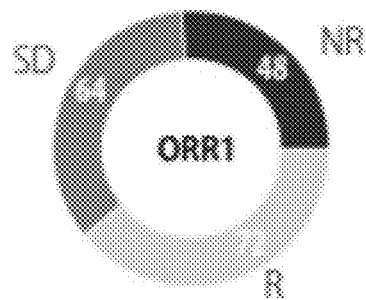
Figure 2E:
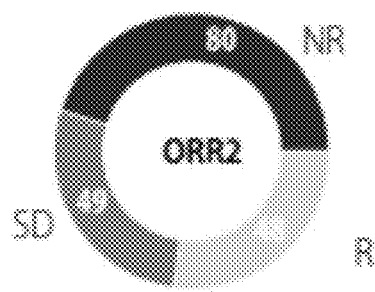
Figure 2F:
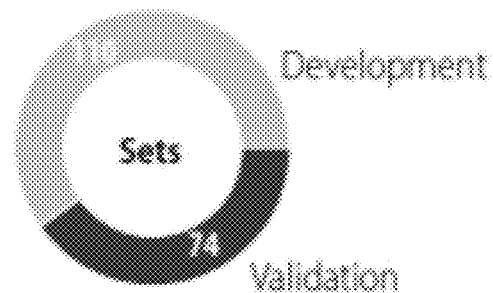

To identify which proteins are involved in each of those processes, publicly available pathway databases were searched for pathways associated with these biological processes, and the involved proteins were listed. The various pathways that were integrated to generate the processes protein lists are summarized in FIG. 1A. This was followed by a manual curation and the final list of proteins in each biological process was used as an input for a process activation algorithm. In total, 396, 508, 528, 868, 200 proteins were associated with immune modulation, inflammation, angiogenesis, proliferation, and metabolism, respectively (FIG. 1A). These curated processes showed less than 20% intersection in their protein list with the highest intersection between proliferation and angiogenesis (FIG. 1B-1C). Not surprisingly, the first step in angiogenesis occurs by the formation of a new sprout, mediated by cell migration and cell proliferation, so, this intersection can be explained by established biological rational. Furthermore, several studies showed that VEGF, the key driver of angiogenesis is also an immunosuppressive factor which could also partly explain angiogenesis and immune modulation protein intersection.

Example 2: Predicting Responders and Non-Responders Using Machine Learning

A cohort of 184 non-small cell lung cancer (NSCLC) was used to evaluate the ability to predict response to treatment and to identify processes that will be active in a subject after first-line treatment with an ICI. Blood samples were obtained prior to the first administration (T0) and after the first (T1) administration with ICI, and protein levels were measured. Response evaluation was based on ORR at three months (ORR1) and six months (ORR2) and durable clinical benefit (DCB) at one year post treatment initiation. Progression free survival (PFS) and overall survival (OS) were also monitored. For 3- and 6-month evaluation, subjects with progressive disease or death were considered non-responders, while subjects with stable disease, minimal remission, partial remission and complete remission were considered responders. DCB was defined as one year of PFS with continued ICI treatment. Cases of ICI treatment stop due to adverse event (but no signs of progression) were considered as responders. Additional clinical information collected throughout the study included: line of treatment (first or advanced), PD-L1 immunostaining (below 1%, between 1-49%, above 50%), age and sex (see FIG. 2A-2F). The presented analysis is based on T0 only. The breakdown of ICIs/therapies used is provided in Table 1.

TABLE 1

| Treatment | Target | Patient count |
| --- | --- | --- |
| Pembrolizumab | PD-1 | 54 |
| Pembrolizumab, Chemo | PD-1 | 86 |
| Nivolumab | PD-1 | 25 |
| Nivolumab, Chemo | PD-1 | 2 |
| Ipilimumab, Nivolumab | CTLA4 | 7 |
| Ipilimumab, Nivolumab, Chemo | CTLA4 | 6 |

TABLE 1-continued

| Treatment | Target | Patient count |
|---|---|---|
| Atezolizumab | PD-L1 | 1 |
| Atezolizumab, Chemo, targeted therapy | PD-L1 | 1 |
| Durvalumab | PD-L1 | 1 |
| Durvalumab, Chemo | PD-L1 | 1 |

For the response prediction classifier, the cohort was divided into a development set (60% of the subjects) and a validation set (40% of the subjects). Models (see Materials and Methods) were trained on the training set and predictions were generated for a subset of patients not seen by the models during training (i.e., test sets). The division of the development set into training and test set was performed multiple times (each time for training the model on a different subset of the development set and performing predictions on the remaining patients. i.e., the training and test sets were mixed and remixed and tens of iterations were run to test that a model/classifier was effective across the entire development set) in order to generate a stable prediction for all patients in the development set. The prediction quality was then quantified by calculating the ROC AUC for the patients included in the development set. The validation set was used only at the very end of the analysis to validate the functionality of the final classifier. This division was performed multiple times, Models were generated based on response evaluation at three time-points: three months, six months, and a year after treatment onset. All 184 patients were evaluated at the three-month time point, 177 were evaluated at six months and 146 were evaluated at 1 year. Resistance increased over time. 26% of the subject were non-responders at three months, 45% were non-responders at six months and 74% were non-responders at 1 year. These ratios were similar between the development and validation sets.

During model generation based on the development set, the development set was randomly divided into a training and a test sets 60 times. On each iteration, the top candidate protein targets were selected using the Kolmogorov-Smirnov test. For each selected protein, a single protein XGBoost model (SP model) was fitted to the training set and predictions were generated for the test set. For each measured protein a prediction model was generated, and a protein was defined as a RAP for a specific patient if the predicted resistance probability was above a predefined threshold, and the average of all the iterations was used as the RAP number for each patient. A uniform threshold was assigned for all models, in order to handle class imbalance. Different thresholds were defined for each time point (e.g., three months threshold=0.25, six-month threshold=0.42, one year threshold=0.45). For each patient, the resistance score was calculated as the number of proteins for which the model score exceeded a defined threshold (i.e., the number of RAPs).

Merely looking at the number of RAPs was predictive with this cohort. However, a predictor model was created that could also integrate clinical data. The presented clinical classifier used the number of RAPs, the line of treatment (was the ICI the first line of treatment or an advanced line), the subject's age and the percent of PD-L1 staining in the tumor (below 1% of cells positive, between 1-49%, or above 50%) as the inputs. The classifier then produced a final resistance score between 0 and 1, in which 0 was most similar to responders and 1 was most similar to non-responders. Subjects with a score above a predetermined threshold were predicted to be non-responders. Similarly, a response score, which is 1-resistance score, was also calculated. For the response score, a subject with a score above a predetermined threshold was predicted to be a responder.

Figure 3A:
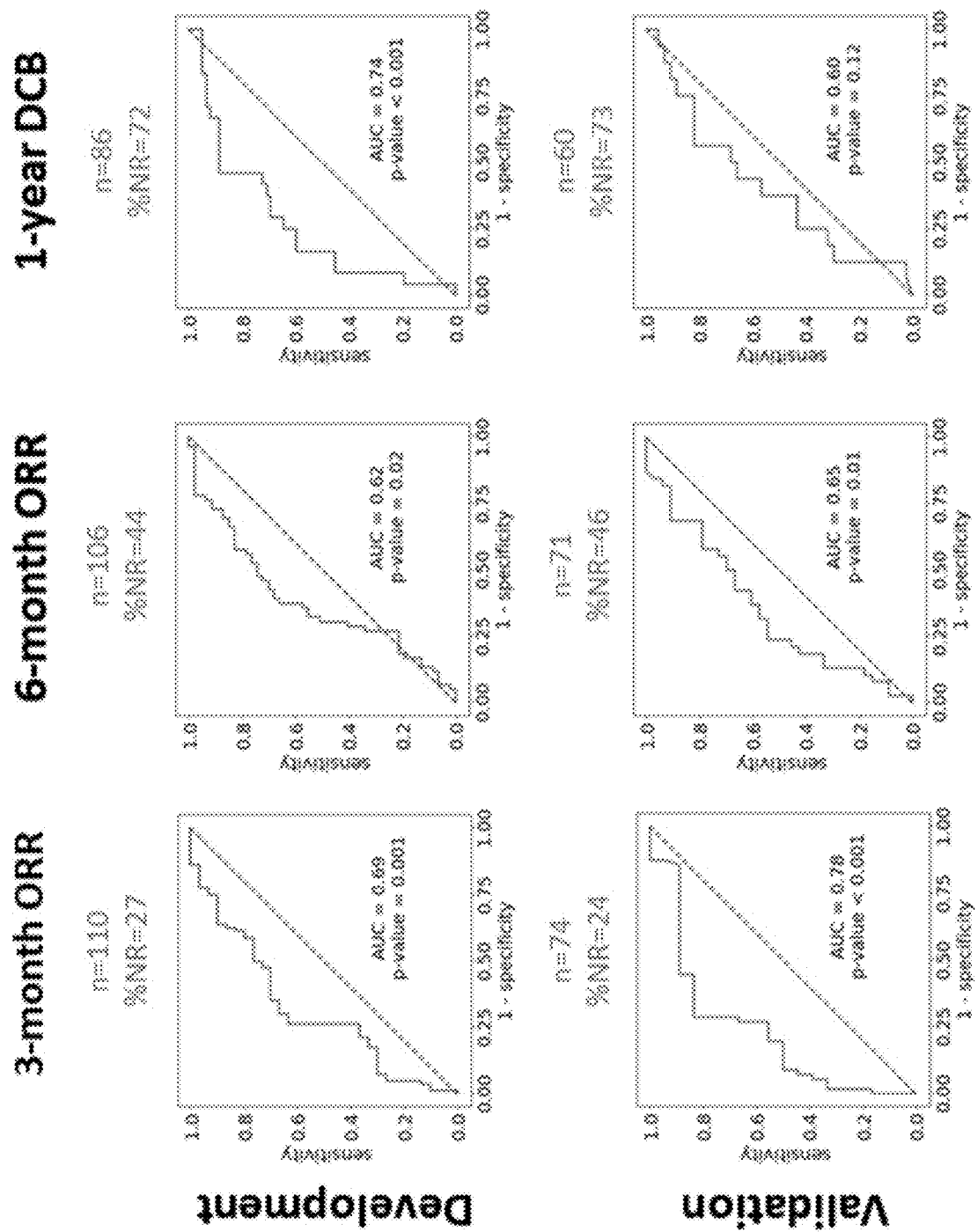
FIGS. 3A-3B: Performance of the classification model. ROC AUC was calculated using the final resistance score together with actual overall response evaluation at 3-month ORR, -6-month ORR and 1 year duration of clinical benefit (DCB) for both TO and T1. Results at TO for the (3A, upper panel) development set and for the (3A, lower panel and 3B, upper panel) validation set are shown. (3B, lower panel) A similar classification model was generated based on T1.
Figure 3B:
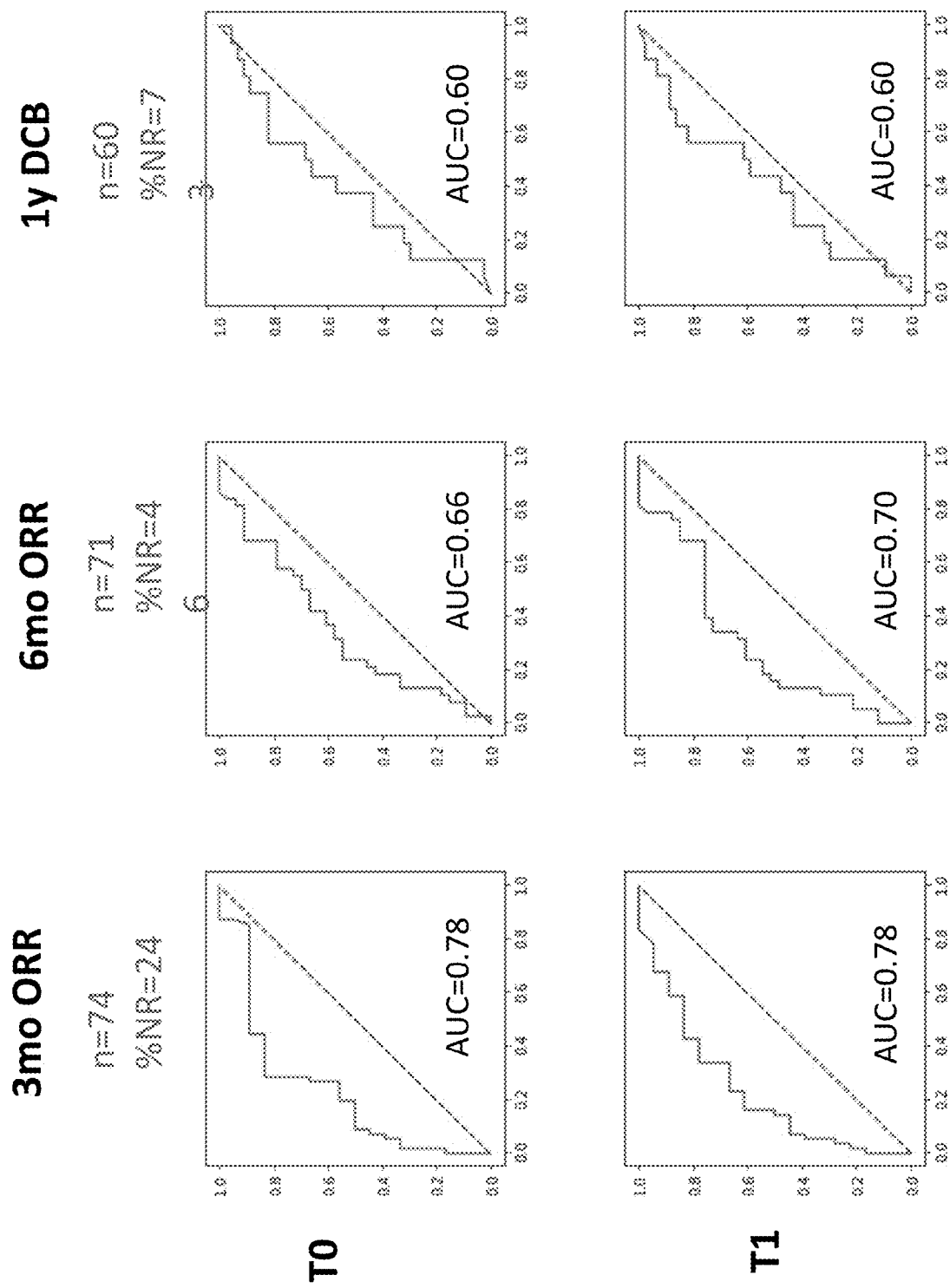

In order to test the performance of the classification model, a ROC AUC was calculated using the final resistance score together with actual response. The ROC AUC was calculated separately for 3-months ORR, 6-months ORR and 1-year DCB for both T0 and T1. The results are summarized in FIG. 3A. The classifier was found to be predictive at all time points and for both development and validation sets. A similar analysis showed that the classifier was found to be predictive at all time points also for the T1 data (FIG. 3B).

Figures 4A, 4B:
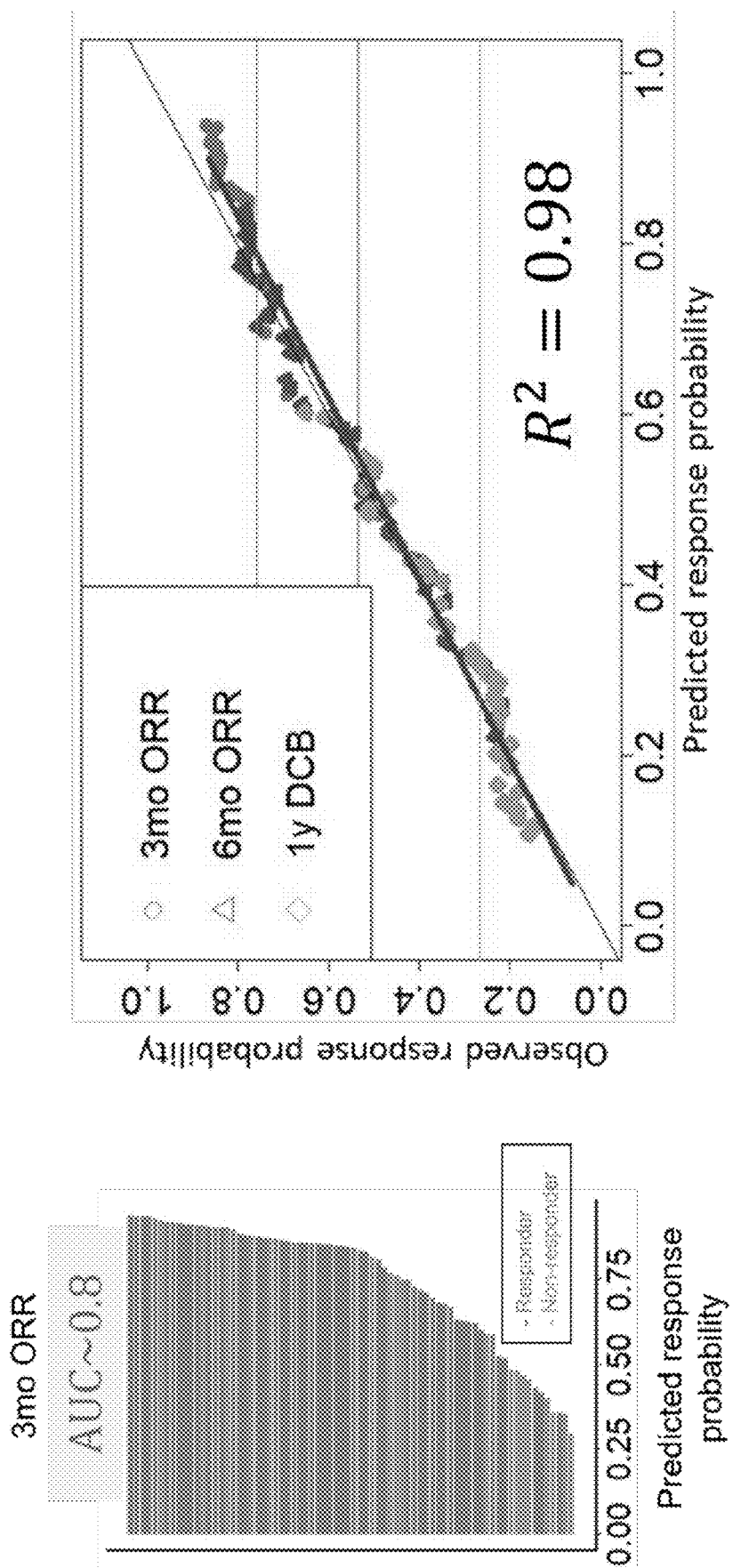
FIGS. 4A-4B: (4A) Patients sorted by their response probability score (calculated as 1-resistance score) based on protein levels at TO. Actual observed response at 3 months ORR is indicated by color for each patient. (4B) Dot plot of the agreement between the predicted response probability based on TO protein expression and observed response probability at either 3 months, 6 months or 1 year. Each point on the graph indicates a specific patient, and the different time points are indicated by different colors and marker types. The black diagonal line indicates the line y=x, the red diagonal line indicates the fitted regression line for all the points and the goodness of fit of the regression ($R^2$) is indicated. The horizontal lines indicate the average observed response probability for the 3 timepoints (color coded) across the entire validation set.

Further to checking the performance of the classification model, the correlation between the predicted response probability (response score) assigned by the classification model to each patient and the observed response probability was also examined. For this purpose, for each value of response score $S_0$, the observed response probability is given by the fraction of responders among patients that were assigned a response score within the range $S_0 \pm 0.1$. The choice of an interval of $\pm 0.1$ is arbitrary and reflects the validation set size; within a larger validation set the interval can be further reduced. The agreement between the predicted response score and the actual response probability was quantified by the goodness of fit $R^2$. The goodness of fit for all 3 timepoints (3 months ORR, 6 months ORR and 1-year DCB) was $R^2=0.98$ for time point T0 (FIG. 4A-4B).

Figures 5A, 5B:
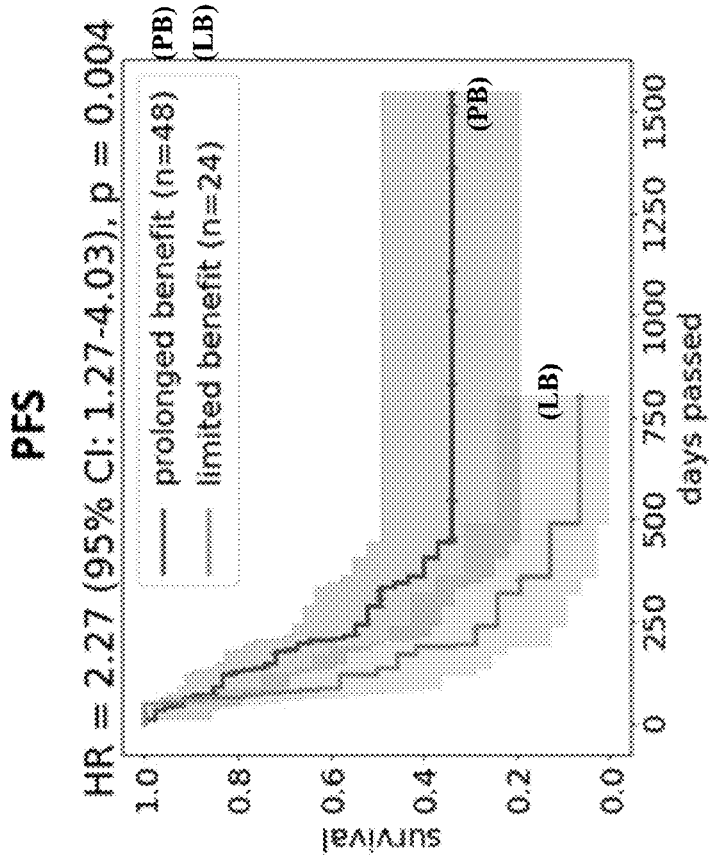
FIGS. 5A-5B: Survival analysis based on prediction results for ORR at 3-months based on T0 protein measurements for (5A) PFS and (5B) OS.

Patients within the validation set were stratified to prolonged benefit and limited benefit populations, where the stratification was based on the predicted 3-month response score. In survival analysis the stratification quality was measured by the hazard ratio (HR), which gives the ratio of probability for event per time unit within the two population. For example, HR of 4 in overall survival (OS) means that the probability for a death event per unit time among the limited benefit population is 4 times the probability per unit time among the prolong benefit population. The HR in the validation set was 2.27, p<0.004, for PFS (FIG. 5A) and 4.50, p<0.0001, for OS (FIG. 5B).

Example 3: Personalized Active Processes Map

The measured protein levels of the 184 NSCLC patients were further taken for analysis of the active biological processes. Among the 7289 measured circulating proteins, 6873 targets were considered as valid after quality control evaluation. Those targets corresponded to 6054 different proteins, some of them measured by different probes or the same probe repeated in the assay. To avoid over representation of a specific protein from multiple measurements, a dictionary was created, with one-to-one mapping from probe identifier to protein. Proteins measured multiple times were compared, and only proteins where all the different measurements had a spearman correlation larger than 0.75 were kept. The probe identifier with the highest correlation to all other probe identifiers was chosen as the target representing the protein. Probe identifiers that were used as a RAP for the prediction engine were also kept. In total, 5256 targets/proteins were used for the processes analysis.

Figure 6:
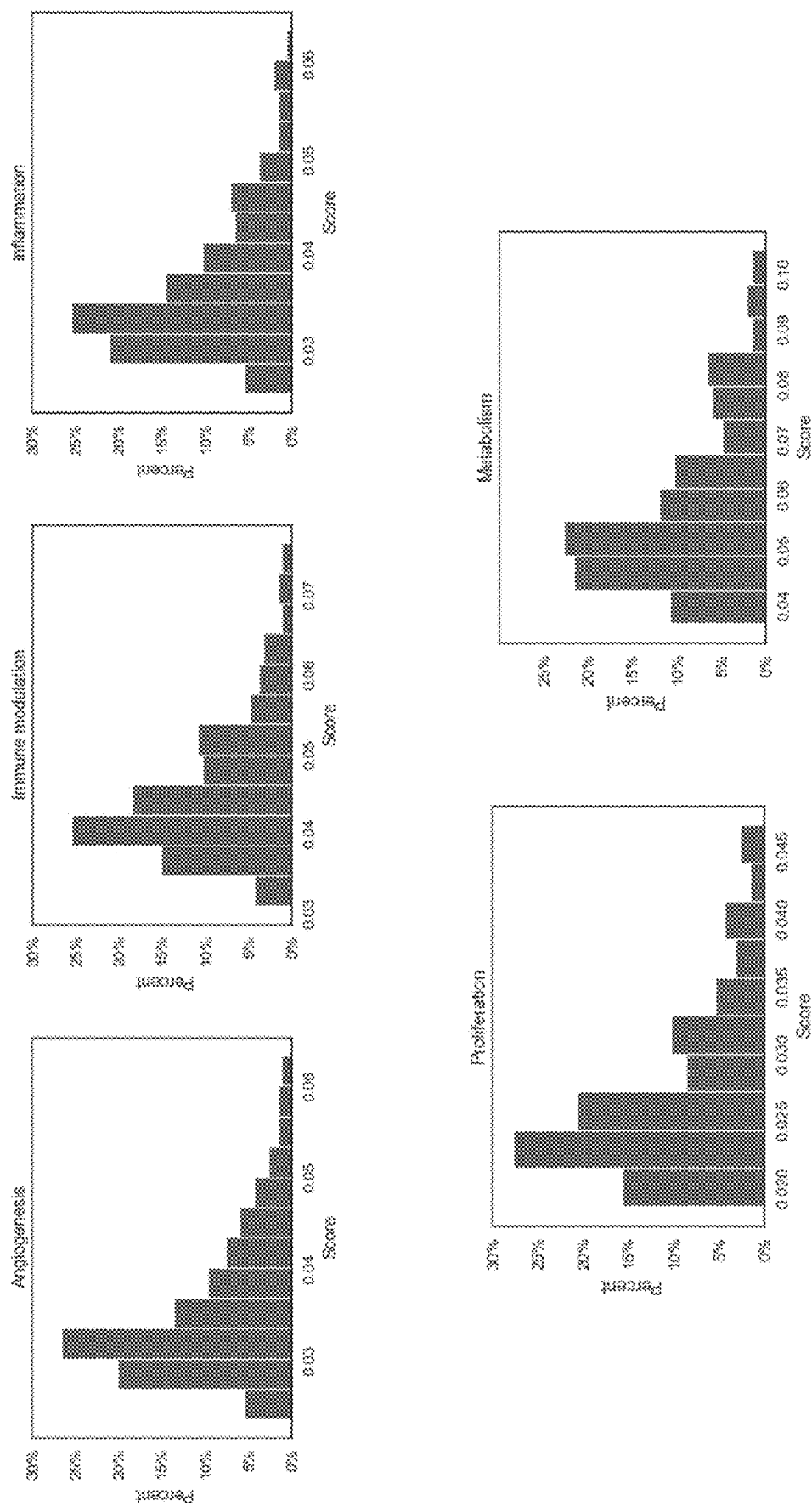
FIG. 6: Bar graphs of the scores in each of the biological processes based on Euclidian distance for all subjects in the cohort.
Figure 7A:
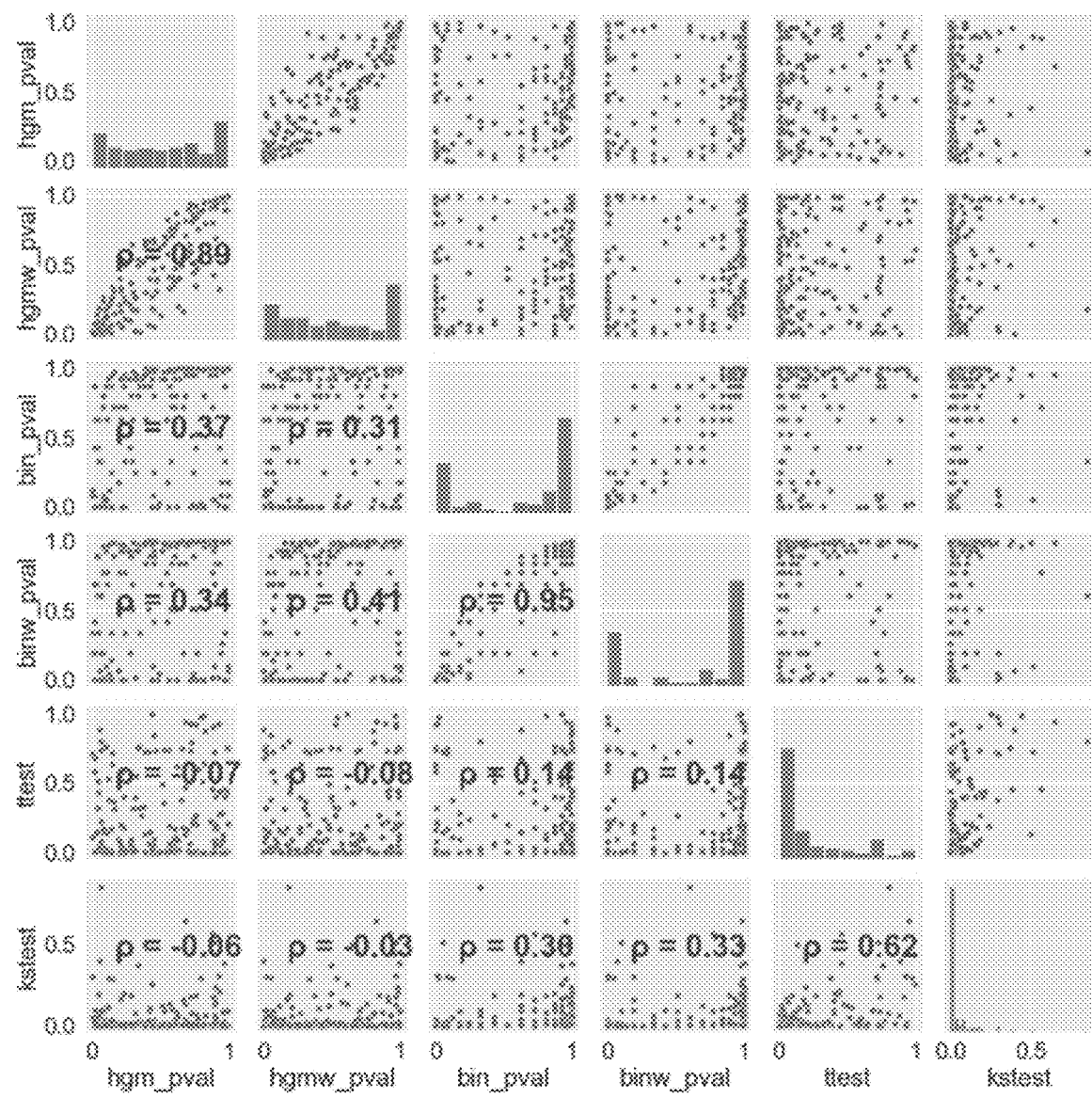
FIGS. 7A-7D: (7A): Immune modulation process scoring pair plot. In each subplot the points represent the patients. The lower diagonal includes the spearman correlation coefficients in red. "hgm"—hyper geometric test. "bin"—binomial test. "w" suffix—weighted test. "kstest" and "ttest" are p values of the Kolmogorov Smirnov and t test of the patient process proteins profile compared with the cohort population (1D enrichment). (7B) Biological processes scoring using the normalized Euclidean distance (rss_norm) shows a high correlation between the different biological processes. (7C-7D) Correlations between the rss_norm scoring of randomly generated processes. Each process is composed from 200 targets. The effect was verified for both timepoints (T0 and T1) and observed in with measurements from two different protein arrays (7C) and (7D).

The relative fluorescent unit (RFU) measurements of the selected proteins at T0 were log 2 transformed followed by Z-score normalization. The Euclidean distance of each process was used to generate a process score (FIG. 6). To avoid over contribution of outliers, the maximal absolute value of the Z-score was set to 2. Several methods for scoring were used including first generation methods (HyperGeometric, Fisher exact, either weighted or non-weighted) and second-generation methods (1D-ssGSEA), all resulting in problematic scoring profiles in which all the processes behaved in the same manner (FIG. 7A). In one basic analysis a naïve scoring for the processes was defined to be the root of sum of squares of the process proteins:

$$Score = \frac{\sqrt{\sum_{process} Z^2}}{n_{process}}$$

Figure 7B:
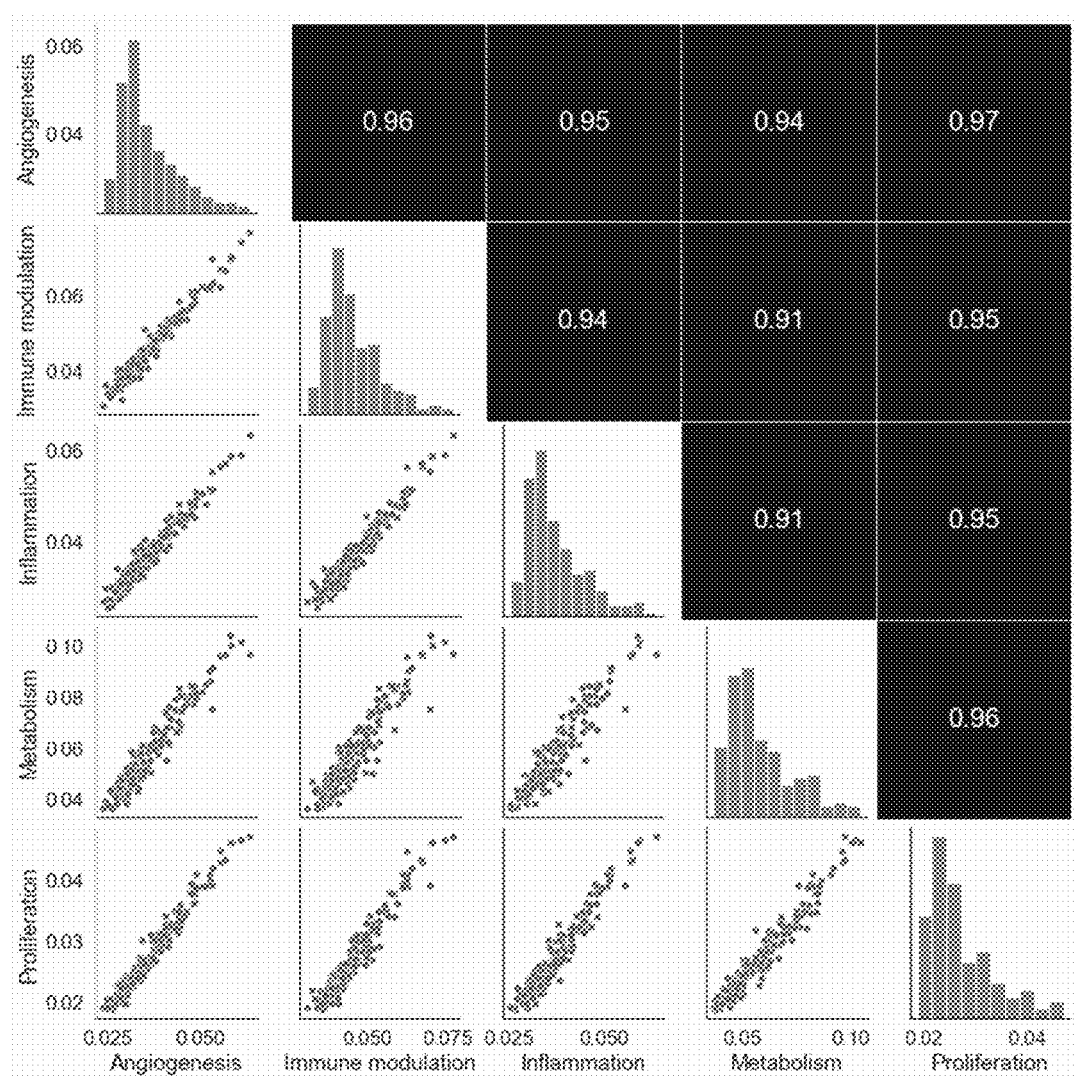
Figure 7C:
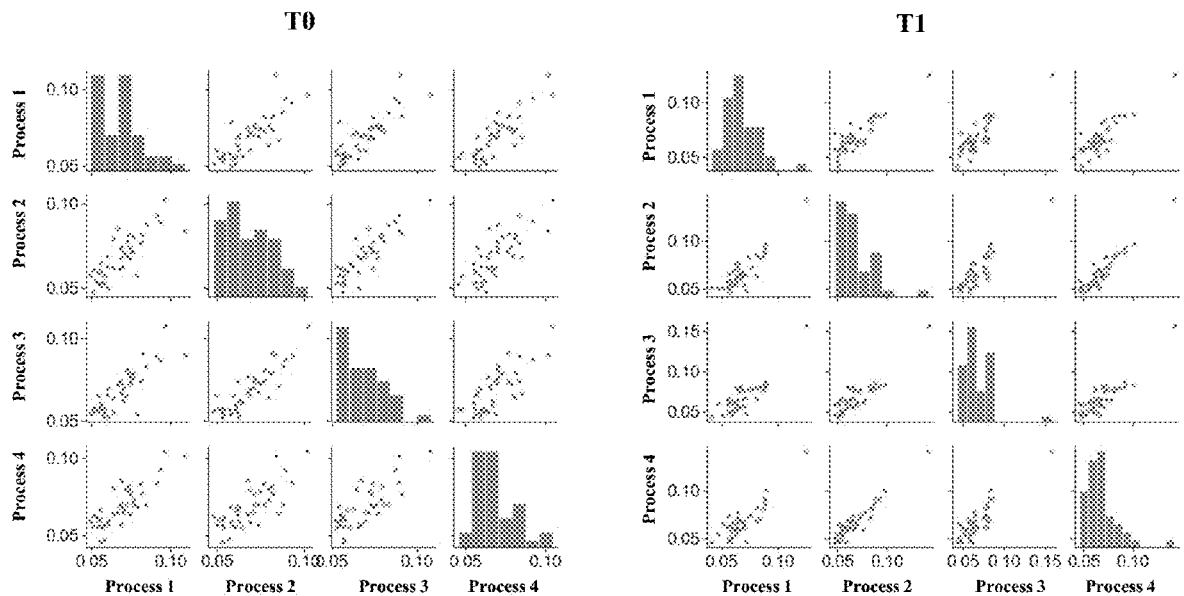
Figure 7D:
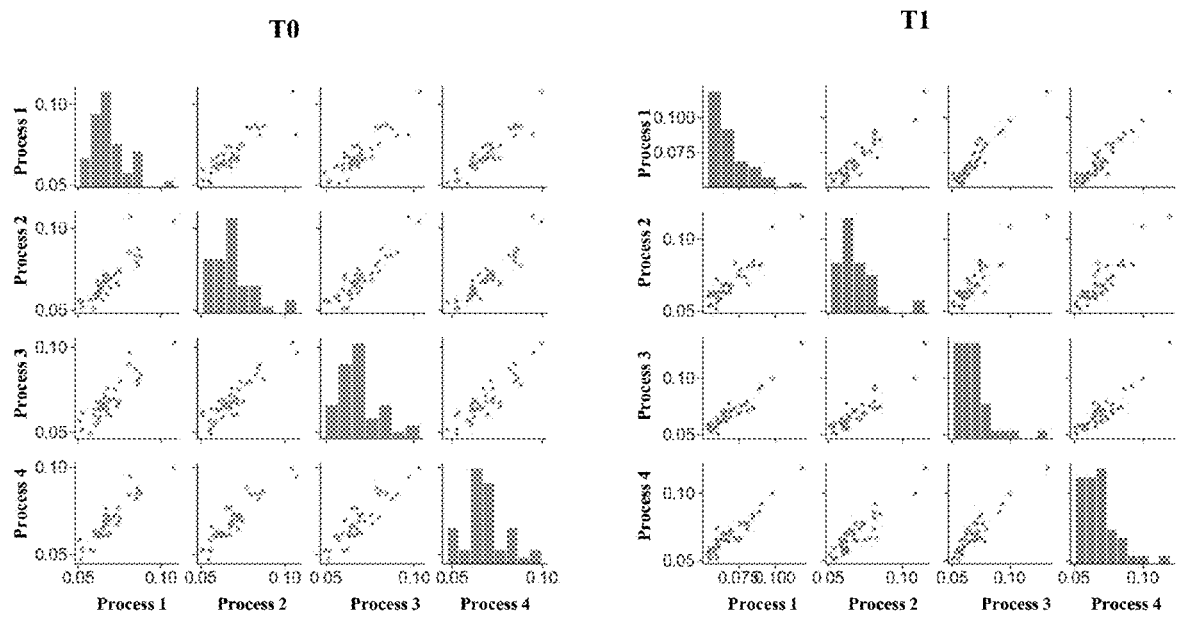

The naïve scoring showed high correlations between the different processes (FIG. 7B) A similar result was found when a second protein array, was used (FIG. 7C). Moreover, a similar score was obtained when taking 100 random proteins which are not members of the same process. This similarity in the scores of every tested process rendered the data hard to interpret, since no decision could be made on the optimal second therapy when all the processes are active to the same extent or the opposite. It was assumed that this phenomena of similarity of the scores for every tested process was originated by the similarity in the expression level of all the proteins measured in the same patient. To estimate the activity of a specific process compared to the general protein level of the sample two methods were investigated: A. Compare every process score of a single patient with (N=1000) randomly generated processes scores, each randomly generated process having the same number of targets as the original process (p-value); B. Normalize the protein measurements so that the sum of the entire set of proteins composed from all of targets is equal to 1:

$$Score = \sqrt{\frac{\sum_{targets} process\ Z^2}{\sum_{targets} all\ Z^2}} \times \frac{n_{all}}{n_{process}}$$

Figure 8:
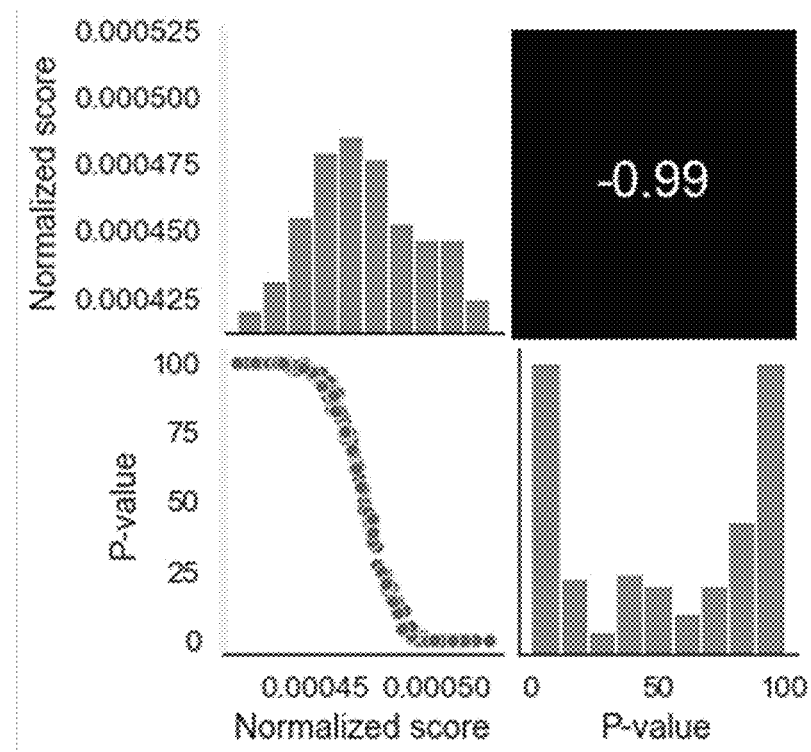
FIG. 8: Two different scoring methods giving the same result: The normalized Euclidean distance (rss_norm), i.e., fraction of random processes with Euclidean distance larger than the actual process Euclidean distance, and the p-value (rss_rank) gave similar results as to the active cancer process in each subject.
Figure 9A:
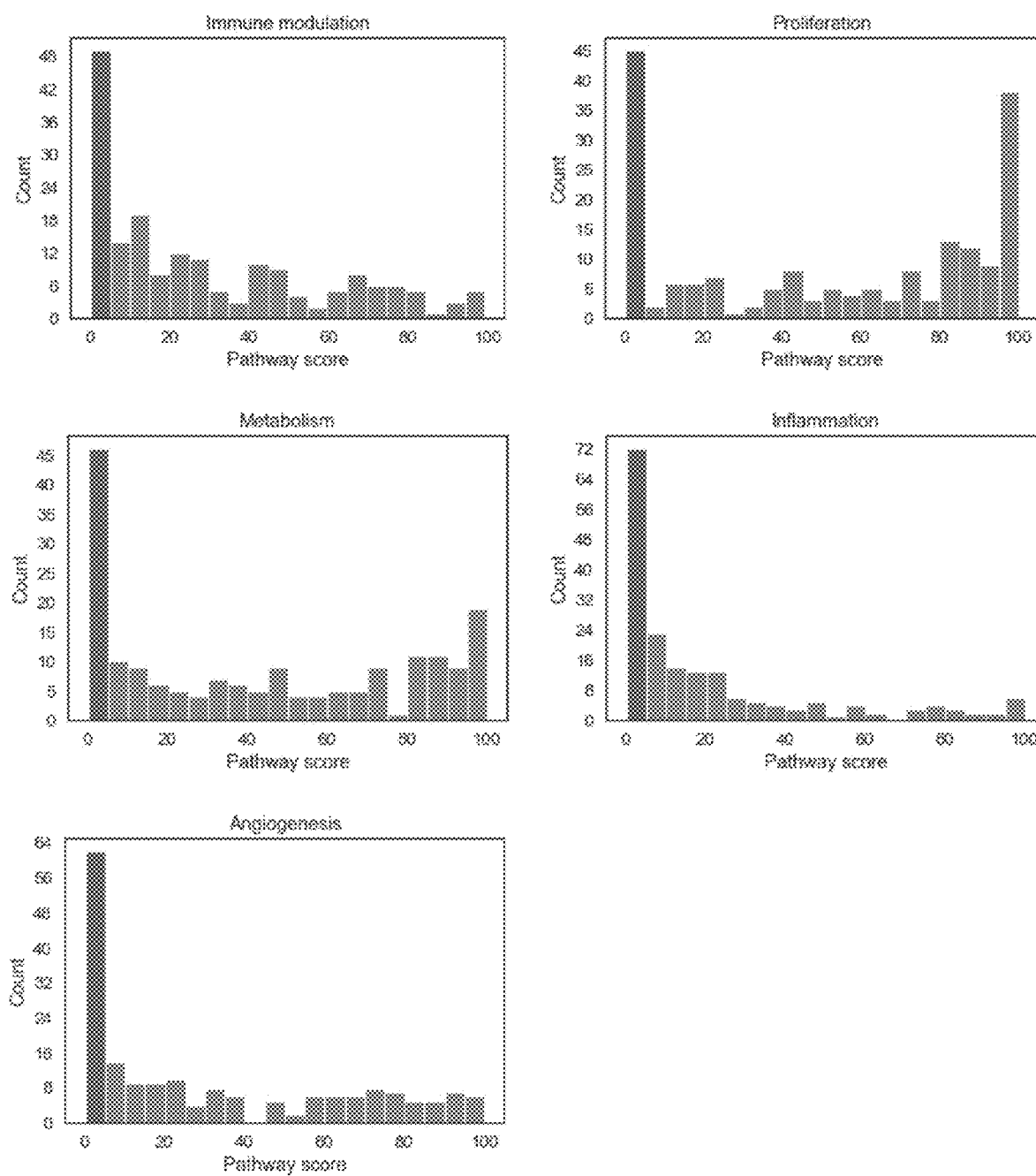
FIGS. 9A-9C: P-value scoring of biological processes. (9A) Bar graphs of the processes scores. Processes with p-value <5% are identified as active. Y axis—number of patients; x-axis—process score (9B) Table of the shared process frequency and relation to response. (9C) Pair plot of processes scores.

Both methods gave the same ranking for a certain process (FIG. 8), and both methods were able to identify specific active processes for each subject (FIG. 9A). The p-value method provided a simple threshold (p<5%) for determining active processes. Further, both methods were able to identify specific active processes for each subject (FIG. 9A).

In total, the analysis method comprised four steps. 1. Associate all proteins/measurements from a patient with processes. 2. Calculate the Euclidean distance of each process to give a score. 3. Calculate the P-value or normalized score for each process. 4. Select processes with a P-value below a threshold (<0.05) or a normalized score above a threshold as active processes in the cancer of the subject.

Figures 9B, 9C:
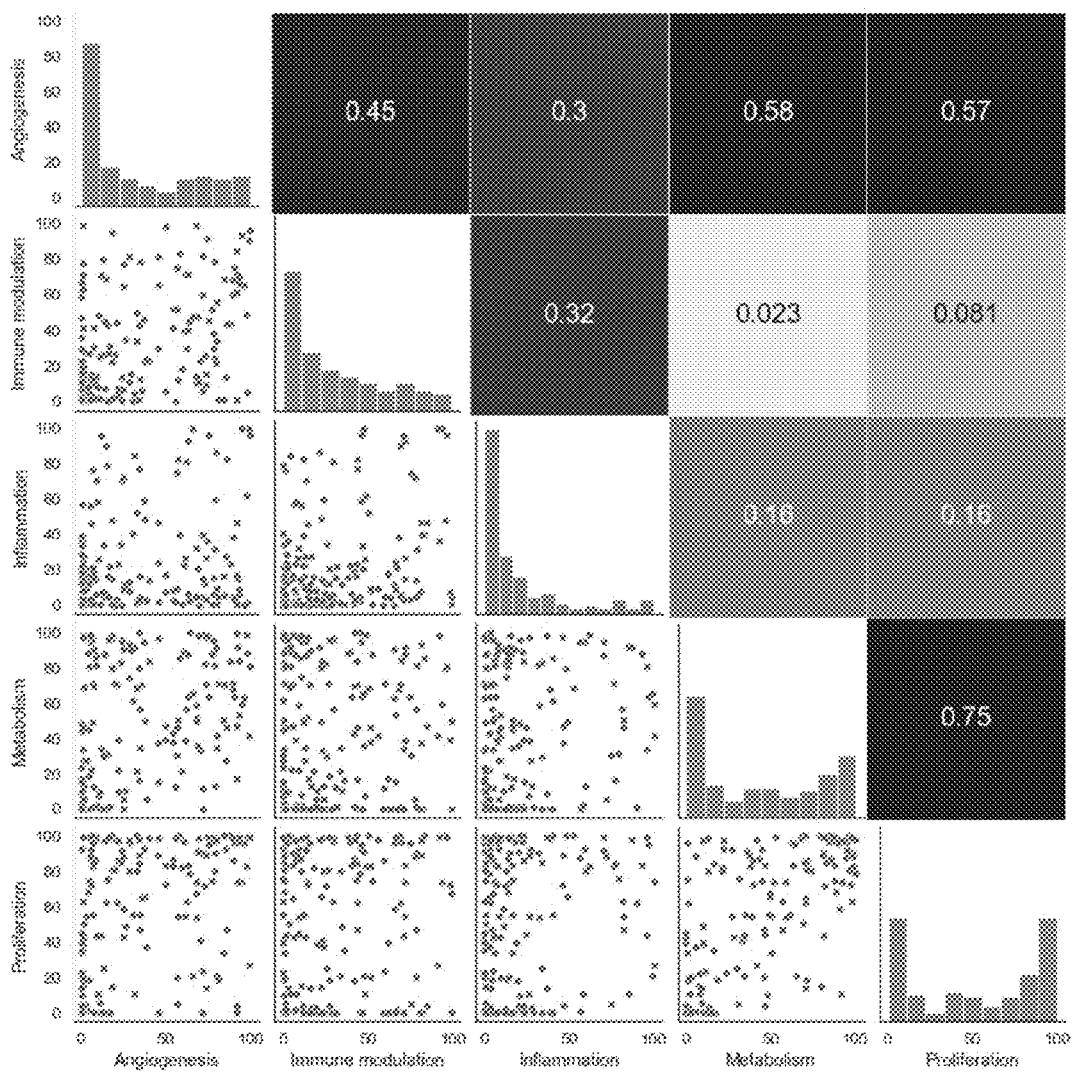

The inflammation process was the most activated process among patients (i.e., most patients had a process score of 5 of less which corresponds to a P-value of 0.05 or less), followed by immune modulation and angiogenesis (FIG. 9A). Only 7 of the patients showed activation of all the processes, and only 17 out of 184 patients had 4 activated processes (FIG. 9B). Some correlation between inflammation, immune modulation and angiogenesis was observed when comparing the scoring of the various patients (FIG. 9C).

Example 4: Targeting Process Activation

After identifying the active processes that may interfere with therapy success in each subject, those can be targeted with an effective secondary therapy.

Cell proliferation: Current treatments that target cell proliferation primarily include chemotherapy, radiotherapy and targeted therapy. Patients displaying a high proliferation signal may potentially benefit from anti-PD-1/PD-L1-based immune checkpoint blockade (ICB) therapy in combination with one of these treatments. Treatment combinations of approved and/or investigational drugs were explored in NSCLC patients in the following studies: Pembrolizumab in combination with Carboplatin and Pemetrexed, Paclitaxel and carboplatin, Erlotinib, or Gefitinib (NCT02039674), Pembrolizumab in combination with Pemetrexed, Carboplatin and Cisplatin (NCT02578680); Pembrolizumab in combination with carboplatin and Paclitaxel or nab-paclitaxel (NCT02775435); Atezolizumab in combination with carboplatin and nab-paclitaxel (NCT02367781); Atezolizumab in combination with carboplatin and paclitaxel (NCT02366143); Durvalumab in combination with AZD9150, AZD6738, or Vistusertib (AZD2014) (NCT03334617); Pembrolizumab in combination with Datopotamab Deruxtecan (NCT05215340); Durvalumab in combination with concurrent chemoradiotherapy (CCRT), Nivolumab and ipilimumab in combination with CCRT, or Nivolumab in combination with CCRT (NCT04026412); Pembrolizumab or Durvalumab in combination with chemotherapy and radiotherapy (Etoposide, Carboplatin, Cisplatin, Paclitaxel, or Pemetrexed combined with external beam radiation) (NCT04380636); Durvalumab in combination with chemotherapy (Carboplatin, Cisplatin, Etoposide, Paclitaxel and Pemetrexed Disodium (NCT04092283); Ipilimumab and Nivolumab in combination with local consolidation therapy consisting of surgery and/or radiation (NCT03391869); Pembrolizumab in combination with stereotactic body radiation (NCT03867175); Ipilimumab, Nivolumab and Pembrolizumab in combination with Carboplatin, Nab-paclitaxel, Paclitaxel and Pemetrexed with or without Stereotactic Body Radiation Therapy (NCT04929041); Pembrolizumab in combination with tisotumab vedotin together with carboplatin or cisplatin (NCT03485209); Tislelizumab in combination with Ociperlimab and Concurrent Chemoradiotherapy (Cisplatin, carboplatin, etoposide, paclitaxel, pemetrexed), or Tislelizumab in combination with Chemoradiotherapy (NCT04866017); Pembrolizumab in combination with Tomivosertib (NCT04622007); Pembrolizumab in combination with Sacituzumab Govitecan-hziy (SG) and chemotherapy (Carboplatin and Csiplatin) (NCT05186974); Nivolumab in combination with Azacitidine and Entinostat (NCT01928576); Pembrolizumab in combination with brentuximab vedotin (NCT04609566); Pembrolizumab in combination with TATE (Trans-arterial Tirapazamine Embolization, NCT04701476); Pembrolizumab in combination with LMB-100 (NCT04027946); Pembrolizumab in combination with SAR408701 (Tusamitamab ravtansine) and Carboplatin and/or Cisplatin and/or Pemetrexed (NCT04524689); Injectable Pembrolizumab and ipilimumab in combination with Cytoxan, Cryosurgical freezing (cryosurgery), and GM-CSF (NCT04713371); Injectable Pembrolizumab and ipilimumab in combination with Non-ablative Cryosurgical freezing and GM-CSF (NCT04739618); Atezolizumab in combination with Ipatasertib, RO6958688, Cobimetinib or Sacituzumab Govitecan (NCT03337698); Cemiplimab in combination with 6-Thio-2'-Deoxyguanosine (NCT05208944), Durvalumab with low-dose PCI (NCT04597671); Pembrolizumab in combination with radiotherapy and carboplatin and paclitaxel or in combination with carboplatin or cisplatin and pemetrexed (NCT03774732); Pembrolizumab in combination with Cryoablation, pemetrexed and carboplatin (NCT04339218).

Inflammation: Patients displaying a high inflammatory signal may potentially benefit from anti-PD-1/PD-L1-based ICB therapy in combination with anti-inflammatory treatments. Some combinations are being tested in clinical trials. Pembrolizumab in combination with Paclitaxel, carboplatin, and Bevacizumab (NCT02039674); Ipilimumab and/or Nivolumab in combination with BMS-986253 (NCT03400332); Atezolizumab in combination with BNT411, Carboplatin and Etoposide (NCT04101357); Nivolumab in combination with BDC-1001 (NCT04278144); Atezolizumab in combination with Tocilizumab (NCT04691817) Pembrolizumab in combination with TransCon TLR7/8 Agonist (NCT04799054); Durvalumab in combination with Canakinumab, radiotherapy and chemotherapy (carboplatin or cisplatin with etoposide, paclitaxel, albumin-bound paclitaxel or pemetrexed, NCT04905316); Nivolumab in combination with Pixatimod and Cyclophosphamide (NCT05061017)

Immune modulation: Currently, the FDA has approved specific ICBs for the treatment of multiple cancer types, while additional ICBs are being investigated in clinical trials. Patients displaying a high immune modulation signal may experience an involvement of additional immune checkpoints besides PD1, PD-L1 or CTLA4. Thus, such patients may potentially benefit from approved combination of ICBs such as nivolumab and ipilimumab (Checkmate227 and CheckMate-9LA studies) or other combinations studied in phase 2/3 clinical trials. Ipilimumab in combination with Nivolumab, Carboplatin, Paclitaxel, Pemetrexed and Cisplatin (NCT03215706); Ipilimumab in combination with Nivolumab (NCT02477826); Durvalumab in combination with AZD6738 (ceralasertib), Oleclumab, or Olaparib (AZD2281) (NCT03334617); Pembrolizumab in combination with LN-145 (NCT03645928); Nivolumab and Ipilimumab in combination with LN-145 (NCT03645928); Ipilimumab in combination with Feladilimab or GSK4428859A (NCT03739710); Pembrolizumab in combination with MK-5890, MK-4830 or MK-0482 (NCT04165096); Zimberelimab in combination with Domvanalimab and/or Etrumadenant (NCT04262856); Atezolizumab in combination with Tiragolumab (NCT04294810); Pembrolizumab or Durvalumab in combination with chemotherapy and radiotherapy (Etoposide, Carboplatin, Cisplatin, Paclitaxel, or Pemetrexed combined with external beam radiation) and olaparib (NCT04380636); Pembrolizumab in combination with Niraparib (NCT04475939); Atezolizumab in combination with Tiragolumab (NCT04513925); Atezolizumab or Pembrolizumab in combination with Tiragolumab and chemotherapy (Pemetrexed, Carboplatin and Cisplatin, NCT04619797); Nivolumab in combination with Relatlimab and chemotherapy (two chemotherapies among Carboplatin, Cisplatin, Paclitaxel, Nab-Paclitaxel and Pemetrexed, NCT04623775); Dostarlimab in combination with Cobolimab and Docetaxel (NCT04655976); Pembrolizumab/Vibostolimab (NCT04738487); Tislelizumab in combination with Ociperlimab (NCT04746924); Zimberelimab in combination with Etrumadenant and Domvanalimab (NCT04791839); Tislelizumab in combination with Ociperlimab and Concurrent Chemoradiotherapy (Cisplatin, carboplatin, etoposide, paclitaxel, pemetrexed, NCT04866017); Pembrolizumab in combination with SEA-CD40 with or without chemotherapy (Pemetrexed and Carboplatin, NCT04993677); Durvalumab in combination with Domvanalimab (NCT05211895); Durvalumab in combination with Oleclumab or Monalizumab (NCT05221840); Pembrolizumab/Vibostolimab in combination with chemotherapy (Paclitaxel or Nab-Paclitaxel and Carboplatin; or Carboplatin or Cisplatin and Pemetrexed, NCT05226598); Pembrolizumab/Vibostolimab (MK-7684A) in combination with concurrent chemoradiotherapy (NCT05298423); Domvanalimab in combination with Zimberelimab (NCT04736173).

Angiogenesis: Currently, the FDA has approved specific combinations of anti-angiogenic drugs with ICBs for NSCLC patients (ABCP regimen studied in IMpower150 trial). Patients displaying a high angiogenic signal may potentially benefit from approved or investigational combination therapies comprising anti-PD-1/PD-L1 and an anti-angiogenic drug. Atezolizumab in combination with Bevacizumab, carboplatin and paclitaxel (NCT02366143); Nivolumab in combination with the tyrosine kinase inhibitor AL3818.

(NCT04165330); Atezolizumab in combination with Bevacizumab (NCT03337698); Nivolumab in combination with Ramucirumab (NCT03527108); Pembrolizumab in combination with Ramucirumab (NCT04340882); Atezolizumab in combination with Bevacizumab (NCT04958811); Pembrolizumab in combination with Sitravatinib (NCT04925986); Pembrolizumab in combination with TATE (Trans-arterial Tirapazamine Embolization) (NCT04701476); Nivolumab in combination with Cabozantinib S-malate, or in combination with Cabozantinib S-malate, Docetaxel, Gemcitabine Hydrochloride, Nab-paclitaxel, Paclitaxel, Ramucirumab (NCT04310007); Durvalumab in combination with cediranib (AZD2171) (NCT03334617); Camrelizumab in combination with Apatinib Mesylate (NCT04203485); Nivolumab in combination with Sitravatinib.

Metabolism: Patients displaying a high metabolic signal may potentially benefit from investigational combination therapies comprising ICI therapy and a metabolic intervention, currently investigated in clinical trials. Atezolizumab and Linagpltin (NCT03337698); Nivolumab or Pembrolizumab in combination with Metformin (NCT04114136); Nivolumab or Pembrolizumab in combination with Rosiglitazone (NCT04114136); and pembrolizumab in combination with Talabostat Mesylate (NCT04171219).

Example 5: Systems for the Performance of the Invention

Figure 10:
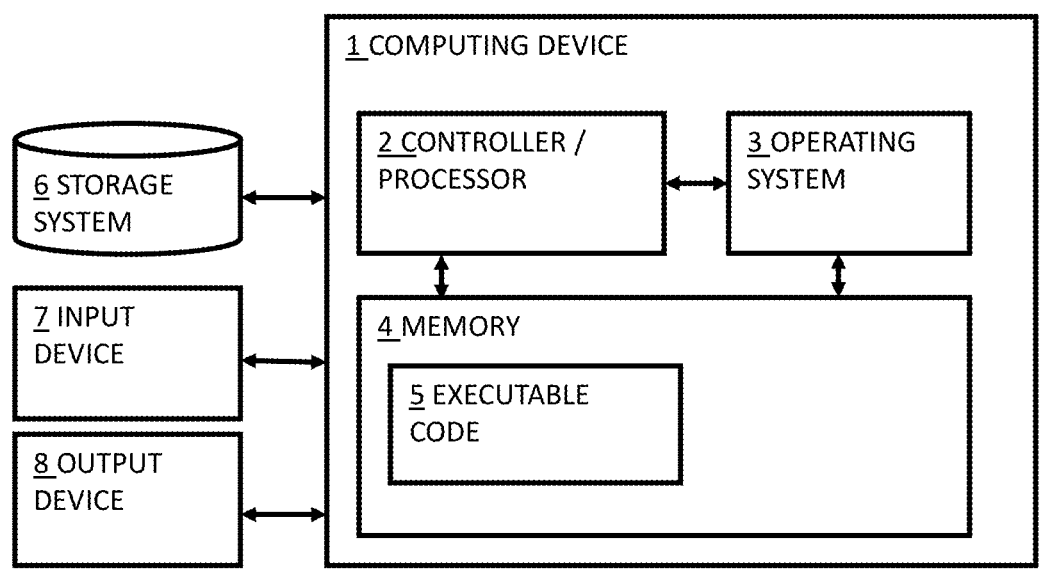
FIG. 10: Diagram of an embodiments of a computing device to be used in embodiments of the invention.

Reference is now made to FIG. 10, which is a block diagram depicting a computing device, which may be included within an embodiment of a system for selecting a therapeutic agent to treat a cancer in a subject, according to some embodiments.

Computing device 1 may include a processor or controller 2 that may be, for example, a central processing unit (CPU) processor, a chip or any suitable computing or computational device, an operating system 3, a memory 4, executable code 5, a storage system 6, input devices 7 and output devices 8. Processor 2 (or one or more controllers or processors, possibly across multiple units or devices) may be configured to carry out methods described herein, and/or to execute or act as the various modules, units, etc. More than one computing device 1 may be included in, and one or more computing devices 1 may act as the components of, a system according to embodiments of the invention.

Operating system 3 may be or may include any code segment (e.g., one similar to executable code 5 described herein) designed and/or configured to perform tasks involving coordination, scheduling, arbitration, supervising, controlling or otherwise managing operation of computing device 1, for example, scheduling execution of software programs or tasks or enabling software programs or other modules or units to communicate. Operating system 3 may be a commercial operating system. It will be noted that an operating system 3 may be an optional component, e.g., in some embodiments, a system may include a computing device that does not require or include an operating system 3.

Memory 4 may be or may include, for example, a Random-Access Memory (RAM), a read only memory (ROM), a Dynamic RAM (DRAM), a Synchronous DRAM (SD-RAM), a double data rate (DDR) memory chip, a Flash memory, a volatile memory, a non-volatile memory, a cache memory, a buffer, a short-term memory unit, a long-term memory unit, or other suitable memory units or storage units. Memory 4 may be or may include a plurality of possibly different memory units. Memory 4 may be a computer or processor non-transitory readable medium, or a computer non-transitory storage medium, e.g., a RAM. In one embodiment, a non-transitory storage medium such as memory 4, a hard disk drive, another storage device, etc. may store instructions or code which when executed by a processor may cause the processor to carry out methods as described herein.

Executable code 5 may be any executable code, e.g., an application, a program, a process, task, or script. Executable code 5 may be executed by processor or controller 2 possibly under control of operating system 3. For example, executable code 5 may be an application that may selecting a therapeutic agent to treat a cancer in a subject as described herein. Although, for the sake of clarity, a single item of executable code 5 is shown in FIG. 10, a system according to some embodiments of the invention may include a plurality of executable code segments similar to executable code 5 that may be loaded into memory 4 and cause processor 2 to carry out methods described herein.

Storage system 6 may be or may include, for example, a flash memory as known in the art, a memory that is internal to, or embedded in, a micro controller or chip as known in the art, a hard disk drive, a CD-Recordable (CD-R) drive, a Blu-ray disk (BD), a universal serial bus (USB) device or other suitable removable and/or fixed storage unit. Data pertaining to a sample (e.g., a blood sample) taken from one or more patients may be stored in storage system 6, and may be loaded from storage system 6 into memory 4 where it may be processed by processor or controller 2. In some embodiments, some of the components shown in FIG. 10 may be omitted. For example, memory 4 may be a non-volatile memory having the storage capacity of storage system 6. Accordingly, although shown as a separate component, storage system 6 may be embedded or included in memory 4.

Input devices 7 may be or may include any suitable input devices, components, or systems, e.g., a detachable keyboard or keypad, a mouse and the like. Output devices 8 may include one or more (possibly detachable) displays or monitors, speakers and/or any other suitable output devices. Any applicable input/output (I/O) devices may be connected to Computing device 1 as shown by blocks 7 and 8. For example, a wired or wireless network interface card (NIC), a universal serial bus (USB) device or external hard drive may be included in input devices 7 and/or output devices 8. It will be recognized that any suitable number of input devices 7 and output device 8 may be operatively connected to Computing device 1 as shown by blocks 7 and 8.

A system according to some embodiments of the invention may include components such as, but not limited to, a plurality of central processing units (CPU) or any other suitable multi-purpose or specific processors or controllers (e.g., similar to element 2), a plurality of input units, a plurality of output units, a plurality of memory units, and a plurality of storage units.

Figure 11:
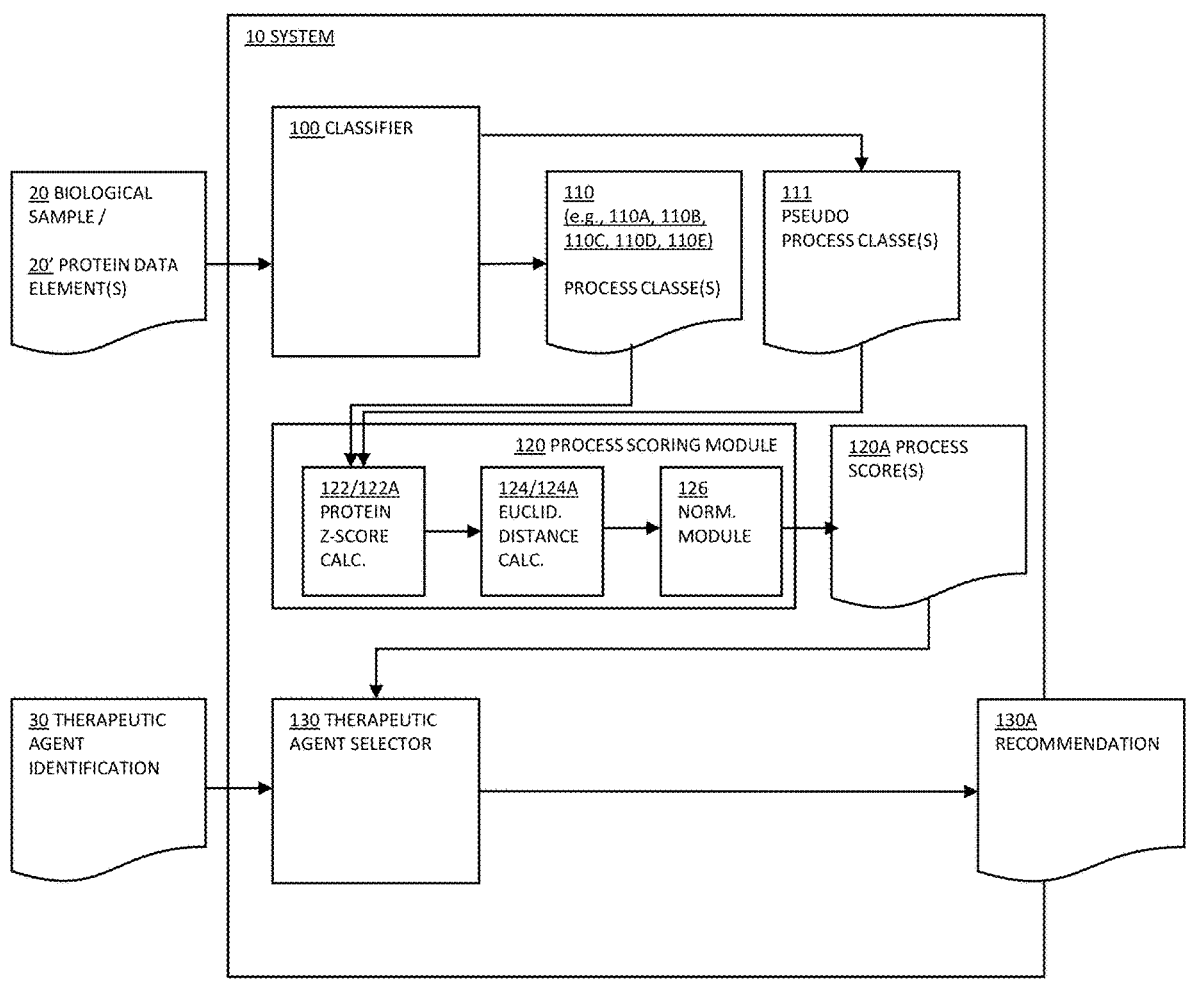
FIG. 11: Diagram of an embodiment of a system of the invention.

Reference is now made to FIG. 11, which is a block diagram, depicting an example of a system 10 for recommending 130A, or selecting a therapeutic agent for treating cancer in a subject or patient, according to some embodiments of the invention.

According to some embodiments of the invention, system 10 may be implemented as a software module, a hardware module, or any combination thereof. For example, system 10 may be, or may include a computing device such as element 1 of FIG. 10, and may be adapted to execute one or more modules of executable code (e.g., element 5 of FIG. 10) such as modules 100, 110, 120 and/or 130 of FIG. 11, to select a therapeutic agent for treating cancer, as elaborated herein.

As shown in FIG. 11, arrows may represent flow of one or more data elements to and from system 10, and/or among modules or elements of system 10. Some arrows have been omitted in FIG. 11 for the purpose of clarity.

Figure 12:
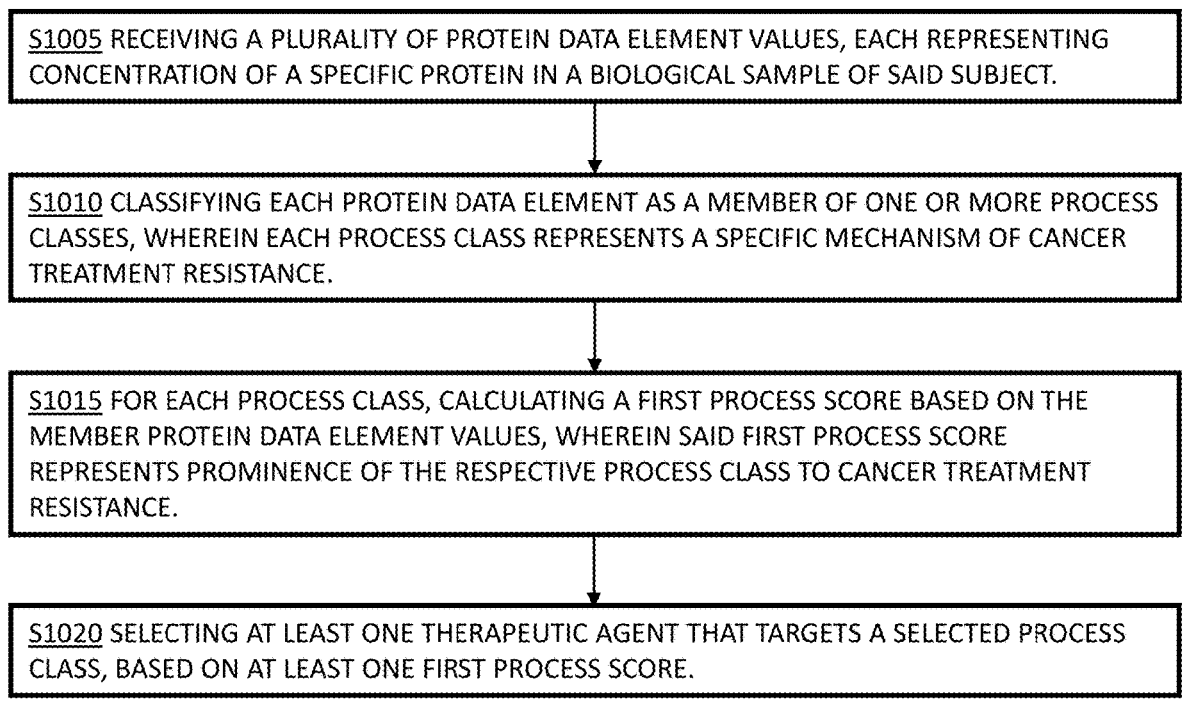
FIG. 12: Diagram of an embodiment of a method of the invention.

Reference is also made to FIG. 12, which is a flow diagram, depicting an example of a method of recommending, or selecting a therapeutic agent for treating cancer in a subject or patient, by at least one processor (e.g., processor 2 of FIG. 10) according to some embodiments of the invention.

As shown in step S1005, system 10 may receive (e.g., via input device 7 of FIG. 10) one or more (e.g., a plurality of) protein data element 20' values, each representing concentration of a specific protein in a biological sample 20 of a subject.

System 10 may include a classification module, or classifier 100. As shown in step S1010, classifier 100 may be configured to classify each protein data element 20' as a member of one or more process classes 110 (e.g., 110A, 110B, 110C, 110D, 110E). Each process class 110 may represent a specific mechanism of cancer treatment resistance. For example, a first process class 110A may represent a process of inflammation; another process class 110B may represent a process of proliferation; another process class 110C may represent a process of immune modulation; another process class 110D may represent a process of angiogenesis; and yet another process class 110E may represent a process of metabolism. It may be appreciated that additional types of process classes 110 may represent additional biological processes, and may be defined in relation to specific applications.

System 10 may include a process scoring module 120. As shown in step S1015, process scoring module 120 may be configured to calculate, for one or more (e.g., each) process class 110, a process score 120A based on the member protein data element values 20'. process score 120A may represent prominence, or significance of the respective process class 110 to affect cancer treatment resistance.

System 10 may receive (e.g., via input device 7 of FIG. 10) one or more (e.g., a plurality of) therapeutic agent identification data elements 30, each representing an identification (e.g., a name, an identifying number, etc.) of a specific therapeutic agent (e.g., a chemical substance, a drug, etc.) According to some embodiments, and as elaborated herein, System 10 may include a therapeutic agent selector module. As shown in step S1020 (FIG. 12), therapeutic agent selector module 130 may be configured to selecting at least one therapeutic agent data elements 30 of the plurality of therapeutic agent data elements 30, based on the one or more process scores 120A. For example, therapeutic agent selector module 130 may produce a recommendation data element 130A, that may include a recommendation for administering, to the subject, a specific therapeutic agent 30 that is known to treat the most prominent process class 110, e.g., the process class 110 having the highest associated process score 120A. As elaborated herein, embodiments of the invention (e.g., system 10) may provide a practical application for selecting or recommending specific treatment for cancer patients. As such, embodiments of the invention may provide an improvement over currently available systems and methods in the technological field of assistive diagnostics in that they will accurately provide a recommendation for a combination therapy. It is well known that most cancers require the use of more than one therapeutic agent in order to produced sustained remission. However, with the numerous therapeutic avenues now available it is difficult for a physician to know which to selected. Further, the wrong choice leads to unnecessary side effects as well as increased cancer progression while the wrong agent is being administered. The ability to accurately target a resistance process active in a subject with cancer greatly improves the likely treatment outcome.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A method of selecting a therapeutic agent to treat a cancer in a subject by at least one processor, the method comprising:
    receiving a plurality of protein data element values, each representing the level of a specific protein in a biological sample of said subject;
    classifying each protein data element as a member of one or more process classes, wherein each process class represents a specific mechanism of cancer treatment resistance;
    for each process class, calculating a first process score as a Euclidean distance of a vector whose components are each derived from respective member protein data element values, wherein the first process score represents prominence of the respective process class to cancer treatment resistance;
    selecting at least one therapeutic agent that targets a selected process class, wherein said process class is selected based on said process class's first process score; and
    administering said selected at least one therapeutic agent to said subject.

2. The method of claim 1, wherein a process score beyond a predetermined threshold indicates the process is active in said subject, and wherein said selected process class is a process class active in said subject.

3. The method of claim 1, further comprising producing at least one recommendation data element, representing recommendation for administering the selected at least one therapeutic agent to said subject.

4. The method of claim 1, wherein said cancer is lung cancer.

5. The method of claim 1, wherein said biological sample is selected from blood plasma, whole blood, blood serum or peripheral blood mononuclear cells.

6. The method of claim 1, wherein said plurality of protein data element values comprises element values from at least 80 different proteins.

7. The method of claim 1, wherein said biological sample is obtained from a subject naïve to treatment and said therapeutic agent is a first line treatment.

8. The method of claim 1, wherein calculating a first process score of a process class having N member protein data elements comprises:
    normalizing the values of the N member protein data elements according to a common mean value, to produce N corresponding z-score values, each representing a standard deviation distance of a protein data element value from the common mean value;
    calculating an interim score value as a Euclidean distance of an N dimensional vector, whose components are the N z-score values; and
    normalizing the interim score value according to the number N of member protein data elements, to produce the first process score.

9. The method of claim 1, further comprising
    producing a plurality of pseudo process classes, each comprising a plurality of randomly selected protein data element of the patient;
    for each pseudo process class, calculating a respective process score, to obtain a plurality of second process scores;
    accumulating the plurality of second process scores, to obtain an expected distribution of second process scores in the subject;
    generating a third process score for each process representative of the probability that the first process score would be received based on the expected distribution of the plurality of second process scores in the subject and wherein said selected process is a process with a third process score that is below a predetermined threshold.

10. The method of claim 1, further comprising normalizing the protein data element values of the subject such that the sum of all protein data element values equals a predefined sum value, and wherein calculating the first process score is based on the member protein data elements' normalized values.

11. The method of claim 1, wherein said process classes comprise inflammation, proliferation, immune modulation, angiogenesis and metabolism.

12. The method of claim 11, wherein:
    a. said process class is inflammation and said therapeutic agent is selected from: BMS-986253 (anti-IL-8), BNT411 (TLR7 antagonist), BDC-1001 (anti-HER2 and TLR7/8 agonis conjugate), Tocilizumab (anti-IL-6R), TransCon TLR7/8 Agonist (TLR7/8 agonist), Canakinumab (anti-IL-1 beta), and Pixatimod (TLR9 agonist);
    b. said process class is proliferation and said therapeutic agent is selected from: Carboplatin, Pemetrexed, Paclitaxel, Nab-paclitaxel, Cisplatin, Carboplatin, Etoposide, FOLFOX, Datopotamab Deruxtecan (anti-TACSTD2 antibody-drug conjugate), radiotherapy, chemoradiotherapy, Stereotactic radiation, Tisotumab vedotin (anti-CD142 antibody-drug conjugate), Vistusertib (mTOR inhibitor), AZD9150 (STAT3 oligonucleotide inhibitor), Tomivosertib (MNK1/2 inhibitor), Sacituzumab Govitecan-hziy (SG, anti-TACSTD2 antibody-drug conjugate), Azacitidine+Entinostat (chemotherapy+HDAC inhibitor), brentuximab vedotin (anti-CD30 antibody-drug conjugate), ATE: Trans-arterial Tirapazamine (embolization and chemosensitizing agent), LMB-100 (antibody-Drug Conjugate targeting mesothelin), SAR408701 (Tusamitamab ravtansine, anti-CEACAM5-maytansinoid Antibody-drug Conjugate), Cryosurgical freezing, Non-ablative Cryosurgical freezing, Ipatasertib (AKT inhibitor), RO6958688 (bispecific antibody targeting CEA and CD3), Cobimetinib (MEK inhibitor), Sacituzumab Govitecan (anti-TACSTD2 antibody-drug conjugate), and 6-Thio-2'-Deoxyguanosine (telomere-disrupting compound);

c. said process class is immune modulation and said therapeutic agent is selected from: AZD6738 (ATR kinase inhibitor), Oleclumab (anti-NT5E), Olaparib (PARP inhibitor), CPI-444 (ADORA2A/B antagonist), Lifileucel, LN-145, GSK4428859A (Anti-TIGIT), GSK3359609/Feladilimab (agonstic anti-ICOS), MK-5890 (Anti-CD27 agonist), MK-0482 (LILRB4 signaling inhibitor), MK-4830 (Anti-LILRB2), Domvanalimab or AB154 (Anti-TIGIT), Etrumadenant (ADORA2A/B antagonist), Tiragolumab (anti-TIGIT), Olaparib (PARP inhibitor), Niraparib (PARP inhibitor), Relatlimab (anti-LAG3), Cobolimab (Anti-HAVCR2), Pembrolizumab/Vibostolimab (MK-7684A, Anti-TIGIT), Ociperlimab (Anti-TIGIT), Etrumadenant+ Domvanalimab (ADORA2A/B antagonist+anti-TIGIT (alteranative ICI)), SEA-CD40 (Agonistic anti-CD40), Oleclumab (Anti-NT5E), Monalizumab (Anti-KLRC1), and Sitravatinib (Anti-RTKs (receptor tyrosine kinases) including TYRO3, VEGFR2 AXL, MET, FLT3, KIT, FLT1, DDR2, NTRK1, FLT4, EPHA3, PDGFRA, METRK, EPHB6, RET, KDR));

d. said process class is angiogenesis and said therapeutic agent is selected from: AL3818 (Tyrosine kinase inhibitor), Bevacizumab (anti-VEGFA), Ramucirumab (anti-KDR), Sitravatinib (Tyrosine kinase inhibitor), ATE: Trans-arterial Tirapazamine Embolization, Cabozantinib S-malate (Tyrosine kinase inhibitor), cediranib (Tyrosine kinase inhibitor), Anlotinib hydrochloride (Anti-VEGFR1, VEGFR3, VEGFR2/KDR, PDGFR-α, c-Kit, FGFR1, FGFR2, FGFR3), Endostar (Anti-bFGF, FGF-2,VEGF), Famitinib (RTK), Lenvatinib (Tyrosine kinase inhibitor), Vorolanib (Anti-PDGFRA, PDGFRB, CSF1R, KDR, FLT1, FLT4), Defactinib (Anti-PTK2, PTK2B), Nintedanib (Tyrosine kinase inhibitor), Regorafenib (Tyrosine kinase inhibitor), cabozantinib (Tyrosine kinase inhibitor), Axitinib (Tyrosine kinase inhibitor), and AL3818 or anlotinib (Tyrosine kinase inhibitor);

e. said process class is metabolism and said therapeutic agent is selected from: Linagliptin (DPP4 inhibitor), Metformin (antihyperglycemic agent), Rosiglitazone (PPARs activator), Talabostat (DPP4 inhibitor), and telaglenastat (glutaminase inhibitor); or f. a combination thereof.

13. The method of claim 1, further comprising predicting the response of said subject to an immunotherapy.

14. The method of claim 13, wherein at least one of:

a. if said subject is responsive to said immunotherapy administering to said subject a combined treatment of said immunotherapy and said at least one therapeutic agent;

b. if said subject is non-responsive to said immunotherapy administering to said subject said at least one therapeutic agent instead of said immunotherapy; and c. if said subject is non-responsive to said immunotherapy administering to said subject a combined treatment of said immunotherapy and said at least one therapeutic agent and determining if said at least one therapeutic agent converts said non-responsive subject to a responsive subject.

15. The method of claim 13, wherein said predicting the response to said immunotherapy comprises:

a. receiving a plurality of protein data element values
  i. in a population of subjects suffering from cancer and known to respond to said immunotherapy (responders); and
  ii. in a population of subjects suffering from cancer and known to not respond to said therapy (non-responders);

b. calculating for proteins of said plurality of protein data element values a resistance score, where said resistance score is based on the similarity of said protein data element value in said subject to the protein data element value in said responders and the similarity of said protein data element value in said subject to said non-responders; and c. classifying a protein of said plurality of protein data element values with a resistance score beyond a predetermined threshold as a resistance-associated protein;

wherein a subject with a number of resistance-associated proteins above a predetermined number is predicted to be resistant to said therapy and a subject with a number of resistance-associated factors at or below a predetermined number is predicted to respond to said therapy.

16. The method of claim 13, wherein said predicting the response to said immunotherapy comprises:

a. receiving a plurality of protein data element values
  i. in a population of subjects suffering from cancer and known to respond to said immunotherapy (responders); and
  ii. in a population of subjects suffering from cancer and known to not respond to said therapy (non-responders);

b. calculating for each protein of said plurality of protein data element values a resistance score, where said resistance score is based on the similarity of said protein data element value in said subject to the protein data element value in said responders and the similarity of said protein data element value in said subject to said non-responders;

c. classifying a protein of said plurality of protein data element values with a resistance score above a predetermined threshold as a resistance-associated protein;

d. summing the number of resistance-associated proteins present for said subject; and e. applying a trained machine learning algorithm to said number of resistance-associated proteins and at least one clinical parameter of said subject, wherein said trained machine learning algorithm outputs a final resistance score and a final resistance score above a predetermined threshold indicates said subject is resistant to said therapy.

17. The method of claim 16, comprising before (b) selecting a subset of said plurality of factors, wherein said subset comprises factors that best differentiate between said responders and non-responders, and wherein said calculating is for each factor of said subset.

18. The method of claim 16, wherein said calculating comprises applying a machine learning algorithm trained on a training set comprising said received factor expression levels in responders and non-responders and the sex of each responder and non-responder to individual received factor expression levels from said subject and said subject's sex and wherein said machine learning algorithm outputs said resistance score.

19. The method of claim 13, wherein said predicting the response to said immunotherapy comprises:
 a. receiving a plurality of protein data element values
   i. in a population of subjects suffering from cancer and known to respond to said immunotherapy (responders); and
   ii. in a population of subjects suffering from cancer and known to not respond to said therapy (non-responders);
 b. calculating for factors of said plurality of factors a resistance score, where said resistance score is based on the similarity of said factor expression level in said subject to the factor expression level in said responders and the similarity of said factor expression level in said subject to said non-responders and wherein said calculating comprises applying a machine learning algorithm trained on a training set comprising said received factor expression levels in responders and non-responders and the sex of each of said responders and non-responders to individual received factor expression levels from said subject and said subject's sex and wherein said machine learning algorithm outputs said resistance score; and
 c. sum said calculated resistance scores to produce a total resistance score;
   wherein a subject with a total resistance score beyond a predetermined threshold is predicted to be resistant to said therapy.

* * * * *